United States Patent
Wos et al.

(10) Patent No.: US 7,041,696 B2
(45) Date of Patent: May 9, 2006

(54) INTERLEUKIN-1β CONVERTING ENZYME INHIBITORS

(75) Inventors: John August Wos, Maineville, OH (US); David Lindsey Soper, Mason, OH (US); Steven Victor O'Neil, Morrow, OH (US); Yili Wang, Mason, OH (US); Kofi Abeka Oppong, Fairfield, OH (US); Michael Christopher Laufersweiler, Maineville, OH (US); Jian Chen, Mason, OH (US); Biswanath De, Cincinnati, OH (US); Thomas Prosser Demuth, Jr., Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 236 days.

(21) Appl. No.: 10/457,181

(22) Filed: Jun. 9, 2003

(65) Prior Publication Data
US 2003/0236296 A1 Dec. 25, 2003

Related U.S. Application Data

(60) Provisional application No. 60/389,335, filed on Jun. 17, 2002.

(51) Int. Cl.
C07D 487/04 (2006.01)
A61K 31/403 (2006.01)
A61P 29/00 (2006.01)

(52) U.S. Cl. .................................. 514/413; 540/461
(58) Field of Classification Search ................ 540/461; 514/413
See application file for complete search history.

(56) References Cited

OTHER PUBLICATIONS

Thorsett, E.D., "Conformationally Restricted Inhibitors of Angiotensin Converting Enzyme", *Actualites de Chimie Therapeutique*, 1986, vol. 13, pp. 257-268.
Beal, L.M. et al., "A Sequential Electrochemical Oxidation—Olefin Metathesis Strategy for the Construction of bicyclic Lactam Based Peptidomimetics", *Tetrahedron Letters*, 1998, vol. 39, pp. 4639-4642.
Grossmith, C.E. et al., "Synthesis of Novel Unsaturated Bicyclic Lactams by Ring-Closing Metathesis", *Synlett*, 1990, No. 10, pp. 1660-1662.

Primary Examiner—Bruck Kifle
(74) Attorney, Agent, or Firm—Richard S. Echler, Sr.

(57) ABSTRACT

The present invention relates to interleukin-1β converting enzyme inhibitors having the formula:

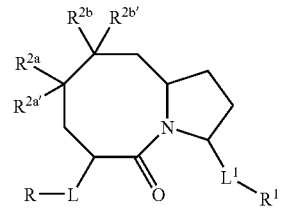

R is a carbocyclic or heterocyclic ring;
$R^1$ is a cysteine trap;
$R^{2a}$, $R^{2a'}$, $R^{2b}$, and $R^{2b'}$ are each independently hydrogen, $C_1$–$C_4$ alkyl, $C_1$–$C_4$ alkoxy, and mixtures thereof; or $R^{2a'}$ and $R^{2b'}$ can taken together to form a double bond;
L and $L^1$ are linking groups having the formula:

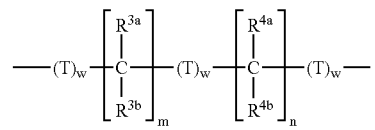

T is selected from the group consisting of:
i) —$NR^6$—;
ii) —O—;
iii) —$NR^6 S(O)_2$—;
iv) —$S(O)_2 NR^6$—; and
v) mixtures thereof;
$R^6$ is hydrogen, substituted or unsubstituted $C_1$–$C_{20}$ linear, branched, or cyclic alkyl, $C_6$–$C_{20}$ aryl, $C_7$–$C_{20}$ alkylenearyl, and mixtures thereof; the indices w, $w^1$, and $w^2$ are each independently 0 or 1;
i) hydrogen;
ii) $C_1$–$C_4$ linear, branched, and cyclic alkyl;
iii) $R^{3a}$ and $R^{3b}$ or $R^{4a}$, and $R^{4b}$ can be taken together to form a carbonyl unit;
iv) two $R^{3a}$ or two $R^{3b}$ units from adjacent carbon atoms or two $R^{4a}$ or two $R^{4b}$ units from adjacent carbon atoms can be taken together to form a double bond; and
v) mixtures thereof;
the index m is from 0 to 5; the index n is from 0 to 5.

44 Claims, No Drawings

INTERLEUKIN-1β CONVERTING ENZYME INHIBITORS

CROSS REFERENCE TO RELATED APPLICATIONS

This application claims priority under Title 35, United States Code 119(e) from Provisional Application Ser. No. 60/389,335, filed Jun. 17, 2002.

FIELD OF THE INVENTION

The present invention relates to novel 8,5-fused ring heterocycles that are Interleukin-β converting enzyme (ICE) inhibitors. The present invention also relates to pharmaceutical compositions comprising said inhibitors. The present invention further relates to methods for controlling one or more disease processes related to Interleukin-β activity.

BACKGROUND OF THE INVENTION

Cytokines, in general, are important signaling molecules that are essential to immune and inflammatory responses in mammals. Interleukin-1β and IL-18 are key components of the cytokine network. IL-1β stimulates the production of Tumor Necrosis Factor-α (TNF-α), and the combined action of IL-1β, IL-18 and TNF-α induces further cytokine production, chemokine production, expression of cellular adhesion molecules, and increased vascular permeability. In addition, IL-1β stimulates fibroblast differentiation and proliferation, the production of prostaglandins, collagenase and phospholipase by synovial cell and chondrocytes, basophil and eosinophil degranulation, and neutrophil activation. These mediators contribute to autoimmune and inflammatory disorders in many organ systems.

IL-1β possesses diverse biological effects contributing to the pathogenesis of acute and chronic inflammatory and autoimmune diseases (C A Dinarello, *Blood,* (1996) 87, 2095). For example, Il-1β contributes to disease progression in rheumatoid arthritis and osteoarthritis, where it mediates inflammatory symptoms, contributes to the destruction of cartilage proteoglycan, and also contributes to bone loss in afflicted joints. IL-1β overexpression also contributes to disease progression in atherosclerosis by regulating the expression and activation of matrix metalloproteases. Other conditions where IL-1β plays a major role in pathogenesis include sepsis syndrome, inflammatory bowel syndrome, acute and chronic myelogenous leukemia, insulin-dependent diabetes mellitus, osteoporosis, and periodontal disease.

The caspases are a family of structurally similar, intracellular cysteine proteases that play an important role in cytokine maturation and apoptosis. Caspase-1 (interleukin-1β converting enzyme, ICE) is primarily responsible for key steps in immunity and the inflammatory response since it catalyzes the proteolytic cleavage of the pro-inflammatory cytokines pro-IL-1β and pro-IL-18 to the bioactive forms IL-1β and IL-18. Since IL-1β triggers a multitude of biological responses and is implicated in the pathogenesis of many inflammatory diseases, as outlined above, the inhibition of ICE is a recognized target for therapeutic intervention. Therefore, ICE inhibitors have utility for the treatment of inflammatory diseases and autoimmune diseases, such as RA and OA. In addition, other caspases and related homologs of ICE appear to be involved regulating biological processes such as apoptosis. Therefore, inhibition of caspases also provides a recognized therapeutic approach for treating additional pathological conditions. Diseases where caspase inhibitors can provide theraputic utility include neurodegenerative diseases (such as Alzheimer's, Huntington's, and Parkinson's diseases), ischemia, stroke, and trauma.

There is therefore a long felt need in the art for pharmaceutical compositions which comprise novel active ingredients for reversibly or irreversibly inhibiting Caspase enzymes resulting in the treatment of pathological conditions and diseases described further herein, inter alia, inflammation of joints and other forms of synovial tissue associated with osteoarthritis and rheumatoid arthritis, Huntington's Disease, Alzheimer's disease, neuronal death, brain, intestinal or mycardial ischemia, repurfusion injury, endotoxic shock, amyotrophic lateral sclerosis, multiple sclerosis, atherosclerosis, hepatitis, inflammatory bowel syndrome, shigellosis, meningitis, sepsis, acute and chronic myelogenous leukemia, insulin-dependent diabetes mellitus, osteoporosis, and periodontal disease. Each of these disease states involves cytokine activity, which can be abated, controlled or otherwise mediated by the limiting or stopping the activity of one or more Caspase enzymes.

SUMMARY OF THE INVENTION

The present invention meets the aforementioned needs in that it has been surprisingly found that certain 8,5-fused ring heterocycles are effective for inhibiting Interleukin Converting Enzymes and thereby preventing, abating, or otherwise controlling the extracellular release of the 17 kD IL-1β enzyme which is proposed to be the active component responsible for the herein described disease states.

The first aspect of the present invention relates to compounds which are capable off interfering with the release of the IL-1β protease, said compounds having the formula:

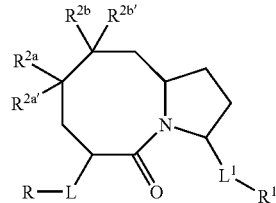

R is a carbocyclic or heterocyclic ring;
$R^1$ is a cysteine trap;
$R^{2a}$, $R^{2a'}$, $R^{2b}$, and $R^{2b'}$ are each independently hydrogen, $C_1$–$C_4$ alkyl, $C_1$–$C_4$ alkoxy, and mixtures thereof; or $R^{2a'}$ and $R^{2b'}$ can taken together to form a double bond;
L and $L^1$ are linking units each independently having the formula:

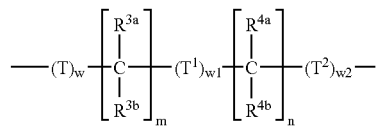

T, $T^1$, and $T^2$ are each independently selected from the group consisting of:
i) —$NR^6$—;
ii) —O—;
iii) —$NR^6S(O)_2$—;
iv) —$S(O)_2NR^6$—; and v) mixtures thereof;
$R^6$ is hydrogen, substituted or unsubstituted $C_1$–$C_{10}$ linear, branched, or cyclic alkyl, $C_6$–$C_{10}$ aryl, $C_7$–$C_{12}$ alkylene-aryl, and mixtures thereof; the indices w, $w^1$, and $w^2$ are each independently 0 or 1;
i) hydrogen;
ii) $C_1$–$C_4$ linear, branched, and cyclic alkyl;
iii) $R^{3a}$ and $R^{3b}$ or $R^{4a}$, and $R^{4b}$ can be taken together to form a carbonyl unit;
iv) two $R^{3a}$ or two $R^{3b}$ units from adjacent carbon atoms or two $R^{4a}$ or two $R^{4b}$ units from adjacent carbon atoms can be taken together to form a double bond; and
v) mixtures thereof;

the index m is from 0 to 5; the index n is from 0 to 5.

Another aspect of the present invention relates to pharmaceutical compositions. The compounds of the present invention have improved oral bioavailability and this advantage is made use of by the second aspect of the present invention wherein the formulator can deliver the compounds of the present invention to a human or higher mammal by administering a composition comprising:

a) an effective amount of one or more interleukin-1β converting enzyme inhibitors according to the present invention; and
b) one or more pharmaceutically acceptable excipients.

As described herein below, the compositions of the present invention are effective in controlling one or more interleukin-1β converting enzyme inhibitor mediated or interleukin-1β converting enzyme inhibitor modulated mammalian diseases or conditions.

A further aspect of the present invention relates to methods for controlling diseases or disease states which are related to or caused by the increased activity of one or more Caspase enzymes, inter alia, Interleukin-1β Converting Enzyme (Caspase-1). The unmediated or uncontrolled activity of said enzymes can cause the release of higher levels of cytokines which exacerbate the disease state. The methods of the present invention control the amplification of IL-1β and other cytokines which are capable of being released by controlling the initial release of IL-1β.

Further, this invention relates to methods for treating diseases mediated by Caspase enzymes, including for example, acute and chronic inflammatory-mediated diseases, autoimmune diseases, destructive bone diseases, proliferative disorders, infectious diseases, and degenerative diseases.

In addition, this invention also relates to methods of treating diseases mediated by IL-1β. Specifically, the subject invention relates to methods for treating pathological conditions and diseases, such as neuronal death, brain, intestinal or mycardial ischemia, repurfusion injury, endotoxic shock, amyotrophic lateral sclerosis, multiple sclerosis, Parkinson's disease, Huntington's disease, Alzheimer's disease, atherosclerosis, hepatitis, inflammatory bowel syndrome, shigellosis, meningitis, sepsis, acute and chronic myelogenous leukemia, insulin-dependent diabetes mellitus, osteoporosis, periodontal disease, rheumatoid arthritis (RA) and osteoarthritis (OA).

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified.

DETAILED DESCRIPTION OF THE INVENTION

The present invention relates to compounds which are interleukin-1β converting enzyme inhibitors, said compounds comprising an 8,6-fused ring system. Interleukin-1β is a cyctokine released by a chemical reaction catalyzed by the enzyme Caspase-1 (ICE) and the present invention specifically targets the inhibition of Caspase-1. The compounds of the present invention are surprisingly specific for inhibiting Caspase-1 enzyme, as well as being modifiable for to have enhanced specificity for other Caspase enzymes.

The compounds of the present invention comprise three elements:
i) novel 8,5-fused ring scaffolds;
ii) R units which are carbocyclic or heterocyclic rings attached by way of a linking unit to said scaffolds; and
iii) $R^1$ units which are cysteine traps attached by way of a linking unit to said scaffolds.

The novel ICE inhibitors of the present invention have been surprisingly found to satisfy the specific size, shape, and binding requirement of the Caspase-1 active site and therefore are capable of reversibly or irreversibly inactivating the enzyme Caspase-1. However, the compounds of the present invention can also be modified within the metes and bounds of the present invention to provide activity against other cysteine and serine protease enzymes as well.

The novel scaffolds of the present invention surprisingly position the selected R unit, encompassed within the description herein below, in a manner allowing for a propitious interaction between the novel compounds of the present invention and Caspase-1.

The cysteine traps of the present invention can be chosen by the formulator to interact reversibly or irreversibly with the target Caspase enzyme. In general, these traps comprise a first reactive moiety and a second reactive moiety. The first reactive moiety is a carboxyl unit (or carboxyl unit precursor) which is believed to fit into a specific carboxylate docking site along the enzyme active site and in doing so bring the second reactive moiety into proximity with a cysteine amino acid residue which then reacts reversibly or irreversibly with the second reactive moiety rendering the enzyme inactive. The formulator, as described herein below, may select to reversibly or irreversibly (suicide inhibitor) inhibit the activity of the Caspase enzyme depending upon the type of cytokine related disease, treatment type, or regiment of therapy.

In addition, the formulator may use either the "bio-active" or "bio-equivalent" form of a cysteine trap depending upon the pharmaceutical composition, mode of delivery, and the like. For the purposes of the present invention, the term "bio-active" is defined herein as "the chemical form of a group, unit or moiety which interacts with the target enzyme." For the purposes of the present invention, the term "bio-equivalent" is defined herein as "a precursor form of the bio-active form of a group, unit or moiety which is readily converted to the bio-active form upon delivery into the host species being treated. The bio-equivalent form is also converted to the bio-active form prior to interaction with the targeted enzymes during in vitro testing."

For the purposes of the present invention the term "hydrocarbyl" is defined herein as any organic unit or moiety which is comprised of carbon atoms and hydrogen atoms. Included within the term hydrocarbyl are the heterocycles which are described herein below. Examples of various unsubstituted non-heterocyclic hydrocarbyl units include methyl, ethyl, propyl, pentyl, 1-butenyl, 2,2-dimethypentyl, 3-ethyl-3-methylpent-1-ynyl, 8,8-dimethylnon-3-enyl, and the like.

Included within the definition of "hydrocarbyl" are the aromatic (aryl) and non-aromatic carbocyclic rings. Non-limiting examples of substituted or unsubstituted aromatic and non-aromatic carbocyclic rings include cyclopentyl, cyclohexyl, 1-ethyl-2-methyl-cyclohexyl cyclohexenyl, cycloheptanyl, cyclooctyl, octahydro-indenyl, 3,5-dimethyl-2,3,3a,4,5,6,9,9a-octahydro-1H-cyclopentacyclooctenyl, 4,6-dimethyl-1,2,3,4,4a,5,6,7,10,10a-decahydro-benzocyclooctenyl, phenyl, benzyl, 1-ethyl-2-methyl-benzyl, naphthyl, 3-methyl-1-propyl-naphthyl, indanyl, phenanthryl, 1,2,3,4-tetrahydronaphthalenyl, and the like.

The term "heterocycle" is included within the term hydrocarbyl and is described herein as a hydrocarbyl that contains one or more heteroatoms in the ring system. Heterocycle includes both aromatic (heteroaryl) and non-aromatic heterocyclic rings. Non-limiting substituted or unsubstituted examples include: pyrrolyl, 2H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, 2H-1,3-oxazinyl, 1,4-oxazinyl, morpholinyl, azepinyl, oxepinyl, 4H-1,2-diazepinyl, benzofuranyl, indolyl, 1H-indolyl, benzoxazolyl, quinolinyl, isoquinolinyl, 2H-1,4-benzoxazinyl, pyrrolidinyl, pyrrolinyl, furanyl, thiophenyl, benzimidazolyl, 6-amino-5-oxo-3,4,4a,5,6,7,10,10a-octahydro-1H-cycloocta[c]pyran-4-carboxylic acid, 6-amino-5-oxo-1,2,3,4,4a,5,6,7,10,10a-decahydro-cycloocta[c]pyridine-4-carboxylic acid, (2-Ethoxy-5-oxo-tetrahydro-furan-3-yl)-carbamic acid allyl ester and the like.

The terms "arylene" and "heteroarylene" relate to aryl and heteroaryl units which can serve as part of a linking group, for example, units having the formula:

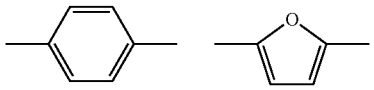

which represent an arylene and heteroarylene unit respectively.

The term "substituted" is used throughout the specification. The term "substituted" is defined herein as "encompassing moieties or units which can replace a hydrogen atom, two hydrogen atoms, or three hydrogen atoms of a hydrocarbyl moiety. Also substituted can include replacement of hydrogen atoms on two adjacent carbons to form a new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit," 3-guanidinopropyl is a "substituted $C_3$ alkyl unit," and 2-carboxypyridinyl is a "substituted heteroaryl unit." The following are non-limiting examples of units which can serve as a replacement for hydrogen atoms when a hydrocarbyl unit is described as "substituted."

i) $-[C(R^6)_2]_p(CH=CH)_qR^6$; wherein p is from 0 to 12; q is from 0 to 12;
ii) $-C(Z)R^6$;
iii) $-C(O)OR^6$
iv) $-C(Z)CH=CH_2$;
v) $-C(Z)N(R^6)_2$;
vi) $-C(Z)NR^6N(R^6)_2$;
vii) $-CN$;
viii) $-C(O)OM$
ix) $-CF_3, -CCl_3, -CBr_3$;
x) $-N(R^6)_2$;
xi) -halo
xii) $-NR^6C(Z)R^6$;
xiii) $-NR^6C(Z)N(R^6)_2$;
xiv) $-NR^6N(R^6)_2$;
xv) $-NHOR^6$;
xvi) $-OCF_3, -OCCl_3, -OCBr_3$;
xvii) $-NO_2$;
xviii) $-OR^6$;
xix) $-NR^6S(O)_2R^6$
xx) $-NR^6S(O)_2N R^6$
xxi) $-SO_2N(R^6)_2$
xxii) $-SO_2R^6$
xxiii) $-SO_3M$;
xxiv) $-OSO_3M$;
xxv) $-OP(O)(OM)_2$;
xxvi) $-P(O)(OR^6)_2$
xxvii) $-P(O)(OM)_2$
xxiii) $-OP(O)(OR^6)_2$
xxix) and mixtures thereof wherein $R^6$ is hydrogen, substituted or unsubstituted $C_1$–$C_{20}$ linear, branched, or cyclic alkyl, $C_6$–$C_{20}$ aryl, $C_7$–$C_{20}$ alkylenearyl, and mixtures thereof; M is hydrogen, or a salt forming cation; Z is =O, =S, =$NR^6$, and mixtures thereof. Suitable salt forming cations include, sodium, lithium, potassium, calcium, magnesium, ammonium, and the like. Non-limiting examples of an alkylenearyl unit include benzyl, 2-phenylethyl, 3-phenylpropyl, 2-phenylpropyl.

The compounds of the present invention include all enantiomeric and diasteriomeric forms and pharmaceutically acceptable salts of compounds having the core scaffold represented by the formula:

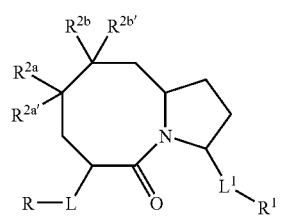

For the purposes of the present invention, the following ring numbering system is used throughout the specification to identify the Interleukin-β converting enzyme (ICE) inhibitors of the present invention:

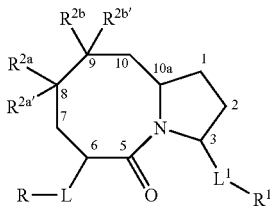

wherein $R^{2a'}$ and $R^{2b'}$ can also be taken together to form a double bond as described further herein below.

As it relates to the stereochemistry of the pyrrolo[1,2-a] azocine [8,5] fused ring system the following stereochemical assignments are given for the ring positions utilizing the ring numbering system described herein above.

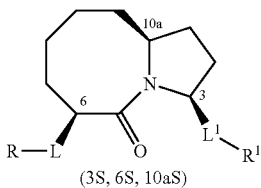
(3S, 6S, 10aS)

The analogs (compounds) of the present invention are arranged in several categories predicated on the form of the parent [8,5] fused ring system to assist the formulator in applying a rational synthetic strategy for the preparation of analogs which are not expressly examplified herein. The arrangement into categories does not imply increased or decreased efficacy for any of the compositions of matter described herein.

If necessary, the analogs (compounds) of the present invention are conveniently obtained in the salt form, for example, the trifluoroacetate salt. Also, the formulator, if convenient or practicable, can prepare a pro-drug which is capable of releasing the active compound (analog) upon uptake by the host. All of these variations are encompassed within the present invention.

As stated herein above, the form of the [8,5] fused ring scaffold indicates into which category the compounds of the present invention fall. Non-limiting examples of ring systems according to the present invention include:

i) 3,6-disubstituted 5-oxo-1,2,3,5,6,7,10,10a-octahydro-pyrrolo[1,2-a]azocine scaffold having the formula:

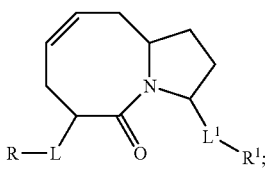

ii) 3,6-disubstituted 5-oxo-decahydro-pyrrolo[1,2-a]azocine scaffold having the formula:

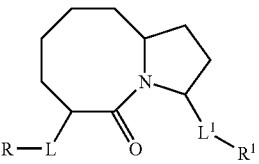

iii) 3,6,8-trisubstituted, 3,6,9-trisubstituted, or 3,6,8,9-tetrasubstituted 5-oxo-1,2,3,5,6,7,10,10a-octahydro-pyrrolo[1,2-a]azocine scaffold having the formula:

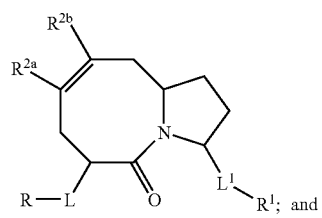
; and iv) 3,6,8-trisubstituted, 3,6,9-trisubstituted, or 3,6,8,9-tetrasubstituted 5-oxo-decahydro-pyrrolo[1,2-a]azocine scaffold having the formula:

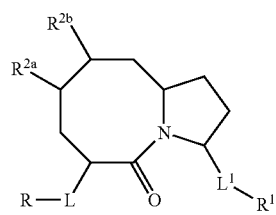

said scaffolds comprising the R, $R^1$ $R^{2a}$, $R^{2a'}$, $R^{2b}$ $R^{2b'}$ L, and $L^1$ units as described herein.

R is a carbocyclic or heterocyclic ring.

The first aspect of R relates to substituted or unsubstituted carbocyclic rings.

The first embodiment of this aspect relates to substituted and unsubstituted aryl units, inter alia, phenyl and naphthyl rings. The first iteration of this embodiment relates to substituted aryl rings comprising at least one halogen atom, non-limiting examples of which includes 2-fluorophenyl, 3-fluorophenyl, 4-fluorophenyl, 3-fluoro-4-methylphenyl, 3-fluoro-4-methoxyphenyl, 3-chloro-2-methylphenyl, 3-chloro-6-methylphenyl, 3-chloro-4-methoxyphenyl, 3-chloro-4-hydroxyphenyl, 3,5-difluorophenyl, 2,6-dichlorophenyl, 2-chlorophenyl, 3-chlorophenyl, 4-chlorophenyl, 3,4-dichlorophenyl, 3,5-dichlorophenyl, 3-chloro-4-fluorophenyl, 2-bromophenyl, 3-bromophenyl, 4-bromophenyl, and the like.

A second iteration of this embodiment relates to $C_1-C_4$ alkyl substituted aryl units non-limiting examples of which include 2-methylphenyl, 3-methylphenyl, 4-methylphenyl, 3,5-dimethylphenyl, 2-ethylphenyl, 3-ethylphenyl, 4-ethylphenyl, 3-ethyl-4-methylphenyl 3-propylphenyl, 3-butylphenyl, and the like.

A third iteration of this embodiment relates to $C_1-C_4$ alkoxy substituted aryl units non-limiting examples of which include 2-methoxyphenyl, 3-methoxyphenyl, 4-methoxyphenyl, 2-ethoxyphenyl, 3-ethoxyphenyl, 4-ethoxyphenyl, 4-propoxyphenyl, 4-butoxyphenyl, 3,4,5-trimethoxyphenyl, and the like.

A fourth iteration of this embodiment relates to amino substituted aryl units non-limiting examples of which include 3-aminonaphth-2-yl, 4-dimethylaminonaphth-1-yl, 2-aminophenyl, 3-aminophenyl, 4-aminophenyl, 3,4-dimethylaminophenyl, 4-amino-3-chlorophenyl, 4-amino-3,5-dichlorophenyl, 4-dimethylaminophenyl, 2-acetylaminophenyl, 3-acetylaminophenyl, 4-acetylaminophenyl, 4-Isobutyrylaminophenyl, 4-propionylaminophenyl, 4-butrylaminophenyl, 4-phenylacetylaminophenyl, 3,4-diacetylaminophenyl, 4-(N-acetyl-N-methylamino)-phenyl, 4-benzoylaminophenyl, and the like.

A fifth iteration of this embodiment relates to other substituted and unsubstituted aryl units non-limiting examples of which include 2-trifluoromethylphenyl, 3-trifluoromethylphenyl, 4-trifluoromethylphenyl, 4-hydroxymethyl-phenyl, naphth-1-yl, naphth-2-yl, 4-biphenyl, 4-phenoxyphenyl, 4-(3-methyl-ureido)-phenyl, 4-sulfamoylphenyl, 3-acetylphenyl, 4-acetylphenyl, 3-hydroxyphenyl, 4-hydroxyphenyl, 4-benzyloxyphenyl, 4-methanesulfonyl-phenyl, and the like.

Non-limiting examples of compounds according to the present invention which comprise the above identified R units include:

A second embodiment of this aspect relates to R units which are non-aryl carbocyclic units, inter alia, cyclopropyl, cyclobutyl, cyclohexyl, cyclopentyl, cyclohexenyl, cyclopentenyl, and the like.

The second aspect of R relates to substituted or unsubstituted heterocyclic rings. The second embodiment of this aspect relates to other substituted and unsubstituted monocyclic heteroaryl rings, inter alia, thiophene, furanyl and pyrimidine rings. The first iteration of this embodiment relates to substituted and unsubstituted monocyclic pyridinyl systems, non-limiting examples of which include, pyridin-2-yl, pyridin-3-yl, pyridin-4-yl, 3-chloropyridin-2-yl, 4-chloropyridin-2-yl, 5-chloropyridin-2-yl, 6-chloropyridin-2-yl, 3-methylpyridin-3-yl, 4-methylpyridin-3-yl, 5-methylpyridin-3-yl, vinyl pyridin-4-yl, vinyl pyridin-3-yl, and the like.

The second iteration of this embodiment relates to other substituted and unsubstituted monocyclic heteroaryl ring systems, non-limiting examples of which include, thiophen-3-yl, thiophen-2-yl, pyrimidin-2-yl, pyrimidin-4-yl, pyrimidin-5-yl, 2-isobutoxy-pyrimidin-4-yl, 2-isobutylaminopyrimidin-4-yl, 2-phenoxypyrimidin-4-yl, 2-ethyl-5-methyl-2H-pyrazol-3-yl, 2,4-dimethyl-thiazol-5-yl, 5-methyl-isoxazol-3-yl, 1H-imidazol-2-yl, [1,2,3]thiadiazol-5-yl, furan-2-yl, furan-3-yl, 4,5-dimethyl-2-furanyl, 5-bromo-2-furanyl, 2-phenylamino-pyrimidin-4-yl, and the like.

The third iteration of this embodiment relates to substituted and unsubstituted heteroaryl fused ring systems, non-limiting examples of which include quinolin-2-yl, quinolin-3-yl, quinolin-4-yl, quinolin-5-yl, quinolin-8-yl, isoquinolin-1-yl, isoquinolin-3-yl, 1,2,3,4-tetrahydro-quinolin-2-yl, 1,2,3,4-tetrahydro-quinolin-3-yl, benzofuran-2-yl, benzofuran-3-yl, benzofuran-5-yl, 1H-indol-5-yl, benzo[b]thiophen-5-yl, benzo[b]thiophen-3-yl, benzo[b]thiophen-2-yl, 3H-benzotriazol-5-yl, 1-methyl-1H-indol-2-yl, 3H-benzimidazol-5-yl, 4-methoxy-quinolin-2-yl, thieno[2,3-b]thiophen-2-yl and the like.

A second embodiment of the heterocyclic ring aspect of R relates to substituted and unsubstituted non aromatic heterocyclic rings, non-limiting examples of which include pyrrolidin-1-yl, piperidin-1-yl, piperidin-4-yl, piperazin-1-yl, and the like.

$R^1$ is a cysteine trap. The cysteine traps of the present invention can be in either the bio-active or the bio-equivalent form.

Without wishing to be limited by theory, the compounds of the present invention are capable of selectively inhibiting the activity of certain cysteine protease enzymes, inter alia, Caspase-1 enzyme (ICE). Although similar, the active sights of the various cysteine proteases are different enough that although the mechanism of interaction between "cysteine traps" and the various cysteine protease enzymes may be roughly equivalent, the combination of a specific cysteine trap, scaffold, and R unit according to the present invention provides enhanced specificity for certain enzymes. Caspace-1, for example, is an enzyme which is capable of acting to release Interleukin-1β which then diffuses out of the cell. Caspase-1 is believed to comprise an active site which comprises the thio (—SH) of a cysteine amino acid associated with at amino acid position 285 of the Caspase-1 enzyme. It is the thio moiety of this cysteine which reacts reversibly or irreversibly with the second reactive moiety of the cysteine traps which comprise the compounds of the present invention. It is therefore believed it is the R unit and 8,6-fused ring scaffold portion of the molecule which aligns the trap in a manner which is favorable to reacting with Caspase-1 enzyme over other cysteine proteases.

As stated herein above, the cysteine traps of the present invention may be reversible or irreversible traps. The following is a non-limiting description of cysteine traps according to the present invention.

Reversible Cysteine Traps

The first category of $R^1$ units are reversible cysteine traps, the first aspect of which relates to cyclic iterations of these traps and the bio-active and bio-equivalent embodiments thereof. These traps are referred to collectively herein as "lactol" cysteine traps whether said traps are in the bio-active form which interacts reversibly with cysteine protease enzymes or in the bio-equivalent form. These lactols have the general formula:

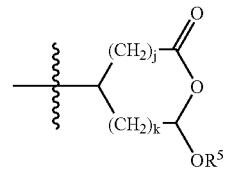

wherein $R^5$ is hydrogen (bioactive form), $C_1$–$C_4$ alkyl, substituted or unsubstituted $C_6$–$C_{10}$ aryl and alkylenearyl, inter alia, phenyl, benzyl (bio-equivalent forms) and the indices j and k are each independently 0, 1, or 2. One iteration of this aspect relates to the aspartate traps, one of which has the following bio-active forms which exist in equilibrium depending upon the medium into which they are dissolved.

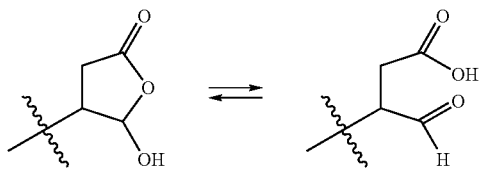

However, the bio-active form is the form which is present when enzyme inhibition occurs whether in vitro or in vivo.

An example of a bio-equivalent form of this trap has the formula:

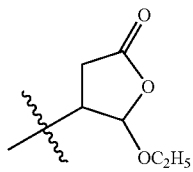

and which must be reverted to the above described bio-active form prior to interaction with the target enzyme.

Non-limiting examples of the bio-active and bio-equivalent forms of suitable cysteine traps which comprise the first aspect of $R^1$ units include:

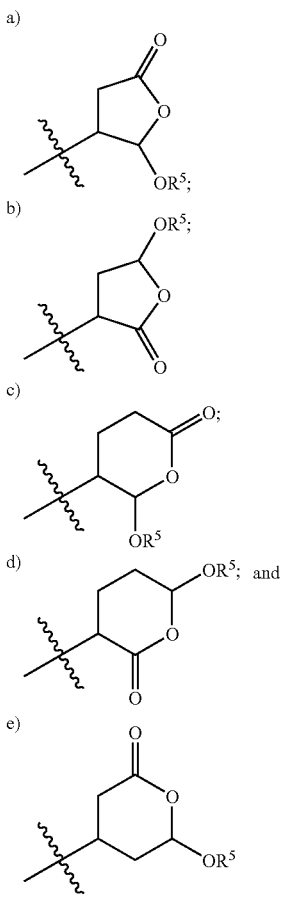

wherein $R^5$ is the same as defined herein above. As described herein below, the bio-equivalent forms of the aspartyl or glutamyl traps can be prepared according to Chapman, K. T. *Bioorganic Med. Chem. Lett.*, 2(6), 1992, pp. 613–618. included herein by reference.

A second aspect of $R^1$ units, which are reversible cysteine traps, relates to open form embodiments of said traps having the formula:

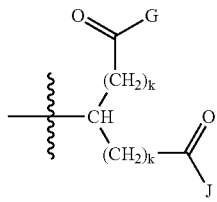

wherein G is —OH or a labile unit and J is a unit selected from the group:
i) hydrogen;
ii) substituted or unsubstituted aryl;
iii) substituted or unsubstituted alkylenearyl;
iv) substituted or unsubstituted heteroaryl;
v) —CH$_2$N(R$^{21}$)$_2$;
vi) —C(O)R$^{21}$;
vii) —C(O)N(R$^{21}$)$_2$; and
viii) —C(O)OR$^{21}$;

$R^{21}$ is hydrogen, substituted or unsubstituted aryl, substituted or unsubstituted alkylenearyl, and substituted or unsubstituted heteroaryl.

The first iteration of this second aspect encompasses reversible cysteine traps, wherein the first reactive moiety (carboxylate unit) comprises a unit having the formula:

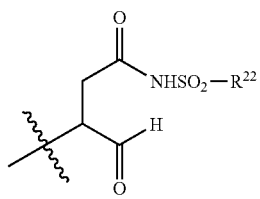

wherein $R^{22}$ is $C_1$–$C_4$ alkyl.

A second iteration of this aspect relates to cysteine traps wherein G is a —OH, said traps having the general formula:

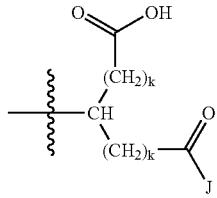

wherein J is an alkylenearyl unit having the formula —(CH$_2$)$_u$R$^{23}$; R$^{23}$ is a substituted or unsubstituted aryl unit, inter alia, phenyl, naphthyl, and the like; the index u is from 0 to 10. Non-limiting examples of suitable J units include alkylenearyl units wherein the index u is selected from the group consisting of 1, 2, 3, 4, and 5: benzyl, 2-phenylethyl, 3-phenylpropyl, 4-phenylbutyl, and 5-phenylpentyl.

A further iteration of this aspect relates to cysteine traps wherein J is an alkylenearyl unit. A non-limiting example of a generic Category II scaffold coupled to a cysteine trap encompassed by this embodiment has the formula:

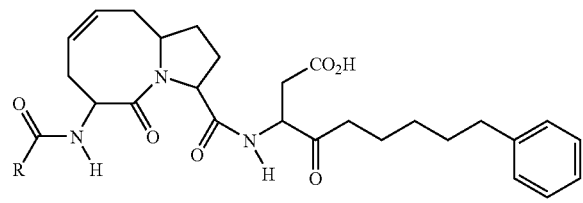

wherein R is the same as defined herein above.

A third aspect of $R^1$ units which are reversible cysteine traps relates to α,α-difluoro ketones having the formula:

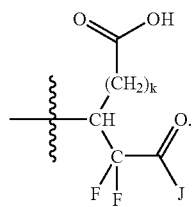

A non-limiting example of a generic Category II scaffold coupled to a α,α-difluoro ketone cysteine trap encompassed by this aspect has the formula:

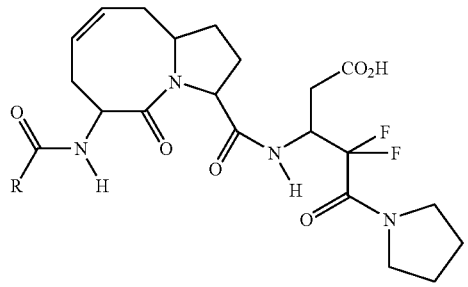

wherein R is the same as defined herein above.

The second category of $R^1$ units encompasses irreversible binding cysteine traps. These traps act in a manner described in and known throughout the prior art as "suicide" binding units because of their irreversible effect in stopping an enzyme from maintaining activity or maturing the release of cytokines. The first aspect of this aspect are carboxy methylene units having the formula:

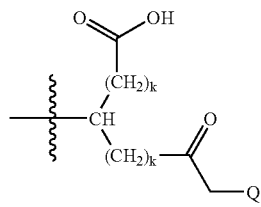

wherein Q is a leaving group selected from:
  i) substituted or unsubstituted heterocyclic or heteroaryl;
  ii) —OC(O)$R^{11}$;
  iii) —NHSO$_2$$R^{12}$;
  iv) —ON$R^{13}$C(O)$R^{13}$;
  v) halogen;
  vi) —NHC(O)O$R^{14}$;
  vii) —NHC(O)NH$R^{15}$;
  ix) —O$R^{16}$;
  x) —S$R^{17}$;
  xi) —SS$R^{18}$;
  xii) —SSO$_3$$R^{19}$; and
  xiii) —OP(O)($R^2$)$_2$;

wherein $R^{11}$ is $C_6$–$C_{10}$ aryl, for example, phenyl, naphtha-1-yl; $C_7$–$C_{20}$ alkylenearyl, for example, benzyl; —NH$R^{24}$; $R^{24}$ is $C_1$–$C_4$ alkyl; $R^{12}$ is $C_1$–$C_{12}$ linear, branched, or cyclic alkyl; $R^{13}$ is hydrogen, $C_1$–$C_4$ alkyl, substituted or unsubstituted $C_6$–$C_{10}$ aryl, substituted or unsubstituted $C_7$–$C_{20}$ alkylenearyl, or two $R^{13}$ units can be taken together to form a fused or no-fused ring having from 3 to 12 atoms; $R^{14}$ is substituted or unsubstituted $C_6$–$C_{10}$ aryl or substituted or unsubstituted $C_7$–$C_{20}$ alkylenearyl; $R^{15}$ is $C_1$–$C_4$ alkyl, substituted or unsubstituted $C_6$–$C_{10}$ aryl, and substituted or unsubstituted $C_7$–$C_{20}$ alkylenearyl; $R^{16}$ is $C_1$–$C_4$ alkyl; $R^{17}$ and $R^{18}$ are substituted or unsubstituted $C_6$–$C_{10}$ aryl, and substituted or unsubstituted $C_7$–$C_{20}$ alkylenearyl; $R^{19}$ is hydrogen, $C_1$–$C_4$ alkyl, substituted or unsubstituted $C_6$–$C_{10}$ aryl, and substituted or unsubstituted $C_7$–$C_{20}$ alkylenearyl; $R^{20}$ is substituted or unsubstituted $C_6$–$C_{10}$ aryl, and substituted or unsubstituted $C_7$–$C_{20}$ alkylenearyl.

The first aspect of this category of irreversible cysteine traps relates to acyloxy ketones having the formula:

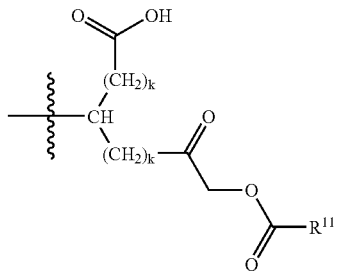

wherein $R^{11}$ is a substituted aryl unit, for example, 2,6-dimethylphenyl, 2,6-dichlorophenyl, and the like; the index k is the same as defined herein above. A non-limiting example of a generic Category I scaffold coupled to a cysteine trap encompassed by this aspect has the formula:

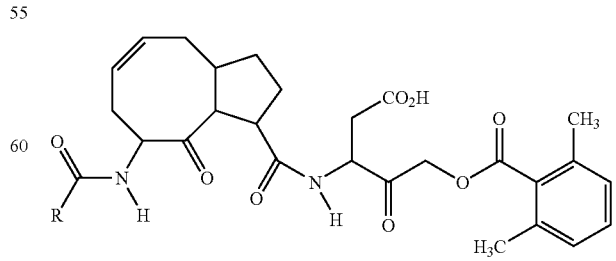

wherein R is the same as defined herein above.

A further aspect relates to cysteine traps wherein J is a unit having the formula —ONR¹³C(O)R¹³ wherein two R¹³ units can be taken together to form a fused ring. A non-limiting example of a generic Category I scaffold coupled to a cysteine trap encompassed by this embodiment has the formula:

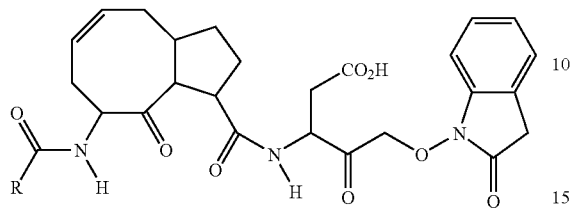

wherein R is the same as defined herein above.

A third aspect of Category II cysteine traps relates to units wherein Q is a substituted or unsubstituted heterocyclic or heteroaryl unit. A non-limiting example of a generic Category I scaffold coupled to a cysteine trap encompassed by this embodiment has the formula:

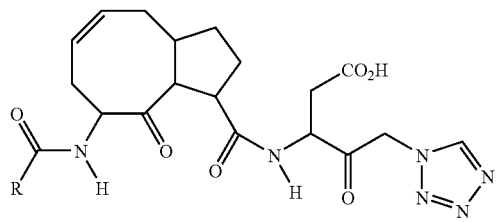

wherein R is the same as defined herein above. Other heteroaryl units include substituted and unsubstituted isoxazolyl, thiazolyl, imidazolyl, benzoxazolyl, and isoxazolinyl. Non-limiting examples include:

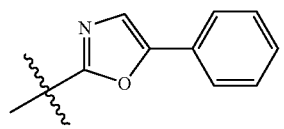

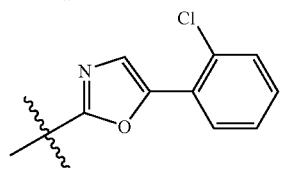

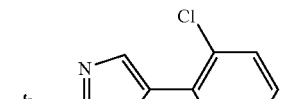

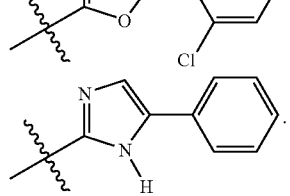

The second aspect of $R^1$ units encompassing irreversible binding cysteine traps are unsaturated compounds having the formula:

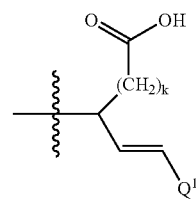

wherein $Q^1$ is a unit having the formula:
i) —C(O)R²⁴;
ii) —C(O)N(R²⁴)₂; or
iii) —C(O)OR²⁴;

the first iteration of which has the formula:

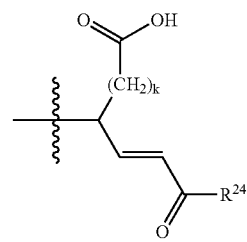

wherein $R^{24}$ is —OR²⁵ or —NHR²⁵ wherein $R^{25}$ is substituted or unsubstituted $C_6$–$C_{10}$ aryl or substituted or unsubstituted $C_7$–$C_{20}$ alkylenearyl. A non-limiting example of a generic Category II scaffold coupled to a cysteine trap encompassed by this iteration of the second aspect of $R^1$ units encompassing irreversible binding cysteine traps has the formula:

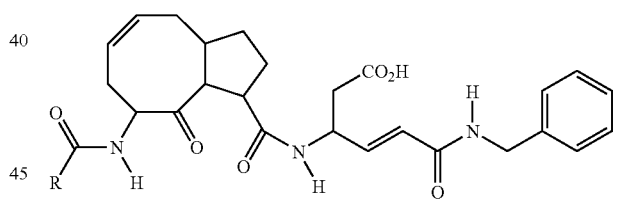

wherein R is the same as defined herein above.

wherein R and X are the same as defined herein above

L and $L^1$ are linking groups which serves to link the R and $R^1$ units respectively to the main [8,5] fused ring scaffold, said linking groups each having the formula:

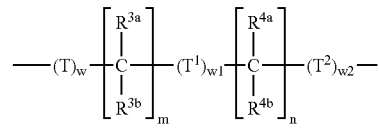

T, $T^1$, and $T^2$ are each independently selected from the group consisting of:
i) —NR⁶—;
ii) —O—;
iii) —NR⁶S(O)₂—;

iv) —S(O)$_2$NR$^6$—; and
v) mixtures thereof;

w, w$^1$, and w$^2$ are each independently 0 or 1.
R$^{3a}$, R$^{3b}$, R$^{4a}$, and R$^{4b}$ are each independently
i) hydrogen;
ii) C$_1$–C$_4$ linear, branched, and cyclic alkyl;
iii) R$^{3a}$ and R$^{3b}$ or R$^{4a}$, and R$^{4b}$ can be taken together to form a carbonyl unit;
iv) two R$^{3a}$ or two R$^{3b}$ units from adjacent units or two R$^{4a}$ or two R$^{4b}$ units from adjacent units can be taken together to form a double bond; and
v) mixtures thereof;

R$^6$ is hydrogen, substituted or unsubstituted C$_1$–C$_{10}$ linear, branched, or cyclic alkyl, C$_6$–C$_{10}$ aryl, C$_7$–C$_{12}$ alkylenearyl, and mixtures thereof; the index m is from 0 to 5; the index n is from 0 to 5; the indices w, w$^1$, and w$^2$ are each independently 0 or 1. Each value of the indices m and n represent a distinct —C(R$^{3a}$R$^{3b}$)— or —C(R$^{4a}$R$^{4b}$)— unit. As described further herein below, a first —C(R$^{3a}$R$^{3b}$)— may define a carbonyl unit in the linking unit while a second —C(R$^{3a}$R$^{3b}$)— unit may be defined as a methylene unit: —CH$_2$—.

Examples of linking units according to the present invention include L units wherein:
i) the indices n, w, and w$^2$ are each equal to 0; w$^1$ is equal to 1, T$^1$ is —NH—, m is equal to 1, R$^{3a}$ and R$^{3b}$ are taken together to form a carbonyl unit, said L unit having the formula:

—C(O)NH—;

ii) the indices m, n, and w are each equal to 0; w$^1$ and w$^2$ are equal to 1, T$^1$ is —SO$_2$— and T$^2$ is equal to —NH—, said L unit having the formula:

—SO$_2$NH—;

iii) the indices w and w$^1$ are each equal to 0; w$^2$ is equal to 1, T$^2$ is —NH—, m and n are each equal to 1, R$^{3a}$ and R$^{3b}$ are taken together to form a carbonyl unit; and R$^{4a}$ and R$^{4b}$ are taken together to form a carbonyl unit, said L unit having the formula:

—C(O)C(O)NH—;

iv) the indices m, n, w and w$^2$ are each equal to 0; w$^1$ is equal to 1, T$^1$ is —NH—, said L unit having the formula:

—NH—;

v) the indices m and w are each equal to 0; w$^1$ and w$^2$ are each equal to 1, T$^1$ and T$^2$ are each —NH—, n is equal to 1, R$^{4a}$ and R$^{4b}$ are taken together to form a carbonyl unit, said L unit having the formula:

—NHC(O)NH—;

vi) the indices m and w are each equal to 0; w$^1$ and w$^2$ are each equal to 1, T$^1$ is equal to —O—; T$^2$ is equal to —NH—, n is equal to 1, R$^{4a}$ and R$^{4b}$ are taken together to form a carbonyl unit, said L unit having the formula:

—OC(O)NH—;

vii) the indices w and w$^1$ are each equal to 0; the index w$^2$ is equal to 1; T$^2$ is equal to —NH—; m is equal to 2, each R$^{3a}$ and R$^{3b}$ unit is hydrogen; n is equal to 1, R$^{4a}$ and R$^{4b}$ are taken together to form a carbonyl unit, said L unit having the formula:

—CH$_2$CH$_2$C(O)NH—;

viii) the indices w and w$^1$ are each equal to 0; the index w$^2$ is equal to 1; T$^2$ is equal to —NH—; m is equal to 2, each R$^{3a}$ unit is hydrogen, R$^{3b}$ from the first unit and R$^{3b}$ from the second unit are taken together to form a double bond; n is equal to 1, R$^{4a}$ and R$^{4b}$ are taken together to form a carbonyl unit, said L unit having the formula:

—CH=CHC(O)NH—.

L$^1$ units are formed in the same manner and can comprise the same or different units than L. For example, when L is —C(O)NH—, the unit L$^1$ can also be —C(O)NH—; L$^1$ can be any compatible unit.

The first aspect of linking units relates to the groups selected from the group consisting of:
i) —C(O)NH—;
ii) —NHC(O)—;
iii) —NHC(O)NH—;
iv) —C(O)C(O)NH—;
v) —C(O)—;
vi) —NH—; or
vii) —SO$_2$NH—.

The first aspect of the linking units relates to compounds comprising L and L$^1$ each equal to —C(O)NH—; for example, scaffolds having the formula:

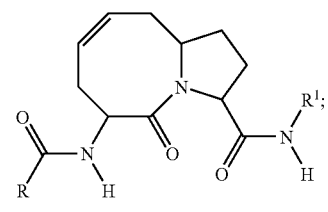

I the second aspect of the linking units relates to compounds comprising L units that are equal to —NHC(O)— and L$^1$ units that are equal to —C(O)NH—; for example, scaffolds having the formula:

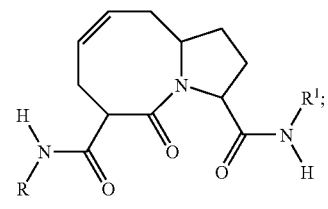

II the third aspect of the linking units relates to compounds comprising L units that are equal to —NHC(O)NH— and L$^1$ units that are equal to —C(O)NH—; for example, scaffolds having the formula:

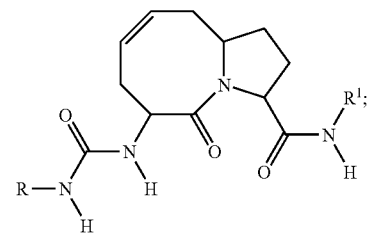

III the fourth aspect of the linking units relates to compounds comprising L units that are equal to —C(O)C(O)NH— and L¹ units that are equal to —C(O)NH—; for example, scaffolds having the formula:

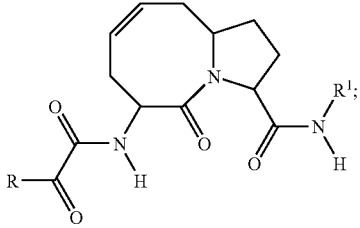

IV the fifth aspect of the linking units relates to compounds comprising L units that are equal to —C(O)— and L¹ units that are equal to —C(O)NH—; for example, scaffolds having the formula:

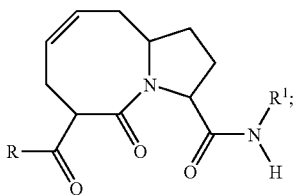

V the sixth aspect of the linking units relates to compounds comprising L units that are equal to —NH— and L¹ units that are equal to —C(O)NH—; for example, scaffolds having the formula:

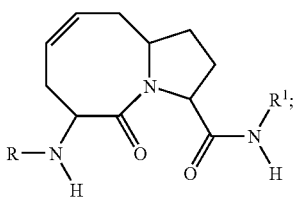

VI the seventh aspect of the linking units relates to compounds comprising L units that are equal to —NHC(O)— and L¹ units that are equal to —C(O)NH—; for example, scaffolds having the formula:

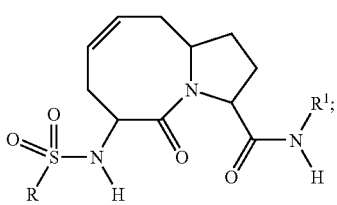

VII the eighth aspect of the linking units relates to compounds comprising L units that are equal to —CH₂CH₂C(O)NH— and L¹ units that are equal to —C(O)NH—; for example, scaffolds having the formula:

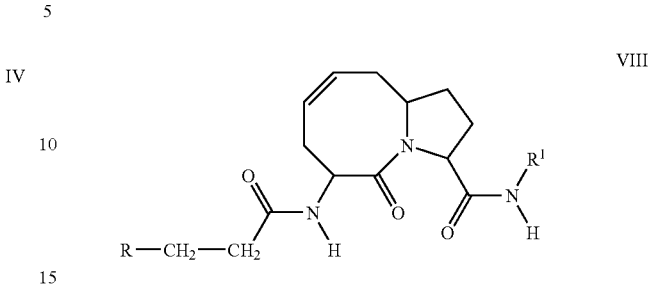

VIII the ninth aspect of the linking units relates to compounds comprising L units that are equal to —CH═CHC(O)NH— and L¹ units that are equal to —C(O)NH—; for example, scaffolds having the formula:

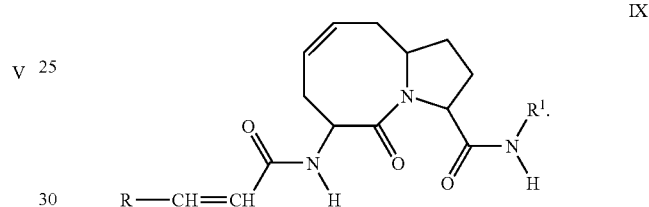

IX

The following are examples of compounds which comprise the iterations I–IX disclosed in the general figures herein above.

Linking unit iteration:
I) 6-[(isoquinoline-1-carbonyl)-amino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide;
II) 6-(Isoquinolin-1-ylcarbamoyl)-5-oxo-1,2,3,5,6,7,10,10a-octahydro-pyrrolo[1,2-a]azocine-3-carboxylic acid 3-[(2-hydroxy-5-oxo-tetrahydro-furan-3-yl)-amide];
III) 6-(3-Isoquinolin-1-yl-ureido-5-oxo-1,2,3,5,6,7,10,10a-octahydro-pyrrolo[1,2-a]azocine-3-carboxylic acid (2-hydroxy-5-oxo-tetrahydro-furan-3-yl)-amide;
IV) 6-(2-Isoquinolin-1-yl-2-oxo-acetylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;
V) 6-(Isoquinoline-1-carbonyl)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;
VI) 6-(Isoquinolin-1-ylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;
VII) 6-(Isoquinoline-1-sulfonylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;
VIII) 6-(3-Isoquinolin-1-yl-propionylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide; and
IX) 6-(3-Isoquinolin-1-yl-acryloylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide.

Examples of compounds utilizing the above described linking units can be found in the appended examples herein below.

The first category of interleukin-1β converting enzyme inhibitors according to the present invention relates to compounds comprising a 3,6-disubstituted 5-oxo-1,2,3,5,6,7,10,10a-octahydro-pyrrolo[1,2-a]azocine scaffold having the formula:

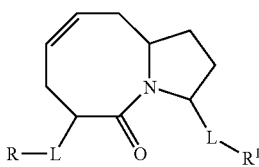

one iteration of which comprises scaffolds having the indicated stereochemistry. Table I relates to non-limiting examples of analogs comprising a first aspect of this category, said analogs having the formula:

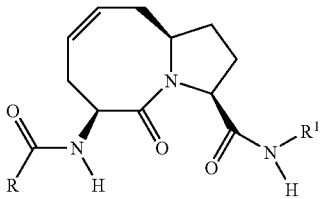

wherein R which is substituted or unsubstituted aryl and R¹ are defined in Table I herein below.

TABLE I

| No. | R | R¹ |
|---|---|---|
| 1 | phenyl | 2-hydroxy-5-oxo-tetrahydrofuran-3-yl |
| 2 | 2-methylphenyl | 2-hydroxy-5-oxo-tetrahydrofuran-3-yl |
| 3 | 3-methylphenyl | 2-hydroxy-5-oxo-tetrahydrofuran-3-yl |
| 4 | 4-methylphenyl | 2-hydroxy-5-oxo-tetrahydrofuran-3-yl |
| 5 | 2-fluorophenyl | 2-hydroxy-5-oxo-tetrahydrofuran-3-yl |
| 6 | 3-fluorophenyl | 2-hydroxy-5-oxo-tetrahydrofuran-3-yl |
| 7 | 4-fluorophenyl | 2-hydroxy-5-oxo-tetrahydrofuran-3-yl |
| 8 | 2-chlorophenyl | 2-hydroxy-5-oxo-tetrahydrofuran-3-yl |
| 9 | 3-chlorophenyl | 2-hydroxy-5-oxo-tetrahydrofuran-3-yl |
| 10 | 4-chlorophenyl | 2-hydroxy-5-oxo-tetrahydrofuran-3-yl |
| 11 | 2-methoxyphenyl | 2-hydroxy-5-oxo-tetrahydrofuran-3-yl |
| 12 | 3-methoxyphenyl | 2-hydroxy-5-oxo-tetrahydrofuran-3-yl |
| 13 | 4-methoxyphenyl | 2-hydroxy-5-oxo-tetrahydrofuran-3-yl |
| 14 | 2-trifluoromethylphenyl | 2-hydroxy-5-oxo-tetrahydrofuran-3-yl |
| 15 | 3-trifluoromethylphenyl | 2-hydroxy-5-oxo-tetrahydrofuran-3-yl |
| 16 | 4-trifluoromethylphenyl | 2-hydroxy-5-oxo-tetrahydrofuran-3-yl |
| 17 | 3,4,5-trimethoxyphenyl | 2-hydroxy-5-oxo-tetrahydrofuran-3-yl |
| 18 | benzoyl | 2-hydroxy-5-oxo-tetrahydrofuran-3-yl |
| 19 | phenylamino | 2-hydroxy-5-oxo-tetrahydrofuran-3-yl |
| 20 | 2-phenylethyl | 2-hydroxy-5-oxo-tetrahydrofuran-3-yl |
| 21 | naphth-1-yl | 2-hydroxy-5-oxo-tetrahydrofuran-3-yl |
| 22 | naphth-2-yl | 2-hydroxy-5-oxo-tetrahydrofuran-3-yl |
| 23 | phenyl | 2-ethoxy-5-oxo-tetrahydrofuran-3-yl |
| 24 | 2-methylphenyl | 2-ethoxy-5-oxo-tetrahydrofuran-3-yl |
| 25 | 3-methylphenyl | 2-ethoxy-5-oxo-tetrahydrofuran-3-yl |
| 26 | 4-methylphenyl | 2-ethoxy-5-oxo-tetrahydrofuran-3-yl |
| 27 | 2-fluorophenyl | 2-ethoxy-5-oxo-tetrahydrofuran-3-yl |
| 28 | 3-fluorophenyl | 2-ethoxy-5-oxo-tetrahydrofuran-3-yl |
| 29 | 4-fluorophenyl | 2-ethoxy-5-oxo-tetrahydrofuran-3-yl |
| 30 | 2-chlorophenyl | 2-ethoxy-5-oxo-tetrahydrofuran-3-yl |
| 31 | 3-chlorophenyl | 2-ethoxy-5-oxo-tetrahydrofuran-3-yl |
| 32 | 4-chlorophenyl | 2-ethoxy-5-oxo-tetrahydrofuran-3-yl |
| 33 | 2-methoxyphenyl | 2-ethoxy-5-oxo-tetrahydrofuran-3-yl |
| 34 | 3-methoxyphenyl | 2-ethoxy-5-oxo-tetrahydrofuran-3-yl |
| 35 | 4-methoxyphenyl | 2-ethoxy-5-oxo-tetrahydrofuran-3-yl |
| 36 | 2-trifluoromethylphenyl | 2-ethoxy-5-oxo-tetrahydrofuran-3-yl |
| 37 | 3-trifluoromethylphenyl | 2-ethoxy-5-oxo-tetrahydrofuran-3-yl |
| 38 | 4-trifluoromethylphenyl | 2-ethoxy-5-oxo-tetrahydrofuran-3-yl |
| 39 | 3,4,5-trimethoxyphenyl | 2-ethoxy-5-oxo-tetrahydrofuran-3-yl |
| 40 | benzoyl | 2-ethoxy-5-oxo-tetrahydrofuran-3-yl |
| 41 | phenylamino | 2-ethoxy-5-oxo-tetrahydrofuran-3-yl |
| 42 | 2-phenylethyl | 2-ethoxy-5-oxo-tetrahydrofuran-3-yl |
| 43 | naphth-1-yl | 2-ethoxy-5-oxo-tetrahydrofuran-3-yl |
| 44 | naphth-2-yl | 2-ethoxy-5-oxo-tetrahydrofuran-3-yl |

The compounds of this category can be suitably prepared by the procedure outlined herein below, utilizing intermediates 8 and 9 (Type I Intermediates) which can be synthesized by the procedure outlined in Scheme I.

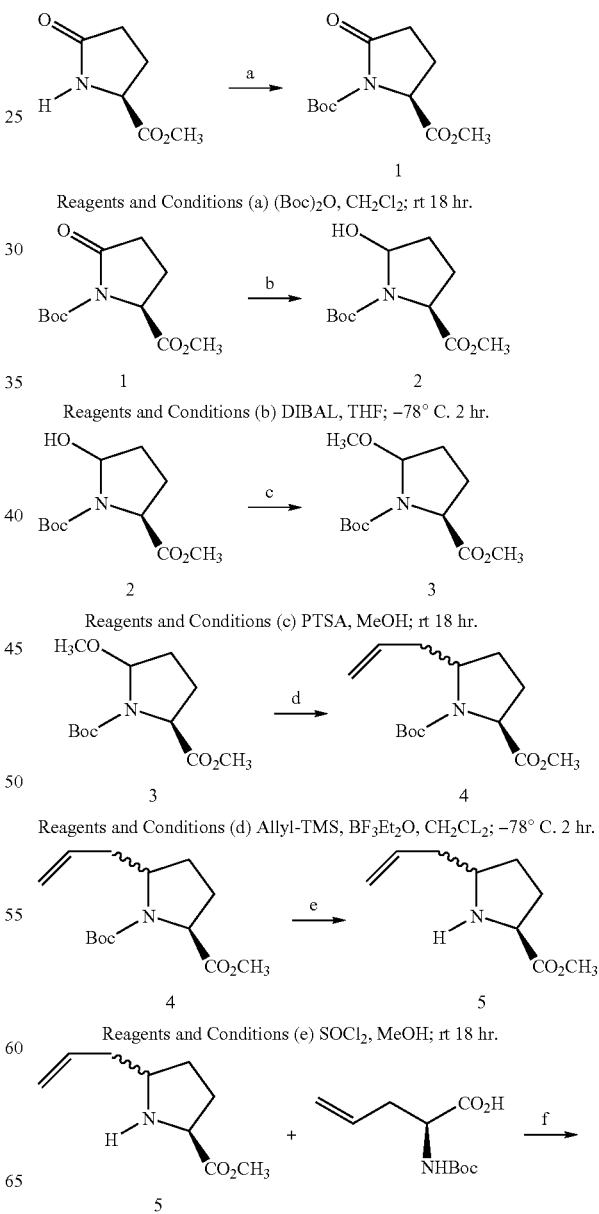

Scheme I
General Scheme for Intermediate Type I

Reagents and Conditions (a) (Boc)₂O, CH₂Cl₂; rt 18 hr.

Reagents and Conditions (b) DIBAL, THF; −78° C. 2 hr.

Reagents and Conditions (c) PTSA, MeOH; rt 18 hr.

Reagents and Conditions (d) Allyl-TMS, BF₃Et₂O, CH₂CL₂; −78° C. 2 hr.

Reagents and Conditions (e) SOCl₂, MeOH; rt 18 hr.

-continued

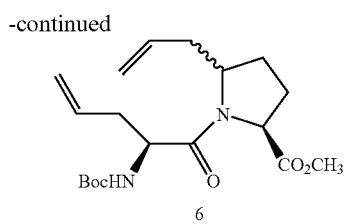

6

Reagents and Conditions (f) DCC, TEA, DMAP, CH₂Cl₂; rt 18 hr.

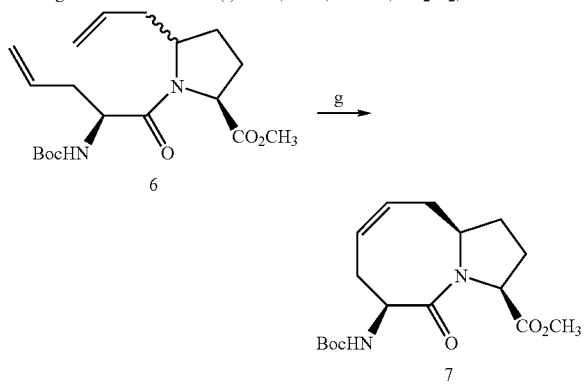

Reagents and Conditions (g) Grubbs' cat., CH₂Cl₂; reflux 4 hr.

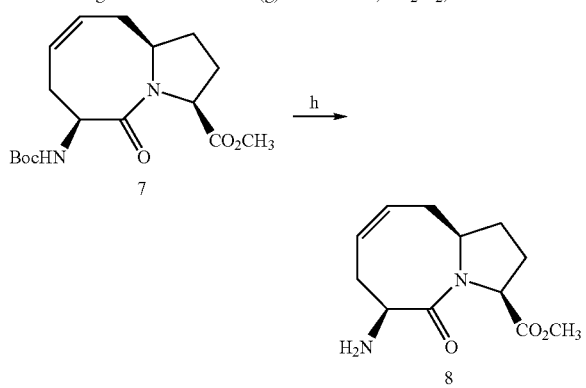

Reagents and Conditions (h) TFA, CH₂Cl₂; rt 2 hr.

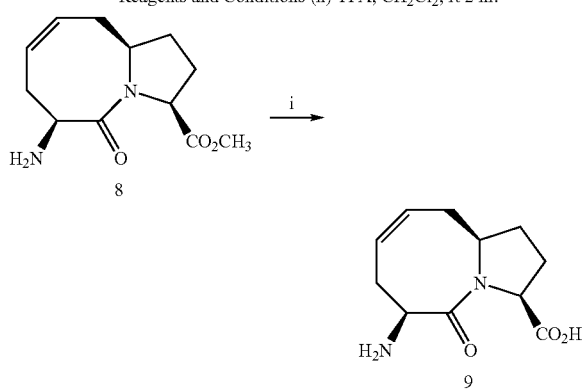

Reagents and Conditions (i) LiOH, THF/H₂O; rt 18 hr.

Preparation of 5-oxo-pyrrolidine-1,2-dicarboxylic acid 1-tert-butyl ester 2-methyl ester (1): To a solution of 5-oxo-pyrrolidine-2-carboxylic acid methyl ester (5.0 g, 35 mmol), 4-dimethylaminopyridine (0.43 g, 3.5 mmol), and triethylamine (12 mL, 8.8 g, 88 mmol) in CH₂Cl₂ (100 mL), di-t-butyldicarbonate (15.2 g, 70 mmol) is added. After the consumption of the starting material, the reaction is washed with H₂O (2×100 mL), and brine (1×100 mL). The CH₂Cl₂ is reduced under in vacuo. The residue is purfied over silica (hexanes/ethyl acetate 60:40) to afford 7.95 g of the desired product as a light yellow oil (94% yield). $^1$H-NMR (300 MHz, CDCl₃): δ 4.67–4.63 (dd, J=9.6, 3.3, 1H), 3.82 (s, 3H), 2.73–2.29 (m, 3H), 2.12–2.02 (m, 1H); MS (ESI): m/e=244.06 (M+H).

Preparation of 5-hydroxy-pyrrolidine-1,2-dicarboxylic acid 1-tert-butyl ester 2-methyl ester (2): To a solution of 5-oxo-pyrrolidine-1,2-dicarboxylic acid 1-tert-butyl ester 2-methyl ester, 1, (7.95 g, 32.7 mmol) in THF (65 mL) at −78° C., neat DIBAL-H (12.8 mL, 8.97 g, 63.1 mmol) dissolved in THF (25 mL) is added dropwise. After the consumption of the starting material, the reaction is cautiously quenched with isopropanol (5 mL), potassium sodium tartrate (26 g, 124 mmol) in H₂O (160 mL). The resultant slurry is taken up in ether (200 mL) and then extracted with ether (5×250 mL). The ether layers are combined, washed with brine (1×250 mL), dried with MgSO₄, and concentrated in vacuo to afford 6.8 g (85% yield) of the desired product as a clear oil which is used without further purification. MS (ESI): m/e=268.03 (M+Na).

Preparation of 5-methoxy-pyrrolidine-1,2-dicarboxylic acid 1-tert-butyl ester 2-methyl ester (3): To a solution of 5-hydroxy-pyrrolidine-1,2-dicarboxylic acid 1-tert-butyl ester 2-methyl ester, 2, (48.1 g, 196 mmol) in methanol (500 mL), is added p-toluenesulfonic acid (1.0 g, 5.8 mmol). Once consumption of the starting material is complete, the solvent is removed under in vacuo and the residue purified over silica (hexanes/ethyl acetate 75:25) to afford 42 g (83% yield) of the desired product as a clear oil. $^1$H-NMR (300 MHz, CDCl₃): δ 5.334–5.142 (m, 1H), 4.36–4.24 (m, 1H), 3.75–3.72 (m, 3H), 3.44–3.36 (m, 3H), 2.45–1.71 (m, 4H), 1.51–1.42 (m, 9H); $^{13}$C-NMR (75.5 MHz, CDCl₃): δ 200.16, 199.70, 173.31, 172.99, 154.28, 154.13, 153.98, 89.37, 89.27, 88.62, 88.41, 81.27, 81.04, 80.75, 80.54, 59.65, 59.33, 58.97, 58.84, 56.38, 56.14, 55.92, 55.79, 55.38, 55.00, 52.07, 51.99, 32.95, 32.29, 31.79, 31.14, 30.20, 28.35, 28.17, 27.11, 24.86, 21.06, 14.29; MS (ESI): m/e=282.07 (M+Na).

Preparation of 5-allyloxy-pyrrolidine-1,2-dicarboxylic acid 1-tert-butyl ester 2-methyl ester (4): To a solution of 5-methoxy-pyrrolidine-1,2-dicarboxylic acid 1-tert-butyl ester 2-methyl ester, 3, (9.86 g, 38.0 mmol) and allyltrimethylsilane (13.0 g, 114 mmol) in CH₂Cl₂ (200 mL) at −78° C. is added dropwise boron trifluoride etherate (4.82 mL, 38.0 mmol). Once consumption of the starting material is complete, water is cautiously added to quench the reaction. The resulting solution is taken up in ethyl acetate (200 mL) washed with water (1×250 mL), brine (1×250 mL), and dried with Na₂SO₄. The organics are concentrated in vacuo. The resulting residue is purified over silica (hexanes/ethyl acetate 85:15) to afford 6.2 g (61% yield) of the desired product as a light yellow oil. $^1$H-NMR (300 MHz, CDCl₃): δ 5.85–5.70 (m, 1H), 5.09–5.00 (m, 2H), 4.31–4.16 (m, 1H), 3.95–3.76 (br m, 1H), 3.71–3.69 (m, 3H), 2.72–2.57 (br m, 1H), 2.24–1.69 (m, 5H), 1.45–1.38 (m, 9H); MS (ESI): m/e=270.11 (M+H).

Preparation of 5-allyloxy-pyrrolidine-2-carboxylic acid methyl ester hydrochloride (5): To a solution of 5-allyloxy-pyrrolidine-1,2-dicarboxylic acid 1-tert-butyl ester 2-methyl ester, 4, (7.28 g, 27 mmol) in MeOH is added thionyl chloride (4 mL, 54 mmol). The solution is stirred overnight and the solvent removed in vacuo to afford 4.25 g (95% yield) of the desired product as a dark yellow crystal. $^1$H-NMR (300 MHz, CDCl₃): δ 11.47 (s, 1H), 8.15 (s, 1H), 5.81 (m, 1H), 5.23 (m, 2H), 4.55 (s, 1H), 3.85 (s, 3H), 2.88

(m, 1H), 2.59–2.42 (m, 2H), 2.24 (m, 1H), 1.81 (m, 1H). $^{13}$C-NMR (75.5 MHz, CDCl$_3$): δ 170.0, 132.7, 132.3, 120.2, 119.6, 60.6, 60.2, 59.4, 58.9, 53.9, 36.6, 29.5, 29.2, 28.3. ESI MS 170.13 (M+H).

Preparation of 5-allyl-1-(2-tert-butoxycarbonylamino-pent-4-enoyl)-pyrrolidine-2-carboxylic acid methyl ester (6): To a solution of 5-allyloxy-pyrrolidine-2-carboxylic acid methyl ester hydrochloride, 5, (17.82 g, 86.6 mmol) and triethylamine (36 mL, 260 mmol) in CH$_2$Cl$_2$ (500 mL), 2-tert-butoxycarbonylamino-pent-4-enoic acid (41.1 g, 191 mmol), 1,3-dicyclohexylcarbodiimide (46.4 g, 225 mmol), and 4-dimethylaminopyridine (21.1 g, 173 mmol) are added. Once consumption of the starting material is complete, the precipitate that forms is filtered from the reaction mixture. The CH$_2$Cl$_2$ is reduced in vacuo and residue which remains is diluted with ether (500 mL). A white precipitate forms which is collected by filtration. The solvent is then removed and the resulting residue dissolved in ethyl acetate (250 mL) then further diluted with hexanes (250 mL). A white precipitate again forms and is removed. The solution which remains is concentrate in vacuo and the residue purified over silica (hexanes/ethyl acetate 80:20) to afford 27.69 g (87% yield) of the desired product as a slightly yellow oil. $^1$H-NMR (300 MHz, CDCl$_3$): δ 5.91–5.74 (m, 2H), 5.22–5.01 (m, 5H), 4.55–4.40 (m, 3H), 3.81–3.74 (m, 3H), 2.60–1.90 (m, 4H), 1.45 (s, 9H); $^{13}$C-NMR (75.5 MHz, CDCl$_3$): δ 183.85, 172.92, 172.52, 171.69, 155.58, 135.05, 134.27, 133.45, 118.63, 117.43, 80.00, 60.00, 59.58, 58.47, 52.41, 52.41, 52.10, 51.20, 39.69, 38.09, 29.82, 28.54, 27.11; MS (ESI): m/e=367.21 (M+H).

Preparation of (3S,6S,10aS)-6-tert-butoxycarbonylamino-5-oxo-1,2,3,5,6,7,10,10a-octahydro-pyrrolo[1,2-a]azocine-3-carboxylic acid methyl ester (7): 5-Allyl-1-(2-tert-butoxycarbonylamino-pent-4-enoyl)-pyrrolidine-2-carboxylic acid methyl ester, 6, (3.2 g, 8.7 mmol) is dissolved in dichloromethane (40 mL). Grubbs catalyst (0.7 g, 0.85 mmol) is added and the mixture heated to reflux for 4 hours. The reaction is allowed to cool and methylsulfoxide (2 mL) is added. After 2 hours the solution is reduced to a oil, which is purified over silica (50% ethyl acetate hexane) to afford 1.76 g (60% yield) of the desired product as a dark yellow oil. $^1$H-NMR (300 MHz, CDCl$_3$): δ 5.79 (m, 2H), 5.61 (d, J=6.9, 1H), 4.89 (dd, J=15, 7.2, 5.79 (m, 2H), 5.61 (d, J=6.9, 1H), 4.89 (dd, J=15, 7.2, 5.79 (m, 2H), 5.61 (d, J=6.9, 1H), 4.89 (dd, J=15, 7.2, 1H), 4.54 (m, 1H), 4.15 (m, 1H), 3.75 (s, 3H), 2.81 (m, 2H) 2.49–1.98 (m, 6H), 1.47 (s, 9H). $^{13}$C NMR (CDCl$_3$): □ 172.6, 171.3, 155.4, 129.4, 126.0, 79.9, 60.3, 58.9, 52.2, 52.1, 35.5, 33.2, 33.1, 28.6, 27.4. ESI MS: 339.18 (M+H).

Preparation of (3S,6S,10aS)-6-amino-5-oxo-1,2,3,5,6,7,10,10a-octahydro-pyrrolo[1,2-a]azocine-3-carboxylic acid methyl ester (8): 6-tert-butoxycarbonylamino-5-oxo-1,2,3,5,6,7,10,10a-octahydro-pyrrolo[1,2-a]azocine-3-carboxylic acid methyl ester, 7, (3.46 g, 10.2 mmol) is treated with a solution of 1:1 trifluoroacetic acid/CH$_2$Cl$_2$ (50 mL) and allowed to stir for 2 hours at room temperature after which the solution is concentrated in vacuo and the resulting residue purified over silica (5% methanol/methylene chloride) to afford 2.43 g (100% yield) of the desired product as dark orange crystals. $^1$H NMR (CDCl$_3$): δ 8.11 (bs, 2H), 5.76 (m, 2H), 4.66 (dd, J=9.3, 6.0 Hz, 1H), 4.50 (dd, J=8.7, 3.6, 1H), 4.21 (m, 1H), 3.68 (s, 3H), 2.95 (m, 1H), 2.73 (dt, J=15.3, 6.0, 1H), 2.43 (m, 2H), 2.15 (m, 2H), 1.94 (m, 2H). $^{13}$C NMR (CDCl$_3$): δ 172.3, 168.5, 127.1, 60.7, 58.7, 52.3, 51.9, 32.7, 32.6, 31.2, 27.3. ESI MS 239.12 (M+H).

Preparation of (3S,6S,10aS)-6-amino-5-oxo-1,2,3,5,6,7,10,10a-octahydro-pyrrolo[1,2-a]azocine-3-carboxylic acid (9): To a solution of 6-amino-5-oxo-1,2,3,5,6,7,10,10a-octahydro-pyrrolo[1,2-a]azocine-3-carboxylic acid methyl ester, 8, (1.4 g, 5.2 mmol) in THF/water (3:1) is added LiOH (1.1 eq) and the solution is stirred overnight. The reaction is treated with 1 N HCl to pH 4. The mixture is then frozen and lyophilized to a pale yellow powder, which can be used directly in the next step.

Scheme II is an example of the preparation of an interleukin-1β converting enzyme inhibitor of the first aspect of Category I beginning with intermediate 9.

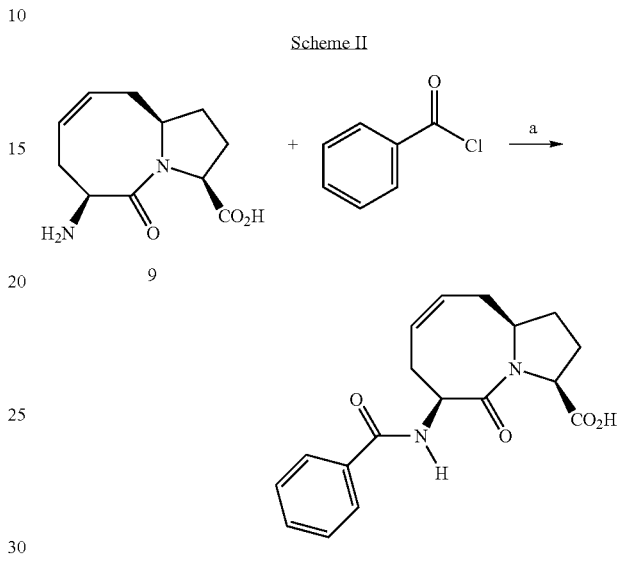

Reagents and Conditions (a) NaHCO$_3$, THF/H$_2$O; rt 18 hr.

Reagents and Conditions (b) (Ph$_3$P)$_4$Pd, HOBt, EDCl, H$^+$; CH$_2$Cl$_2$; rt 6 hr.

EXAMPLE 1

(3S,6S10aS)-6-Benzoylamino-5-oxo-1,2,3,5,6,7,10,10a-octahydro-pyrrolo[1,2-a]azocine-3-carboxylic acid (2-hydroxy-5-oxo-tetrahydro-furan-3-yl)-amide (11)

Preparation of (3S,6S,10aS)-6-benzoylamino-5-oxo-1,2,3,5,6,7,10,10a-octahydro-pyrrolo[1,2-a]azocine-3-carboxylic acid (10): A solution of 6-amino-5-oxo-1,2,3,5,6,7,10,10a-octahydro-pyrrolo[1,2-a]azocine-3-carboxylic acid, 9, (5.6 g, 25 mmol) in 70 mL of H₂O/THF solution is then treated with sodium bicarbonate (2.3 g, 27.4 mmol) and benzoyl chloride (3 ml, 25.84 mmol). The reaction is stirred for 18 hours and then ether (100 mL) is added. The organics are washed two times with 1 N HCl, once with water, and dried over MgSO₄, filtered, and concentrated in vacuo to a residue which is purified over silica to afford the desired compound which is used without further purification.

Preparation of (3S,6S,10aS)-6-benzoylamino-5-oxo-1,2,3,5,6,7,10,10a-octahydro-pyrrolo[1,2-a]azocine-3-carboxylic acid (2-hydroxy-5-oxo-tetrahydro-furan-3-yl)-amide (11) To a solution of (2-ethoxy-5-oxo-tetrahydro-furan-3-yl)-carbamic acid allyl ester (183 mg, 0.8 mmol) (prepared according to Chapman, K. T. *Bioorganic Med. Chem. Lett.*, 2(6), 1992, pp. 613–618) in dichloromethane (6 mL) is added barbituric acid (300 mg, 1.9 mmol) and tetrakistriphenyl phosphine palladium (92 mg, 0.08 mmol). The solution is stirred for 10 minutes and 6-benzoylamino-5-oxo-1,2,3,5,6,7,10,10a-octahydro-pyrrolo[1,2-a]azocine-3-carboxylic acid, 10, (105 mg, 0.32 mmol) is added followed by 1-hydroxybenzotriazole (99 mg, ) 0.74 mmol) and 1-(3-dimethyl-aminopropyl)-3-ethyl-carbodiimide hydrochloride (141 mg, 0.74 mmol). The solution is stirred for 6 hours. Water is added and the organics are washed with NaHSO₄, brine, NaHCO₃, and water. The organic layers are dried with MgSO₄ and concentrated under reduced pressure. The residue is purified over silica to afford the desired product. ¹H NMR (CDCl₃): δ 7.83 (d, J=7.3, 2H), 7.54–7.41 (m, 4H), 5.89–5.71 (m, 2H), 5.49 (dt, J=13.9, 7.0 Hz, 1H), 4.61 (m, 2H), 4.33 (m, 1H), 2.99 (m, 3H), 2.41 (m, 3H), 2.18 (m, 2H), 2.06–1.91 (m, 2H). ¹³C NMR (CDCl₃): δ 176.2, 172.9, 171.6, 167.5, 133.4, 132.3, 131.0, 128.8, 127.6, 125.9, 61.7, 59.0, 50.7, 33.9, 33.4, 32.2, 27.0, 20.9. ESI MS 428.01 (M+H).

The 2-ethoxy-5-oxo-tetrahydrofuran-3-yl cysteine trap can be converted to the 2-hydroxy-5-oxo-tetrahydrofuran-3-yl cysteine trap by the procedure outlined in Scheme III herein below.

Scheme III

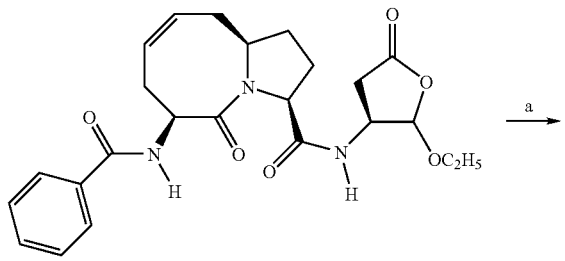

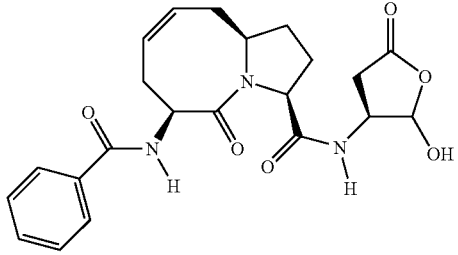

Reagents and Conditions (a) TFA, H₂O/acetonitrile; rt 2 hr.

EXAMPLE 2

(3S,6S,10aS)-6-Benzoylamino-5-oxo-1,2,3,5,6,7,10,10a-octahydro-pyrrolo[1,2-a]azocine-3-carboxylic acid (2-hydroxy-5-oxo-tetrahydrofuran-3-yl)-amide (12)

Preparation of (3S,6S,10aS)-6-Benzoylamino-5-oxo-1,2,3,5,6,7,10,10a-octahydro-pyrrolo[1,2-a]azocine-3-carboxylic acid (2-hydroxy-5-oxo-tetrahydrofuran-3-yl)-amide (12): 6-Benzoylamino-5-oxo-1,2,3,5,6,7,10,10a-octahydro-pyrrolo[1,2-a]azocine-3-carboxylic acid (2-hydroxy-5-oxo-tetrahydro-furan-3-yl)-amide, 11, (47 mg, 0.1 mmol) of the oil obtained above is dissolved in dichloromethane and treated with trifluoroacetic acid (5 mL) and water (1 mL) and stirred for 2 hours after which the solvent is remove in vacuo. The residue is purified over silica to afford the desired product as a white powder. ¹H NMR (CDCl₃): δ 7.37–7.25 (m, 5H), 5.74 (m, 2H), 5.45–5.39 (m, 1H), 5.27 (m, 1H), 4.42 (m, 2H), 4.30 (m, 2H), 3.88–3.79 (m, 1H), 3.74–3.62 (m, 2H), 3.11–2.98 (m, 2H), 2.57–1.97 (m, 9H), 1.84–1.77 (m, 1H), 1.25 (m, 3H). ¹³C NMR (CDCl₃): δ 175.8, 173.4, 170.8, 169.8, 138.5, 130.4, 128.4, 127.5, 127.2, 127.1, 125.8, 125.7, 107.8, 107.6, 65.3, 62.6, 56.4, 56.2, 52.2, 52.1, 43.1, 34.2, 32.8, 32.5, 31.6, 29.0, 26.0, 14.1. ESI MS 470.18 (M+H).

Other examples of this category include the following compounds with the indicated stereochemistry.

(3S,6R,10aR)-6-(3-Methoxybenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide: ¹H NMR (CDCl₃): δ7.34 (m, 4H), 7.05 (m, 1H), 6.03–5.46 (m, 4H), 4.61 (m, 2H), 4.31 (m, 2H), 3.83 (s,3H), 2.98 (m, 4H), 2.35 (m, 2H), 2.16 (m, 2H), 1.97 (m, 2H). ESI MS 458.08 (M+H).

(3S,6S,10aS)-6-(2-Chlorobenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide; ¹H NMR (CDCl₃): δ 7.36 (s, 2H), 7.16–7.04 (m, 3H), 5.64–5.42 (m, 3H), 5.27 (m, 1H), 4.39 (s, 2H), 4.08 (s, 2H), 2.81 (m, 3H), 2.57 (m, 2H), 2.21–1.96 (m, 4H), 1.84–1.79 (m, 3H). ESI MS: 461.98 (M+H).

(3S,6S,10aS)-6-(3-Chlorobenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide; ¹H NMR (CDCl₃): δ 7.79 (s,1H), 7.65 (m, 1H), 7.48 (d, J=8.4 Hz, 1H), 7.73 (m, 2H), 5.87–5.68 (m, 3H), 5.49 (m, 1H), 4.66 (m, 2H), 4.34 (m, 2H), 3.02 (m, 3H), 2.42 (dd, J=14.7, 8.1 Hz, 2H), 2.33–2.19 (m, 3H), 2.0–1.91 (m, 1H). ESI MS 461.97 (M+H).

(3S,6S,10aS)-6-(4-Chlorobenzoylamino)-5-oxo-1,2,3,5, 6,7,10,10a-octahydro-pyrrolo[1,2-a]azocine-3-carboxylic acid (2-hydroxy-5-oxo-tetrahydro-furan-3-yl)-amide; $^1$H NMR (CDCl$_3$): δ 7.76 (d, J=8.4 Hz, 2H), 7.41 (d, J=8.1 Hz, 2H), 7.34 (s, 1H), 6.39 (bs, 1H), 5.87–5.66 (m, 3H), 5.48 (m, 1H), 4.66–4.56 (m, 2H), 4.41–4.32 (m, 2H), 3.01 (m, 3H), 2.44–2.19 (m, 4H), 1.95 (m, 1H). ESI MS: 461.98 (M+H).

(3S,6S,10aS)-6-(2-Methoxybenzoylamino)-5-oxo-1,2,3, 5,6,7,10,10a-octahydro-pyrrolo[1,2-a]azocine-3-carboxylic acid (2-hydroxy-5-oxo-tetrahydro-furan-3-yl)-amide; $^1$H NMR (CDCl$_3$): δ 8.84 (d, J=6.6 Hz, 1H), 8.15 (d, 7.5 Hz, 1H), 7.48 (m, 1H), 7.08 (m, 1H), 6.99 (d, J=8.4 HZ, 1H), 5.98–5.36 (m, 4H), 4.66 (m, 1H), 4.27 (m, 1H), 4.01 (s, 3H), 3.05 (m, 3H), 2.36–1.79 (m, 6H). ESI MS: 458.04 (M+H).

(3S,6S,10aS)-6-(3-Methoxybenzoylamino)-5-oxo-1,2,3, 5,6,7,10,10a-octahydro-pyrrolo[1,2-a]azocine-3-carboxylic acid (2-hydroxy-5-oxo-tetrahydro-furan-3-yl)-amide; $^1$H NMR (CDCl$_3$): δ 7.65 (s, 1H), 7.34 (m, 4H), 7.03 (m, 2H), 5.76 (m, 3H), 5.46 (m, 1H), 4.62 (m, 2H), 4.31 (m, 2H), 3.82 (s, 3H), 2.97 (m, 3H), 2.38 (m, 2H), 2.16 (m, 2H), 2.00 (m, 2H). ESI MS 458.08 (M+H).

(3S,6S,10aS)-6-(4-Methoxybenzoylamino)-5-oxo-1,2,3, 5,6,7,10,10a-octahydro-pyrrolo[1,2-a]azocine-3-carboxylic acid (2-hydroxy-5-oxo-tetrahydro-furan-3-yl)-amide; $^1$H NMR (CDCl$_3$): δ 7.80 (d, J=8.7 Hz, 2H), 7.37 (d, J=21.0 Hz, 1H), 6.91 (d, J=8.7 Hz, 2H), 5.86–5.67 (m, 3H), 5.46 (m, 1H), 4.63 (m, 2H), 4.31 (m, 2H), 3.85 (m, 3H), 2.99 (m, 3H), 2.39 (dd, J=15.0, 7.8 Hz, 2H), 2.28–2.16 (m, 2H), 2.04–1.85 (m, 2H). ESI MS 458.04 (M+H).

(3S,6S,10aS)-6-[(3,4,5-Trimethoxy)benzoylamino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide $^1$H NMR (CD$_3$OD): δ 7.26 (m, 2H), 6.02 (m, 1H), 5.89 (m, 1H), 5.41 (dd, J=12.0, 6.6 Hz, 1H), 4.55–4.28 (m, 4H), 3.92 (m, 9H), 3.81 (m, 1H), 3.35 (m, 2H), 3.08 (m, 1H), 2.91 (m, 1H), 2.75 (m, 1H), 2.61 (m, 1H), 2.44 (m, 1H), 2.34 (m, 1H), 2.13 (m, 4H); ESI MS 518.13 (M+H).

(3S,6S,10aS)-6-[(Naphthalene-2-carbonyl)-amino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide: $^1$H NMR (CDCl$_3$): δ 8.34 (s, 1H), 7.93–7.83 (m, 4H), 7.66–7.51 (m, 3H), 7.42 (s, 1H), 5.90–5.70 (m, 2H), 5.53 (m, 1H), 4.59 (m, 2H), 4.28 (m, 1H), 2.96 (m, 3H), 2.38 (m, 2H), 2.15 (m, 2H), 2.02–1.79 (m, 3H). $^{13}$C NMR (CDCl$_3$): δ 176.1, 173.1, 171.6, 167.8, 135.3, 132.9, 130.6, 129.5, 128.8, 128.5, 128.3, 128.1, 127.2, 125.9, 124.0, 61.9, 59.1, 50.9, 33.9, 33.5, 32.3, 27.1, 21.1. FAB HRMS: (m/z) 478.1981 (found), 478.1978 (calc) 0.6 ppm.

(3S,6S,10aS)-6-(2-Methyl-benzoylamino)-5-oxo-1,2,3,5, 6,7,10,10a-octahydro-pyrrolo[1,2-a]azocine-3-carboxylic acid (2-hydroxy-5-oxo-tetrahydro-furan-3-yl)-amide; $^1$H NMR (CDCl$_3$): δ 7.39–7.30 (m, 3H), 7.22–7.17 (m, 1H), 5.86 (m, 1H), 5.71 (bs, 1H), 5.47 (dt, J=11.2, 7.0 Hz, 1H), 4.60 dd, J=19.0, 6.9 Hz, 1H), 4.33 (m, 1H), 3.09–2.92 (m, 2H), 2.79 (dd, J=17.2, 8.1 Hz, 1H), 2.38–1.86 (m, 5H). $^{13}$C NMR (CDCl$_3$): δ 173.6, 173.3, 172.9, 171.7, 171.0, 167.6, 138.7, 133.4, 132.9, 131.6, 131.1, 128.7, 128.1, 125.7, 124.5, 102.8, 97.0, 61.7, 59.0, 52.8, 50.6, 33.9, 33.5, 32.3, 26.9, 21.5. ESI MS: 442.14 (M+H).

(3S,6S,10aS)-6-(3-Methyl-benzoylamino)-5-oxo-1,2,3,5, 6,7,10,10a-octahydro-pyrrolo[1,2-a]azocine-3-carboxylic acid (2-hydroxy-5-oxo-tetrahydro-furan-3-yl)-amide $^1$H NMR (CDCl$_3$): δ 7.62–7.58 (m, 2H), 7.32 (m, 3H), 5.89–5.56 (m, 3H), 5.48 (m, 2H), 4.62 (dd, J=16.9, 7.7 Hz, 2H), 4.34 (m, 3H), 3.01 (m, 2H), 2.83, (m, 2H), 2.83 (dd, J=16.9, 8.1 Hz, 1H), 2.47–2.16 (m, 3H), 2.38 (s, 3H), 2.00–1.84 (m, 2H). $^{13}$C NMR (CDCl$_3$): δ 173.6, 173.3, 172.9, 171.7, 171.0, 167.6, 138.7, 133.4, 133.0, 131.6, 131.1, 128.7, 128.2, 125.7, 124.5, 103.4, 97.6, 61.7, 59.0, 52.8, 50.6, 48.8, 33.9, 33.4, 32.3, 26.9, 21.5. ESI MS: 442.14 (M+H).

(3S,6S,10aS)-6-(4-Methyl-benzoylamino)-5-oxo-1,2,3,5, 6,7,10,10a-octahydro-pyrrolo[1,2-a]azocine-3-carboxylic acid (2-hydroxy-5-oxo-tetrahydro-furan-3-yl)-amide: $^1$H NMR (CDCl$_3$): δ 7.70 (d, J=8.0 Hz, 2H), 7.22 (d, J=8.1 HZ, 2H), 5.89–5.66 (m, 3H), 5.48 (m, 2H), 4.63 (dd, J=19.7, 8.1 Hz, 2H), 4.35 (m, 1H), 3.01 (m, 2H), 2.82 (dd, J=17.2, 8.4 Hz, 1H), 2.48–2.18 (m, 3H), 2.39 (s, 3H), 2.00–1.87 (m, 2H). $^{13}$C NMR (CDCl$_3$): δ 173.7, 172.9, 171.0, 167.4, 142.8, 131.7, 131.0, 130.5, 129.5, 127.5, 125.7, 102.8, 97.0, 62.0, 61.7, 59.1, 52.8, 50.6, 48.8, 33.9, 33.5, 32.3, 26.9, 21.7. ESI MS: 442.14 (M+H).

(3S,6S,10aS)-6-(2-Fluoro-benzoylamino)-5-oxo-1,2,3,5, 6,7,10,10a-octahydro-pyrrolo[1,2-a]azocine-3-carboxylic acid (2-hydroxy-5-oxo-tetrahydro-furan-3-yl)-amide: $^1$H NMR (CDCl$_3$): δ 7.85 (dd, J=8.8, 5.1 Hz, 2H), 7.25, 7.11 (m, 3H), 5.91–5.86 (m, 3H), 5.51 (m, 1H), 4.75 (m, 1H), 4.65 (dd, J=13.6, 8.4 Hz, 1H), 4.32 (m, 1H), 3.06 (m, 2H), 2.87 (dd, J=17.2, 8.1 Hz, 1H), 2.49–1.84 (m, 6H). ESI MS: 446.10 (M+H).

(3S,6S,10aS)-6-(3-Fluoro-benzoylamino)-5-oxo-1,2,3,5, 6,7,10,10a-octahydro-pyrrolo[1,2-a]azocine-3-carboxylic acid (2-hydroxy-5-oxo-tetrahydro-furan-3-yl)-amide: $^1$H NMR (CDCl$_3$): δ 7.56 (dd, J=12.4, 8.4 Hz, 2H), 7.40 (m, 2H), 7.21 (dt, J=8.0, 6.3 Hz, 1H), 5.90–5.67 (m, 2H), 5.48 (m, 1H), 4.65 (m, 2H), 4.32 (m, 1H), 3.08–2.97 (m, 2H), 2.83 (dd, J=17.2, 8.4 Hz, 1H), 2.49–1.84 (m, 6H). $^{13}$C NMR (CDCl$_3$): δ 173.8, 172.8, 171.8, 166.0, 164.5, 161.3, 135.7, 131.2, 130.6, 130.5, 126.1, 125.8, 123.1, 119.3, 119.1, 114.9, 114.7, 102.8, 97.0, 61.9, 60.7, 59.1, 50.7, 48.7, 33.9, 33.3, 32.2, 27.1, 21.3. ESI MS:446.10 (M+H).

(3S,6S,10aS)-6-(4-Fluoro-benzoylamino)-5-oxo-1,2,3,5, 6,7,10,10a-octahydro-pyrrolo[1,2-a]azocine-3-carboxylic acid (2-hydroxy-5-oxo-tetrahydro-furan-3-yl)-amide: $^1$H NMR (CDCl$_3$): δ 8.00 (t, J=6.6 Hz, 1H), 7.65 (m, 1H), 7.49 (m, 1H), 7.26 (m, 1H), 7.14 (dd, J=11.7, 8.4 Hz, 1H), 5.91–5.68 (m, 3H), 5.51 (m, 1H), 4.66 (m, 2H), 4.29 (m, 1H), 3.06 (m, 2H), 2.83 (dd, J=16.8, 8.4 Hz, 1H), 2.49–2.17 (m, 3H), 2.05–1.85 (m, 2H). $^{13}$C NMR (CDCl$_3$): δ 175.2, 173.6, 172.6, 172.3, 171.5, 171.2, 163.3, 163.1, 161.7, 160.2, 160.1, 133.9, 131.6, 131.3, 130.8, 125.8, 125.6, 125.2, 124.9, 120.6, 116.6, 116.4, 102.6, 96.9, 61.8, 61.4, 60.7, 59.1, 58.9, 55.3, 53.2, 52.9, 50.9, 50.7, 48.8, 34.6, 34.3, 33.9, 33.3, 32.2, 32.1, 30.9, 27.1, 26.9, 21.3, 19.3, 14.4. ESI MS: 446.10 (M+H).

(3S,6S,10aS)-5-Oxo-6-(2-trifluoromethyl-benzoylamino)-1,2,3,5,6,7,10,10a-octahydro-pyrrolo[1,2-a]azocine-3-carboxylic acid (2-hydroxy-5-oxo-tetrahydro-furan-3-yl)-amide: $^1$H NMR (CDCl$_3$): δ 7.71 (d, J=7.4 Hz, 1H), 7.58 (m, 3H), 7.25 (bs, 1H), 7.11 (bs, 1H), 5.86–5.73 (m, 3H), 5.46 (m, 1H), 4.58–4.49 (m, 1H), 4.29 (bs, 1H), 3.01 (m, 2H), 2.78 (dd, J=13.9, 6.6 Hz, 1H), 2.42–2.08 (m, 5H), 2.04–1.85 (m, 2H). ESI MS 496.13 (M+H).

(3S,6S,10aS)-5-Oxo-6-(3-trifluoromethyl-benzoylamino)-1,2,3,5,6,7,10,10a-octahydro-pyrrolo[1,2-a]azocine-3-carboxylic acid (2-hydroxy-5-oxo-tetrahydro-furan-3-yl)-amide $^1$H NMR (CDCl$_3$): δ 8.11–7.92 (m, 2H), 7.79 (m, 1H), 7.55 (m, 1H), 7.49–7.37 (m, 1H), 5.92–5.71 (m, 2H), 5.55 (m, 1H), 4.63 (m, 1H), 4.39 (s, 1H), 3.09–2.92 (m, 3H), 2.43 (m, 2H), 2.22 (m, 2H), 2.11–1.85 (m, 2H). ESI MS 496.13 (M+H).

(3S,6S,10aS)-5-Oxo-6-(4-trifluoromethyl-benzoylamino)-1,2,3,5,6,7,10,10a-octahydro-pyrrolo[1,2-a]azocine-3-carboxylic acid (2-hydroxy-5-oxo-tetrahydro-furan-3-yl)-amide: $^1$H NMR (CDCl$_3$): δ 7.70 (d, J=7.4 Hz, 1H), 7.61–7.51 (m, 3H), 7.09 (bs, 1H), 5.85 (m, 2H), 5.74 (m, 1H), 5.50 (m, 1H), 4.58 (m, 1H), 4.31 (m, 1H), 3.03 (m, 2H), 2.80 (dd, J=17.1, 8.1 Hz,1H), 2.40 (dd, J=14.7, 8.1 Hz, 1H), 2.18 (m, 3H), 2.04–1.83 (m, 2H). $^{13}$C NMR (CDCl$_3$): δ 173.5, 172.4, 171.6, 167.8, 134.9, 132.3, 131.1, 130.4, 128.7, 127.8, 127.4, 126.7, 125.7, 121.9, 118.4, 102.6, 96.9, 61.8, 60.7, 59.2, 50.6, 33.9, 33.2, 32.0, 27.1, 21.3, 14.4. ESI MS 496.12 (M+H).

Table II relates to non-limiting examples of analogs comprising a second aspect of this category, said analogs having the formula:

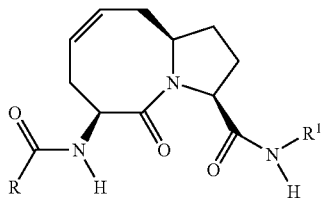

wherein R which is substituted or unsubstituted heteroaryl and R$^1$ are defined in Table II herein below.

TABLE II

| No. | R | R$^1$ |
|---|---|---|
| 45 | pyrimidin-2-yl | 2-hydroxy-5-oxo-tetrahydrofuran-3-yl |
| 46 | pyrimidin-4-yl | 2-hydroxy-5-oxo-tetrahydrofuran-3-yl |
| 47 | pyrimidin-5-yl | 2-hydroxy-5-oxo-tetrahydrofuran-3-yl |
| 48 | 2-isobutoxypyrimidin-4-yl | 2-hydroxy-5-oxo-tetrahydrofuran-3-yl |
| 49 | 2-isobutylaminopyrimidin-4-yl | 2-hydroxy-5-oxo-tetrahydrofuran-3-yl |
| 50 | 2-phenoxypyrimidin-4-yl | 2-hydroxy-5-oxo-tetrahydrofuran-3-yl |
| 51 | quinolin-2-yl | 2-hydroxy-5-oxo-tetrahydrofuran-3-yl |
| 52 | quinolin-3-yl | 2-hydroxy-5-oxo-tetrahydrofuran-3-yl |
| 53 | quinolin-4-yl | 2-hydroxy-5-oxo-tetrahydrofuran-3-yl |
| 54 | isoquinolin-1-yl | 2-hydroxy-5-oxo-tetrahydrofuran-3-yl |
| 55 | isoquinolin-3-yl | 2-hydroxy-5-oxo-tetrahydrofuran-3-yl |
| 56 | pyridin-2-yl | 2-hydroxy-5-oxo-tetrahydrofuran-3-yl |
| 57 | pyridin-3-yl | 2-hydroxy-5-oxo-tetrahydrofuran-3-yl |
| 58 | pyridin-4-yl | 2-hydroxy-5-oxo-tetrahydrofuran-3-yl |
| 59 | 3-chloropyridin-2-yl | 2-hydroxy-5-oxo-tetrahydrofuran-3-yl |
| 60 | 4-chloropyridin-2-yl | 2-hydroxy-5-oxo-tetrahydrofuran-3-yl |
| 61 | 3-methylpyridin-2-yl | 2-hydroxy-5-oxo-tetrahydrofuran-3-yl |
| 62 | 4-methylpyridin-2-yl | 2-hydroxy-5-oxo-tetrahydrofuran-3-yl |
| 63 | 1,2,3,4-tetrahydroquinolin-2-yl | 2-hydroxy-5-oxo-tetrahydrofuran-3-yl |
| 64 | 1,2,3,4-tetrahydroquinolin-3-yl | 2-hydroxy-5-oxo-tetrahydrofuran-3-yl |
| 65 | thiophen-2-yl | 2-hydroxy-5-oxo-tetrahydrofuran-3-yl |
| 66 | thiophen-3-yl | 2-hydroxy-5-oxo-tetrahydrofuran-3-yl |
| 67 | furan-2-yl | 2-hydroxy-5-oxo-tetrahydrofuran-3-yl |
| 68 | furan-3-yl | 2-hydroxy-5-oxo-tetrahydrofuran-3-yl |
| 69 | benzo[b]thiophen-2-yl | 2-hydroxy-5-oxo-tetrahydrofuran-3-yl |
| 70 | benzo[b]thiophen-3-yl | 2-hydroxy-5-oxo-tetrahydrofuran-3-yl |
| 71 | benzo[b]thiophen-5-yl | 2-hydroxy-5-oxo-tetrahydrofuran-3-yl |
| 72 | pyrimidin-2-yl | 2-ethoxy-5-oxo-tetrahydrofuran-3-yl |
| 73 | pyrimidin-4-yl | 2-ethoxy-5-oxo-tetrahydrofuran-3-yl |
| 74 | pyrimidin-5-yl | 2-ethoxy-5-oxo-tetrahydrofuran-3-yl |
| 75 | 2-isobutoxypyrimidin-4-yl | 2-ethoxy-5-oxo-tetrahydrofuran-3-yl |
| 76 | 2-isobutylaminopyrimidin-4-yl | 2-ethoxy-5-oxo-tetrahydrofuran-3-yl |
| 77 | 2-phenoxypyrimidin-4-yl | 2-ethoxy-5-oxo-tetrahydrofuran-3-yl |
| 78 | quinolin-2-yl | 2-ethoxy-5-oxo-tetrahydrofuran-3-yl |
| 79 | quinolin-3-yl | 2-ethoxy-5-oxo-tetrahydrofuran-3-yl |
| 80 | quinolin-4-yl | 2-ethoxy-5-oxo-tetrahydrofuran-3-yl |
| 81 | isoquinolin-1-yl | 2-ethoxy-5-oxo-tetrahydrofuran-3-yl |
| 82 | isoquinolin-3-yl | 2-ethoxy-5-oxo-tetrahydrofuran-3-yl |
| 83 | pyridin-2-yl | 2-ethoxy-5-oxo-tetrahydrofuran-3-yl |
| 84 | pyridin-3-yl | 2-ethoxy-5-oxo-tetrahydrofuran-3-yl |
| 85 | pyridin-4-yl | 2-ethoxy-5-oxo-tetrahydrofuran-3-yl |
| 86 | 3-chloropyridin-2-yl | 2-ethoxy-5-oxo-tetrahydrofuran-3-yl |

TABLE II-continued

| No. | R | R$^1$ |
|---|---|---|
| 87 | 4-chloropyridin-2-yl | 2-ethoxy-5-oxo-tetrahydrofuran-3-yl |
| 88 | 3-methylpyridin-2-yl | 2-ethoxy-5-oxo-tetrahydrofuran-3-yl |
| 89 | 4-methylpyridin-2-yl | 2-ethoxy-5-oxo-tetrahydrofuran-3-yl |
| 90 | 1,2,3,4-tetrahydroquinolin-2-yl | 2-ethoxy-5-oxo-tetrahydrofuran-3-yl |
| 91 | 1,2,3,4-tetrahydroquinolin-3-yl | 2-ethoxy-5-oxo-tetrahydrofuran-3-yl |
| 92 | thiophen-2-yl | 2-ethoxy-5-oxo-tetrahydrofuran-3-yl |
| 93 | thiophen-3-yl | 2-ethoxy-5-oxo-tetrahydrofuran-3-yl |
| 94 | furan-2-yl | 2-ethoxy-5-oxo-tetrahydrofuran-3-yl |
| 95 | furan-3-yl | 2-ethoxy-5-oxo-tetrahydrofuran-3-yl |
| 96 | benzo[b]thiophen-2-yl | 2-ethoxy-5-oxo-tetrahydrofuran-3-yl |
| 97 | benzo[b]thiophen-3-yl | 2-ethoxy-5-oxo-tetrahydrofuran-3-yl |
| 98 | benzo[b]thiophen-5-yl | 2-ethoxy-5-oxo-tetrahydrofuran-3-yl |

The compounds of this aspect of Category I can be suitably prepared by the procedure outlined herein below, utilizing intermediate 8 (Type I Intermediates) which can be synthesized by the procedure outlined in Scheme IV.

Scheme IV

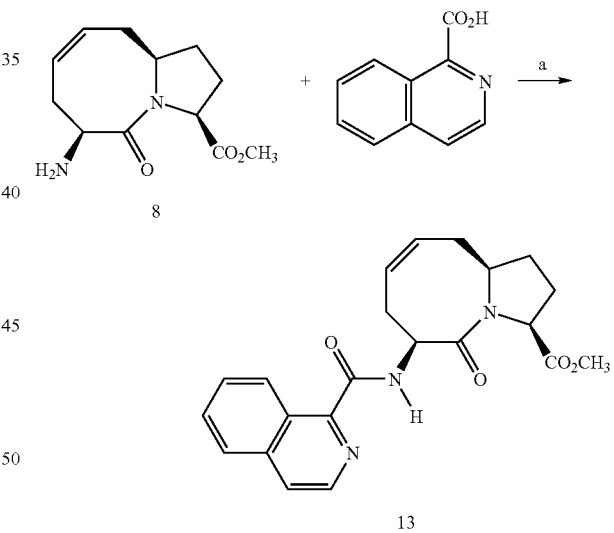

Reagents and conditions: (a) EDCl. HOBt, CH$_2$Cl$_2$; rt 18 hr.

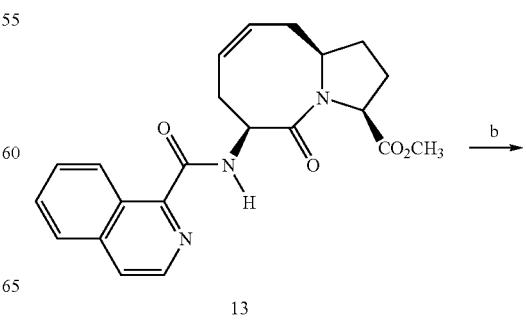

13

-continued

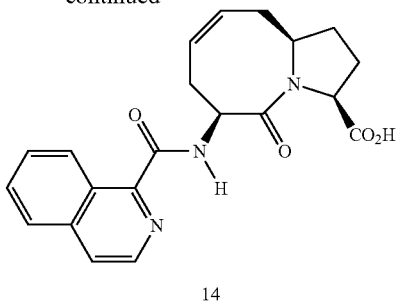

14

Reagents and conditions: (b) LiOH, THF/H2O; rt 18 hr.

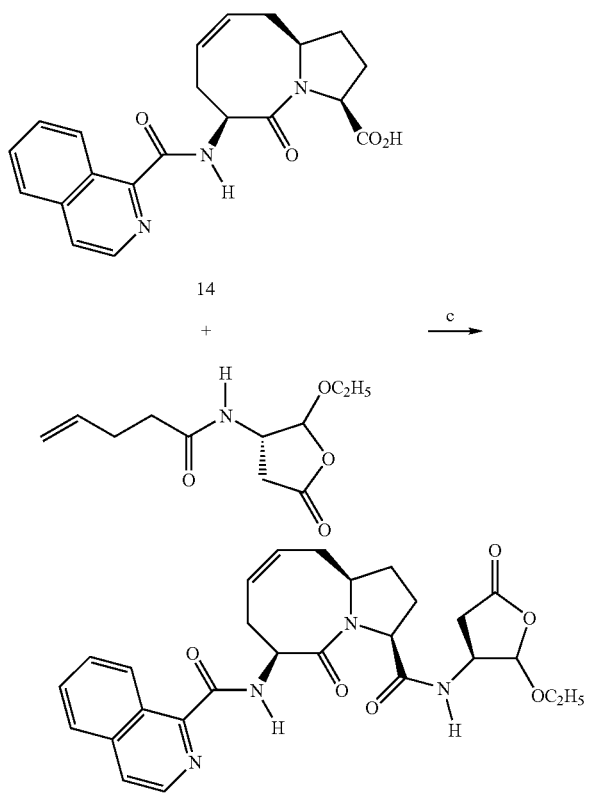

Reagents and conditions: (c) (Ph₃P)₄Pd, HOBt, EDCl, H⁺; CH₂Cl₂; rt 6 hr.

EXAMPLE 3

(3S,6S,10aS)-6-[(Isoquinoline-1-carbonyl)-amino]-5-oxo-1,2,3,5,6,7,10,10a-octahydro-pyrrolo[1,2-a]azocine-3-carboxylic acid (2-ethoxy-5-oxo-tetrahydro-furan-3-yl)-amide (15)

Preparation of (3S,6S,10aS)-[(isoquinoline-1-carbonyl)-amino]-5-oxo-1,2,3,5,6,7,10,10a-octahydro-pyrrolo[1,2-a]azocine-3-carboxylic acid methyl ester (13): 6-Amino-5-oxo-1,2,3,5,6,7,10,10a-octahydro-pyrrolo[1,2-a]azocine-3-carboxylic acid methyl ester, 8, 1.69 grams (7.1 mmol) and 1-isoquinolinic acid (2.46 g, 14.2 mmol) are dissolved in 75 ml of dichloromethane. To this solution is added dimethylaminopyridine (0.87 g, 7.1 mmol) and dicyclohexylcarbodiimide (2.93 g,14.2 mmol). The reaction is stirred overnight, during which time a precipitate forms which is removed by filtration and washed with dichloromethane. The filtrate is concentrated and the residue is taken up in ether. (Any additional precipitates which form are also removed by filtration.) The residue is purified over silica (50% ethyl acetate:hexane), to afford 1.62 g (58% yield) of the desired product as a oil. ¹H NMR (CDCl₃): δ 9.55 (m, 1H), 9.18 (d, J=7.3 Hz, 1H), 8.50 (d, J=5.5 Hz, 1H), 7.88–7.65 (m, 4H), 5.99–5.81 (m, 2H), 5.38 (m, 1H), 4.59 (dd, J=8.7,3.2 Hz, 1H), 4.26 (m, 1H), 3.76 (s, 3H), 3.03–2.86 (m, 2H), 2.60–2.50 (m, 2H), 2.23–1.98 (m, 4H). ¹³C NMR (CDCl₃): δ 172.7, 170.9, 165.7, 148.1, 140.8, 137.6, 130.6, 129.6, 128.7, 127.7, 127.2, 127.1, 126.4, 124.5, 60.5, 59.1, 52.3, 51.3, 35.1, 33.4, 27.5. ESI MS 394.14 (M+H).

Preparation of (3S,6S,10aS)-6-[(isoquinoline-1-carbonyl)-amino]-5-oxo-1,2,3,5,6,7,10,10a-octahydro-pyrrolo[1,2-a]azocine-3-carboxylic acid (14): [(Isoquinoline-1-carbonyl)-amino]-5-oxo-1,2,3,5,6,7,10,10a-octahydro-pyrrolo[1,2-a]azocine-3-carboxylic acid methyl ester, 13, (1.62 g, 4.1 mmol) are added to 20 mL of THF/H₂O (3:1). Lithium hydroxide (0.25 g) is added and the reaction stirred at room temperature for 18 hours then diluted with ethyl acetate (100 mL). The organic layer is washed with 1N HCl, brine, and dried over MgSO₄. Solvent is removed in vacuo to afford 1.41 g (90% yield of the desired product as an oil, which is used without further purification. ¹H NMR (CDCl₃): δ 9.30 (d, J=8.5 Hz, 1H), 8.92 (d, J=7.7 Hz, 1H), 8.53 (d, J=7.8 Hz, 1H), 7.93 (m, 2H), 7.83–7.71 (m, 2H), 5.88 (m, 1H), 5.75 (m, 1H), 5.50 (m, 1H), 4.70 (d, 7.4 Hz, 1H), 4.37 (m, 1H), 3.10–2.91 (m, 2H), 2.44 (m, 3H), 2.21 (m, 1H), 2.03 (m, 2H), ¹³C NMR (CDCl₃): δ 173.5, 171.9, 165.0, 148.1, 139.3, 137.9, 137.6, 131.7, 129.8, 129.5, 127.7, 127.3, 126.9, 125.9, 125.2, 61.4, 59.5, 50.9, 33.9, 33.3, 32.5, 26.0. ESI MS 380.15(M+H).

Preparation of (3S,6S,10aS)-6-[(isoquinoline-1-carbonyl)-amino]-5-oxo-1,2,3,5,6,7,10,10a-octahydro-pyrrolo[1,2-a]azocine-3-carboxylic acid (2-ethoxy-5-oxo-tetrahydro-furan-3-yl)-amide (15): To a solution of N-allyloxycarbonyl-4-amino-5-ethoxy-2-oxotetrahydrofuran (1.83 g, 8.0 mmol) in dichloromethane (30 mL) is added N, N-dimethylbarbituric acid (2.98 g, 47.8 mmol) and tetrakispalladium(0) triphenyl phosphine (0.85 g, 1.9 mmol). The resulting mixture immediately produces CO₂ and is allowed to stir at room temperature for 15 minutes after gas evolution has ceased. To this mixture is added 6-[(Isoquinoline-1-carbonyl)-amino]-5-oxo-1,2,3,5,6,7,10,10a-octahydro-pyrrolo[1,2-a]azocine-3-carboxylic acid, 14, (1.2 g, 3.15 mmol), hydroxybenztriazole (1.0 g, 18.5 mmol) and 1-(3-dimethylaminopropyl)-3-ethyl carbodiimide hydrochloride (1.4 g, 18.5 mmol). The reaction mixture is allowed to stir for 2 hours at room temperature. The reaction mixture is poured into water and extracted with ethyl acetate. The organic layers are combined and washed with saturated sodium bicarbonate, brine, dried with sodium sulfate and concentrated in vacuo. The residue is purified over silica (ethyl acetate) to afford 1.42 g (89% yield) of the desired product as a yellow foam. ¹H NMR (300 MHz, CDCl₃): δ 9.50 (m,1H), 9.02 (d, J=7.7 Hz, 1H), 8.50 (d, J=5.4 Hz, 1H), 7.83 (m, 3H), 7.69–7.41 (m, 3H), 5.84 (m, 1H), 5.70 (m, 1H), 5.49 (m, 2H), 4.71 (m, 2H), 4.26 (m, 1H), 3.90 (m, 1H), 3.71 (m, 1H), 3.17–2.95 (m, 2H), 2.80 (m, 1H), 2.51=2.30 (m, 4H), 2.14 (m,1H), 1.90 (m, 2H), 1.31 (t, J=7.0 HZ, 3H). ¹³C NMR (CDCl₃): δ 173.8, 171.9, 171.0, 165.7, 147.8, 140.8, 137.6, 133.4, 132.4, 132.2, 132.0, 130.7, 130.4, 128.8, 127.7, 127.6, 127.2, 126.0, 124.8, 101.6, 66.0, 61.0, 58.9, 50.3, 48.4, 34.9, 33.5, 33.0, 32.6, 36.6, 15.2. ESI MS-507.15 (M+H).

(3S,6S,10aS)-6-[(thiophene-3-carbonyl)-amino]-5-oxo-1,2,3,5,6,7,10,10a-octahydro-pyrrolo[1,2-a]azocine-3-carboxylic acid (2-ethoxy-5-oxo-tetrahydro-furan-3-yl)-amide: $^1$H NMR (CDCl$_3$): δ 7.87 (dd, J=3.0, 1.5 Hz, 1H), 7.38–7.36 (m, 1H), 7.32–7.28 (m, 1H), 7.04 (m, 1H), 5.77 (m, 1H), 5.64 (m, 1H), 5.43–5.23 (m, 2H), 4.78–4.55 (m, 1H), 4.20 (m, 1H), 3.10–2.72 (m, 3H), 2.38–2.09 (m, 5H), 1.87 (m, 2H), 1.28–1.16 (m, 3H); $^{13}$C NMR (CDCl$_3$): δ 175.31, 173.71, 171.71, 170.92, 162.37, 137.01, 131.24, 130.42, 129.04, 126.88, 126.33, 126.25, 126.03, 107.29, 101.56, 66.02, 61.52, 50.43, 35.09, 33.42, 32.30, 26.72, 15.25; ESI MS 462.08 (M+H).

As with the first aspect of Category I the 2-ethoxy-5-oxo-tetrahydrofuran-3-yl cysteine trap of Category II analogs can be converted to the 2-hydroxy-5-oxo-tetrahydrofuran-3-yl cysteine trap by the procedure outlined in Scheme V herein below.

Scheme V

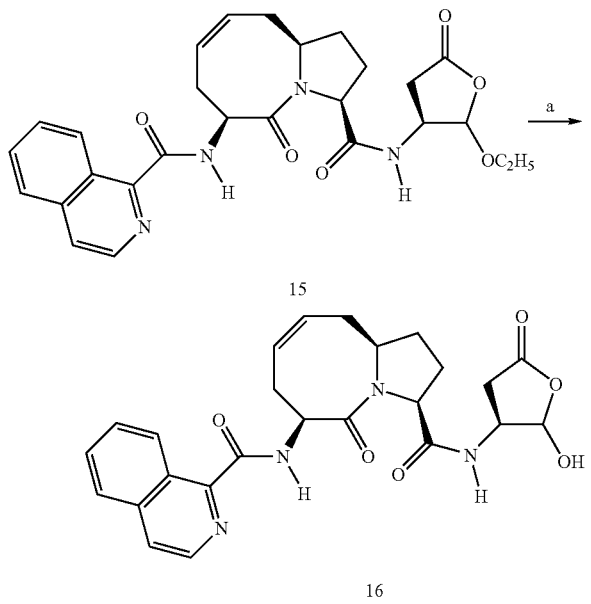

Reagents and Conditions (a) TFA, CH$_2$Cl$_2$; rt 2 hr.

EXAMPLE 4

6-[(Isoquinoline-1-carbonyl)-amino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide (16)

Preparation of (3S,6S,10aS)-6-[(isoquinoline-1-carbonyl)-amino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide (16): 6-[(Isoquinoline-1-carbonyl)-amino]-5-oxo- 1,2,3,5,6,7,10,10a-octahydro-pyrrolo[1,2-a]azocine-3-carboxylic acid (2-ethoxy-5-oxo-tetrahydro-furan-3-yl)-amide, 15, (1.42 g, 2.80 mmol) is stirred in a solution of trifluroacetic acid 5 mL acetonitrile 5 mL, and water 2.5 mL for 2 hours. Solvents are removed in vacuo and the resulting residue dissolved in ethyl acetate and re-concentrated to remove any excess TFA. The crude product is purified over silica (ethyl acetate:0.1% acetic acid,) to afford 1.18 g (78% yield) of the desired product as a yellow foam. $^1$H NMR (CDCl$_3$): δ 9.30 (m, 1H), 8.85 (d, 7.6 Hz, 1H), 8.48 (d, J=5.4 Hz, 1H), 7.87–7.34 (m, 6H), 5.92–5.71 (m, 3H), 5.54 (m, 1H), 4.71–4.35 (m, 3H), 3.03 (m, 4H), 2.43 (m, 3H), 2.19 (m, 2H), 1.98 (m, 1H). $^{13}$C NMR (CDCl$_3$): δ 173.9, 172.5, 171.4, 165.9, 147.9, 140.7, 137.6, 131.4, 130.8, 128.9, 127.5, 127.2, 125.6, 124.9, 61.7, 59.1, 50.4, 34.2, 33.4, 32.3, 27.0. ESI MS 479.11 (M+H). HRMS calc. 479.1931, found 479.1941.

(3S,6S,10aS)-6-[(Benzo[b]thiophene-2-carbonyl)-amino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide: $^1$H NMR (CDCl$_3$): δ 7.95–7.80 (m, 3H), 7.42 (m, 3H), 7.26–7.13 (m, 1H), 5.85–5.17 (m, 5H), 4.64–4.28 (m, 3H), 3.21–2.76 (m, 4H), 2.54 (m, 1H), 2.41–1.66 (m, 8H). ESI MS 484.02 (M+H).

(3S,6S,10aS)-6-[(thiophene-3-carbonyl)-amino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide: $^1$H NMR (CD$_3$OD): δ 8.21 (m, 1H), 7.58 (m, 1H), 7.51 (m, 1H), 6.04 (m, 2H), 5.44 (m, 2H), 4.55–4.46 (m, 3H), 4.36 (bs, 1H), 3.34 (m, 2H), 3.07 (m, 1H), 2.89 (m, 1H), 2.72–2.36 (m, 4H), 2.12 (m, 4H); $^{13}$C NMR ((CD$_3$OD): δ 177.89, 176.21, 172.73, 171.78, 163.97, 136.46, 131.88, 130.77, 129.46, 126.61, 97.38, 63.05, 59.21, 50.88, 47.27, 36.36, 32.65, 31.28, 27.39, 21.52; ESI MS 434.07 (M+H).

6-[(2-Isobutoxy-pyrimidine-4-carbonyl)-amino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide: $^1$H-NMR (300 MHz, CDCl$_3$): δ 8.79–8.78 (d, 1H, J=4.8 Hz), 8.61–8.59 (d, 1H, J=7.21 Hz), 8.51 (bs, 2H), 7.73–7.71 (d, 1H, J=5.1 Hz), 7.39 (bs, 1H), 5.95–5.86 (m, 1H), 5.82–5.74 (m, 1H), 5.48–5.40 (m, 1H), 4.69–4.66 (bm, 1H), 4.37–4.28 (m, 1H), 2.42–4.23 (d, 2H, J=6.6 Hz), 3.08–2.97 (m, 3H), 2.45–2.41 (m, 3H), 2.24–1.84 (m, 6H), 1.09–1.07 (d, 6H, J=6.6 Hz); $^{13}$C-NMR (75.5 MHz, CDCl$_3$): δ 173.77, 171.79, 164.91, 164.77, 162.65, 160.38, 159.59, 158.54, 137.61, 131.97, 125.10, 117.16, 113.66, 112.96, 111.01, 74.92, 74.12, 73.71, 63.15, 62.36, 58.67, 57.83, 51.30, 33.65, 29.25, 28.20, 19.81, 18.91; MS (ESI): m/e=502.18 (M+H).

(3S,6S,10aS)-6-[(2-Isobutylamino-pyrimidine-4-carbonyl)-amino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide: $^1$H-NMR (300 MHz, CDCl$_3$): δ 11.23 (bs, 3H), 9.71 (bs, 1H), 8.53–8.51 (d, 1H, J=6.9 Hz), 8.46–8.44 (d, 1H, J=4.8 Hz), 7.50–7.48 (d, 1H, J=6.0 Hz, 7.34–7.32 (d, 1H, J=5.1 Hz), 5.91–5.90, (m, 1H), 5.84–5.76 (m, 1H), 5.41–5.33 (m, 1H), 4.69–4.66 (m, 1H), 4.30–4.28 (m, 1H), 3.47–3.45 (d, 2H, J=6.3 Hz), 3.09–2.94 (m, 3H), 2.52–2.34 (m, 3H), 2.23–2.21 (m, 3H), 2.12–1.92 (m, 3H), 1.04–1.02 (m, 3H), $^{13}$C-NMR (75.5 MHz, CDCl$_3$): δ 174.17, 171.95, 171.57, 163.37, 162.34, 161.81, 161.29, 160.77, 160.39, 155.54, 152.06, 151.20, 137.59, 131.69, 129.65, 127.25, 125.25, 117.47, 113.67, 107.67, 106.32, 105.04, 63.20, 62.41, 58.79, 57.99, 52.27, 51.49, 49.65, 48.05, 35.28, 33.65, 32.45, 32.05, 29.50, 28.57, 28.18, 27.30, 21.29, 20.63, 19.75; MS (ESI): m/e=501.18 (M+H).

(3S,6S,10aS)-5-Oxo-6-[(2-phenoxy-pyrimidine-4-carbonyl)-amino]-1,2,3,5,6,7,10,10a-octahydro-pyrrolo[1,2-a]azocine-3-carboxylic acid (2-hydroxy-5-oxo-tetrahydro-furan-3-yl)-amide: $^1$H-NMR (300 MHz, CDCl$_3$): δ 8.74–8.70 (m, 1H), 8.62–8.58 (m, 1H), 7.78, (m, 1H), 7.49–7.44 (m, 3H), 7.34–7.25 (m, 1H), 7.22–7.19 (m, 2H), 6.04–5.84 (m, 1H), 5.82–5.68 (m, 1H), 5.50–5.31 (m, 1H), 4.80–4.55 (m, 1H), 4.34–4.19 (m, 1H), 3.60–2.85 (m, 3H), 2.50–2.34 (m, 3H), 2.31–2.11 (m, 3H), 2.08–1.79 (m, 3H), $^{13}$C-NMR (75.5 MHz, CDCl$_3$): δ 171.75, 169.53, 162.75, 159.96, 157.02, 150.64, 130.12, 128.77, 127.94, 126.88, 124.22, 124.01, 119.60, 114.58, 111.54, 100.47, 94.86, 59.57, 56.86, 50.93, 48.34, 46.71, 31.80, 31.23, 30.30, 30.15, 24.81; MS (ESI): m/e=522.13 (M+H).

(3S,6S,10aS)-5-Oxo-6-[(thiophene-3-carbonyl)-amino]-1,2,3,5,6,7,10,10a-octahydro-pyrrolo[1,2-a]azocine-3-carboxylic acid (2-hydroxy-5-oxo-tetrahydro-furan-3-yl)-amide: $^1$H-NMR (300 MHz, CD$_3$OD): δ 8.25–8.19 (m, 1H), 7.61–7.57 (m, 1H), 7.52–7.48 (m, 1H), 6.1–5.9 (m, 2H), 5.5–5.4 (m, 1H), 4.58–4.49 (m, 3H), 4.4–4.3 (m, 2H), 3.16–3.0 (m, 1H), 2.95–2.85 (m, 1H), 2.65–2.36 (m, 5H); $^{13}$C-NMR (75.5 MHz, CD$_3$OD): δ 177.90, 172.73, 163.97, 163.88, 136.46, 131.89, 130.77, 129.75, 129.46, 126.81, 126.61, 126.35, 97.37, 97.13, 96.96, 63.05, 62.32, 59.21, 59.07, 51.18, 50.89, 50.76, 48.70, 48.42, 48.13, 47.86, 47.57, 47.28, 47.00, 36.36, 32.65, 32.41, 32.01, 31.62, 31.29, 27.67, 27.39, 21.52; MS (ESI): m/e=434.07 (M+H).

(3S,6S,10aS)-5-Oxo-6-[(thiophene-3-carbonyl)-amino]-1,2,3,5,6,7,10,10a-octahydro-pyrrolo[1,2-a]azocine-3-carboxylic acid (2-ethoxy-5-oxo-tetrahydro-furan-3-yl)-amide: $^1$H-NMR (300 MHz, CDCl$_3$): δ 7.88–7.87 (m, 1H), 7.38–7.35 (m, 1H), 7.32–7.28 (m, 1H), 7.06–7.04 (m, 1H), 5.80–5.76 (m, 1H) 5.68–5.61 (m, 1H), 5.43–5.26 (m, 2H), 4.70–4.57 (m, 2H), 4.22–4.16 (m, 1H), 3.1–2.86 (m, 2H), 2.81–2.72 (m, 1 H), 2.38–2.10 (m, 5H), 1.98–1.80 (m, 2H), 1.29–1.17 (m, 3H); $^{13}$C-NMR (75.5 MHz, CDCl$_3$): δ 175.31, 173.69, 172.09, 171.12, 170.87, 162.37, 137.01, 131.24, 130.41, 129.04, 126.89, 126.33, 126.25, 126.03, 107.29, 101.54, 66.02, 65.65, 61.52, 61.12, 58.97, 52.16, 50.44, 50.27, 48.28, 35.09, 34.95, 34.04, 33.42, 33.12, 32.56, 32.30, 26.72. 15.25, 15.11; MS (ESI): m/e=462.07 (M+H).

The compounds which comprise Category II of the interleukin-1β converting enzyme inhibitors according to the present invention relates to compounds comprising a 3,6-disubstituted 5-oxo-decahydro-pyrrolo[1,2-a]azocine scaffold having the formula:

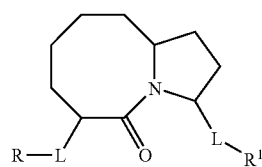

one iteration of which comprises scaffolds having the indicated stereochemistry. Table III relates to non-limiting examples of analogs comprising a first aspect of this category, said analogs having the formula:

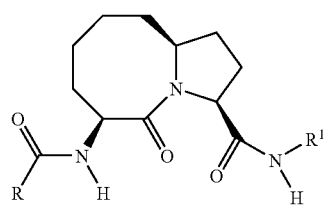

wherein R which is substituted or unsubstituted aryl and R$^1$ are defined in Table III herein below.

TABLE III

| No. | R | R$^1$ |
|---|---|---|
| 77 | phenyl | 2-hydroxy-5-oxo-tetrahydrofuran-3-yl |
| 78 | 2-methylphenyl | 2-hydroxy-5-oxo-tetrahydrofuran-3-yl |
| 79 | 3-methylphenyl | 2-hydroxy-5-oxo-tetrahydrofuran-3-yl |
| 80 | 4-methylphenyl | 2-hydroxy-5-oxo-tetrahydrofuran-3-yl |
| 81 | 2-fluorophenyl | 2-hydroxy-5-oxo-tetrahydrofuran-3-yl |
| 82 | 3-fluorophenyl | 2-hydroxy-5-oxo-tetrahydrofuran-3-yl |
| 83 | 4-fluorophenyl | 2-hydroxy-5-oxo-tetrahydrofuran-3-yl |
| 84 | 2-chlorophenyl | 2-hydroxy-5-oxo-tetrahydrofuran-3-yl |
| 85 | 3-chlorophenyl | 2-hydroxy-5-oxo-tetrahydrofuran-3-yl |
| 86 | 4-chlorophenyl | 2-hydroxy-5-oxo-tetrahydrofuran-3-yl |
| 87 | 2-methoxyphenyl | 2-hydroxy-5-oxo-tetrahydrofuran-3-yl |
| 88 | 3-methoxyphenyl | 2-hydroxy-5-oxo-tetrahydrofuran-3-yl |
| 89 | 4-methoxyphenyl | 2-hydroxy-5-oxo-tetrahydrofuran-3-yl |
| 90 | 2-trifluoromethylphenyl | 2-hydroxy-5-oxo-tetrahydrofuran-3-yl |
| 91 | 3-trifluoromethylphenyl | 2-hydroxy-5-oxo-tetrahydrofuran-3-yl |
| 92 | 4-trifluoromethylphenyl | 2-hydroxy-5-oxo-tetrahydrofuran-3-yl |
| 93 | 3,4,5-trimethoxyphenyl | 2-hydroxy-5-oxo-tetrahydrofuran-3-yl |
| 94 | benzoyl | 2-hydroxy-5-oxo-tetrahydrofuran-3-yl |
| 95 | phenylamino | 2-hydroxy-5-oxo-tetrahydrofuran-3-yl |
| 96 | 2-phenylethyl | 2-hydroxy-5-oxo-tetrahydrofuran-3-yl |
| 97 | naphth-1-yl | 2-hydroxy-5-oxo-tetrahydrofuran-3-yl |
| 98 | naphth-2-yl | 2-hydroxy-5-oxo-tetrahydrofuran-3-yl |
| 99 | phenyl | 2-ethoxy-5-oxo-tetrahydrofuran-3-yl |
| 100 | 2-methylphenyl | 2-ethoxy-5-oxo-tetrahydrofuran-3-yl |
| 101 | 3-methylphenyl | 2-ethoxy-5-oxo-tetrahydrofuran-3-yl |
| 102 | 4-methylphenyl | 2-ethoxy-5-oxo-tetrahydrofuran-3-yl |
| 103 | 2-fluorophenyl | 2-ethoxy-5-oxo-tetrahydrofuran-3-yl |
| 104 | 3-fluorophenyl | 2-ethoxy-5-oxo-tetrahydrofuran-3-yl |
| 105 | 4-fluorophenyl | 2-ethoxy-5-oxo-tetrahydrofuran-3-yl |
| 106 | 2-chlorophenyl | 2-ethoxy-5-oxo-tetrahydrofuran-3-yl |
| 107 | 3-chlorophenyl | 2-ethoxy-5-oxo-tetrahydrofuran-3-yl |
| 108 | 4-chlorophenyl | 2-ethoxy-5-oxo-tetrahydrofuran-3-yl |
| 109 | 2-methoxyphenyl | 2-ethoxy-5-oxo-tetrahydrofuran-3-yl |
| 110 | 3-methoxyphenyl | 2-ethoxy-5-oxo-tetrahydrofuran-3-yl |
| 111 | 4-methoxyphenyl | 2-ethoxy-5-oxo-tetrahydrofuran-3-yl |
| 112 | 2-trifluoromethylphenyl | 2-ethoxy-5-oxo-tetrahydrofuran-3-yl |
| 113 | 3-trifluoromethylphenyl | 2-ethoxy-5-oxo-tetrahydrofuran-3-yl |
| 114 | 4-trifluoromethylphenyl | 2-ethoxy-5-oxo-tetrahydrofuran-3-yl |
| 115 | 3,4,5-trimethoxyphenyl | 2-ethoxy-5-oxo-tetrahydrofuran-3-yl |
| 116 | benzoyl | 2-ethoxy-5-oxo-tetrahydrofuran-3-yl |
| 117 | phenylamino | 2-ethoxy-5-oxo-tetrahydrofuran-3-yl |
| 118 | 2-phenylethyl | 2-ethoxy-5-oxo-tetrahydrofuran-3-yl |
| 119 | naphth-1-yl | 2-ethoxy-5-oxo-tetrahydrofuran-3-yl |
| 120 | naphth-2-yl | 2-ethoxy-5-oxo-tetrahydrofuran-3-yl |

The compounds of this category can be suitably prepared by the procedure outlined herein below, utilizing intermediate 7 (Type I Intermediates) which can be synthesized by the procedure outlined in Scheme IV herein below.

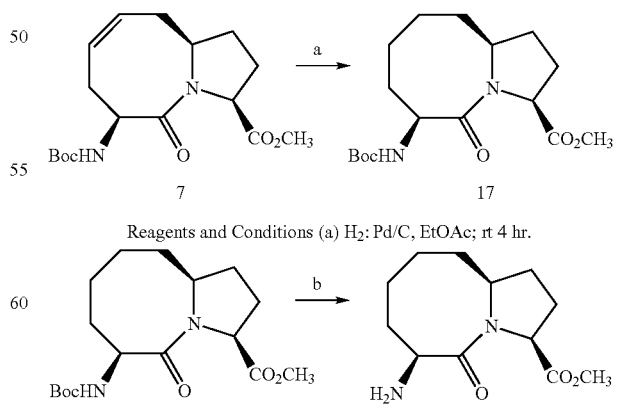

39

-continued

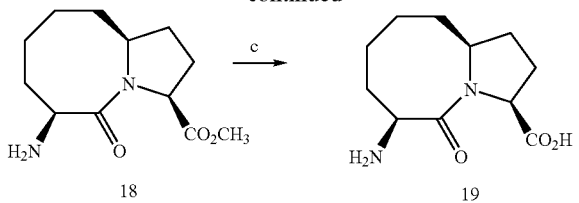

Reagents and Conditions (c) LiOH, THF/H₂O; rt 18 hr.

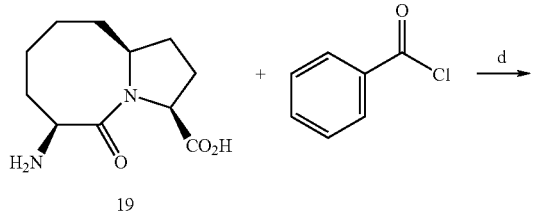

Reagents and Conditions (d) NaHCO₃, CH₂Cl₂/H₂O; rt 18 hr.

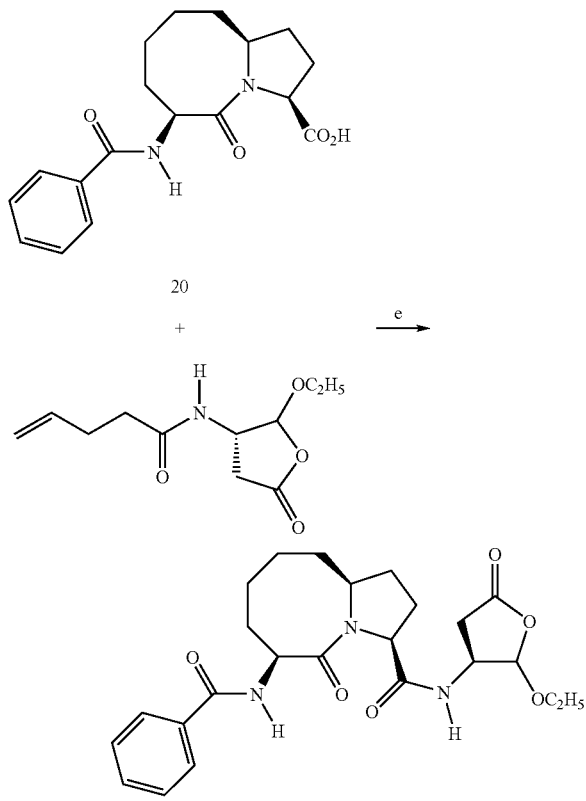

Reagents and Conditions (e) (Ph₃P)₄Pd, HOBt, EDCl, H⁺; CH₂Cl₂; rt 6 hr.

40

EXAMPLE 5

(3S,6S,10aS)-6-Benzoylamino-5-oxo-decahydro-pyrrolo[1,2-a]azocine-3-carboxylic (2-hydroxy-5-oxo-tetrahydro-furan-3-yl)-amide (21)

Preparation of (3S,6S,10aS)-6-tert-butoxycarbonylamino-5-oxo-decahydro-pyrrolo[1,2-a]azocine-3-carboxylic acid methyl ester (17): 6-tert-Butoxycarbonyl-amino-5-oxo-1,2,3,5,6,7,10,10a-octahydro-pyrrolo[1,2-a]azocine-3-carboxylic acid methyl ester, 7, (270 mg, 0.8 mmol) is treated with Pd/C (10 mol %) in EtOAc under an atmosphere of H₂ gas (balloon) for 4 hr. The catalyst is removed by filtration and the residue is concentrated in vacuo to afford the desired product as an oil which is used without further purification Preparation of (3S,6S,10aS)-6-amino-5-oxo-decahydro-pyrrolo[1,2-a]azocine-3-carboxylic acid methyl ester (18): 6-tert-butoxycarbonylamino-5-oxo-decahydro-pyrrolo[1,2-a]azocine-3-carboxylic acid methyl ester, 17, (272 mg, 0.8 mmol) is dissolved in dichloromethane (5 mL) and treated trifluoroacetic acid (5 mL). The solution is stirred for two hours then the solvent removed in vacuo to afford the desired product which is used without further purification.

Preparation of (3S,6S,10aS)-6-amino-5-oxo-decahydro-pyrrolo[1,2-a]azocine-3-carboxylic acid (19): The crude 6-amino-5-oxo-decahydro-pyrrolo[1,2-a]azocine-3-carboxylic acid methyl ester, 18, obtained from the previous reaction is dissolved in a mixture of THF:water (3:1) (40 mL) and treated with a catalytic amount of LiOH. The reaction solution is allowed to stir overnight then concentrated in vacuo to afford the desired product which is used without further purification.

Preparation of (3S,6S,10aS)-6-benzoylamino-5-oxo-decahydro-pyrrolo[1,2-a]azocine-3-carboxylic acid (20): A solution of 6-amino-5-oxo-decahydro-pyrrolo[1,2-a]azocine-3-carboxylic acid, 19, (181 mg, 0.8 mmol) in H₂O/CH₂Cl₂ (7 mL) is treated with sodium bicarbonate (0.50 g, 6 mmol) and benzoyl chloride (140 mg, 1.0 mmol). The reaction is stirred for 18 hours then diluted with ether (100 mL). The organic layer is washed twice with 1 N HCl, once with water, and dried over MgSO₄, filtered, and concentrated under in vacuo to afford a residue which is purified over silica to afford the desired compound.

Preparation of (3S,6S,10aS)-6-benzoylamino-5-oxo-decahydro-pyrrolo[1,2-a]azocine-3-carboxylic (2-hydroxy-5-oxo-tetrahydro-furan-3-yl)-amide (21): To a solution of (2-Ethoxy-5-oxo-tetrahydro-furan-3-yl)-carbamic acid allyl ester (183 mg, 0.8 mmol) in dichloromethane (6 mL) is added barbituric acid (300 mg, 1.9 mmol) and tetrakis triphenylphosphine palladium (92 mg, 0.08 mmol). The solution is stirred for 10 minutes and 6-benzoylamino-9-methyl-5-oxo-decahydro-pyrrolo[1,2-a]azocine-3 -carboxylic acid, 20, (105 mg, 0.32 mmol) is added followed by HOBt (99 mg, 0.74 mmol) and EDCI (141 mg, 0.74 mmol). The solution is stirred for 6 hours. Water is added and the organics are washed with NaHSO₄, Brine, NaHCO₃, and water. The organics are dried with MgSO₄ and concentrated under reduced pressure. The residue is purified over silica to afford an oil which is dissolved in dichloromethane and treated with TFA (5 mL) and water (1 mL). The solution is stirred for 2 hours and the solvent is removed. The residue is purified over silica to afford the desired product as a white powder. ¹H NMR (CDCl₃): δ 7.83 (m, 2H), 7.56–7.39 (m, 3H), 7.26 (m, 2H), 5.51 (d, J=5.2, 1H), 5.16 (m,1H), 4.72 (m, 1H), 4.56 (t, J=8.1 Hz, 1H), 4.35 (m, 1H), 3.95 (m, 1H), 3.71 (m, 2H), 2.90 (m, 1H), 2.52–2.38 (m, 2H), 2.26–2.05

(m, 4H), 1.87–1.61 (m, 5H), 1.32 (t, J=6.9 Hz, 3H). $^{13}$C NMR (CDCl$_3$): δ 173.7, 172.2, 171.7, 166.6, 131.9, 128.8, 127.3, 101.3, 65.9, 60.8, 59.5, 50.6, 48.6, 36.9, 36.3, 33.1, 32.4, 25.7, 25.6, 23.6, 15.2. ESI MS: 458.16 (M+H), 480.11 (M+Na).

Other examples of this category include the following compounds with the indicated stereochemistry.

(3S,6S,10aS)-6-(3-Methoxy-benzoylamino)-5-oxo-decahydro-pyrrolo[1,2-a]azocine-3-carboxylic acid (2-hydroxy-5-oxo-tetrahydro-furan-3-yl)-amide: $^1$H NMR (CDCl$_3$): d 7.39–7.28 (m, 3H), 7.02 (d, J=7.7 Hz, 1H), 5.32 (d, J=2.5 Hz, 1H), 5.08 (m, 1H), 4.34 (m, 1H), 4.17–4.05 (m, 1H), 3.82 (s, 3H), 2.89 (m, 1H), 2.51 (q, J=7.6 Hz, 1H), 2.34–0.85 (m, 15H). $^{13}$C NMR (CDCl$_3$): 174.1, 172.7, 167.3, 167.1, 159.9, 135.1, 129.8, 119.4, 118.2, 112.8, 107.9, 60.4, 55.7, 53.7, 50.7, 35.1, 33.5, 32.7, 29.9, 29.4, 28.9, 25.6, 22.9, 14.4. ESI MS:460.12 (M+H).

(3S,6S,10aS)-6-[(Naphthalene-1-carbonyl)-amino]-5-oxo-decahydro-pyrrolo[1,2-a]azocine-3-carboxylic acid (2-hydroxy-5-oxo-tetrahydro-furan-3-yl)-amide: $^1$H NMR (CDCl$_3$): δ 9.37 (d, J=7.6 Hz, 1H), 8.82–8.74 (m, 1H), 8.48 (t, J=4.4 Hz, 1H), 7.81 (m, 2H), 7.69 (m, 3H), 5.15 (bs, 1H), 4.37 (m, 1H), 4.13 (m, 1H), 2.51 (q, J=7.6 HZ, 1H), 2.32 (m, 1H), 2.18–1.58 (m, 11H), 1.27 (m, 6H), 1.01–0.82 (m, 3H). ESI MS: 48.13 (M+H).

(3S,6S,10aS)-6-[(Benzo[b]thiophene-2-carbonyl)-amino]-5-oxo-decahydro-pyrrolo[1,2-a]azocine-3-carboxylic acid (2-hydroxy-5-oxo-tetrahydro-furan-3-yl)-amide: $^1$H NMR (CDCl$_3$): δ 7.87 (m, 3H), 7.43 (m, 2H), 5.14 (m,1H), 4.63 (m, 1H), 4.34–4.17 (m, 2H), 2.52 (q, J=7.6, 1H), 2.39–1.62 (m, 8H), 1.36 (m, 3H). ESI MS: 392.26 (M+H).

(3S,6S,10aS)-6-[(Isoquinoline-1-carbonyl)-amino]-5-oxo-decahydro-pyrrolo[1,2-a]azocine-3-carboxylic acid (2-hydroxy-5-oxo-tetrahydro-furan-3-yl)-amide: $^1$H NMR (CDCl$_3$): δ 9.37 (m, 1H), 8.78 (m, 1H), 8.47 (m, 1H), 7.88–7.66 (m, 4H), 5.86 (m, 1H), 5.18 (m, 1H), 4.60–4.25 (m, 5H), 2.98–2.45 (m, 2H), 2.23–1.71 (m, 12H). ESI MS 481.14 (M+H).

(3S,6S,10aS)-8-[(Naphthalene-1-carbonyl)-amino]-9-oxo-decahydro-cyclopentacyclooctene-1-carboxylic acid (2-hydroxy-5-oxo-tetrahydro-furan-3-yl)-amide $^1$H NMR (CDCl$_3$): δ 8.37 (bs, 1H), 7.96–7.86 (m,4H), 7.57–7.47 (m, 3H), 7.11 (d, J=5.1 Hz, 1H), 5.78 (dd, J=41.7, 5.1, 1H), 5.16 (m, 1H), 4.79–4.48 (m, 1H), 4.64–4.35 (m, 2H), 3.10–2.75 (m, 2H), 2.56–1.62 (m, 12H). ESI MS: 480.14 (M+H).

The compounds which comprise Category III of the interleukin-1β converting enzyme inhibitors according to the present invention relates to compounds comprising a 3,6-disubstituted 5-oxo-decahydro-pyrrolo[1,2-a]azocine scaffold having the formula:

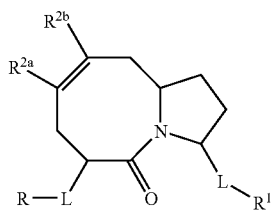

one iteration of which comprises scaffolds having the indicated stereochemistry. Table III relates to non-limiting examples of analogs comprising a first aspect of this category, said analogs having the formula:

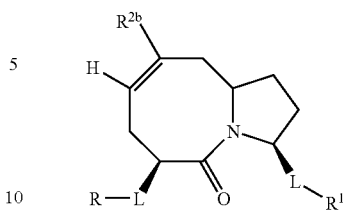

wherein R which is substituted or unsubstituted aryl and R$^1$ are defined in Table IV herein below.

TABLE IV

| No. | R | R$^1$ |
|---|---|---|
| 121 | phenyl | 2-hydroxy-5-oxo-tetrahydrofuran-3-yl |
| 122 | 2-methylphenyl | 2-hydroxy-5-oxo-tetrahydrofuran-3-yl |
| 123 | 3-methylphenyl | 2-hydroxy-5-oxo-tetrahydrofuran-3-yl |
| 124 | 4-methylphenyl | 2-hydroxy-5-oxo-tetrahydrofuran-3-yl |
| 125 | 2-fluorophenyl | 2-hydroxy-5-oxo-tetrahydrofuran-3-yl |
| 126 | 3-fluorophenyl | 2-hydroxy-5-oxo-tetrahydrofuran-3-yl |
| 127 | 4-fluorophenyl | 2-hydroxy-5-oxo-tetrahydrofuran-3-yl |
| 128 | 2-chlorophenyl | 2-hydroxy-5-oxo-tetrahydrofuran-3-yl |
| 129 | 3-chlorophenyl | 2-hydroxy-5-oxo-tetrahydrofuran-3-yl |
| 130 | 4-chlorophenyl | 2-hydroxy-5-oxo-tetrahydrofuran-3-yl |
| 131 | 2-methoxyphenyl | 2-hydroxy-5-oxo-tetrahydrofuran-3-yl |
| 132 | 3-methoxyphenyl | 2-hydroxy-5-oxo-tetrahydrofuran-3-yl |
| 133 | 4-methoxyphenyl | 2-hydroxy-5-oxo-tetrahydrofuran-3-yl |
| 134 | 2-trifluoromethylphenyl | 2-hydroxy-5-oxo-tetrahydrofuran-3-yl |
| 135 | 3-trifluoromethylphenyl | 2-hydroxy-5-oxo-tetrahydrofuran-3-yl |
| 136 | 4-trifluoromethylphenyl | 2-hydroxy-5-oxo-tetrahydrofuran-3-yl |
| 137 | 3,4,5-trimethoxyphenyl | 2-hydroxy-5-oxo-tetrahydrofuran-3-yl |
| 138 | benzoyl | 2-hydroxy-5-oxo-tetrahydrofuran-3-yl |
| 139 | phenylamino | 2-hydroxy-5-oxo-tetrahydrofuran-3-yl |
| 140 | 2-phenylethyl | 2-hydroxy-5-oxo-tetrahydrofuran-3-yl |
| 141 | naphth-1-yl | 2-hydroxy-5-oxo-tetrahydrofuran-3-yl |
| 142 | naphth-2-yl | 2-hydroxy-5-oxo-tetrahydrofuran-3-yl |
| 143 | phenyl | 2-ethoxy-5-oxo-tetrahydrofuran-3-yl |
| 144 | 2-methylphenyl | 2-ethoxy-5-oxo-tetrahydrofuran-3-yl |
| 145 | 3-methylphenyl | 2-ethoxy-5-oxo-tetrahydrofuran-3-yl |
| 146 | 4-methylphenyl | 2-ethoxy-5-oxo-tetrahydrofuran-3-yl |
| 147 | 2-fluorophenyl | 2-ethoxy-5-oxo-tetrahydrofuran-3-yl |
| 148 | 3-fluorophenyl | 2-ethoxy-5-oxo-tetrahydrofuran-3-yl |
| 149 | 4-fluorophenyl | 2-ethoxy-5-oxo-tetrahydrofuran-3-yl |
| 150 | 2-chlorophenyl | 2-ethoxy-5-oxo-tetrahydrofuran-3-yl |
| 151 | 3-chlorophenyl | 2-ethoxy-5-oxo-tetrahydrofuran-3-yl |
| 152 | 4-chlorophenyl | 2-ethoxy-5-oxo-tetrahydrofuran-3-yl |
| 153 | 2-methoxyphenyl | 2-ethoxy-5-oxo-tetrahydrofuran-3-yl |
| 154 | 3-methoxyphenyl | 2-ethoxy-5-oxo-tetrahydrofuran-3-yl |
| 155 | 4-methoxyphenyl | 2-ethoxy-5-oxo-tetrahydrofuran-3-yl |
| 156 | 2-trifluoromethylphenyl | 2-ethoxy-5-oxo-tetrahydrofuran-3-yl |
| 157 | 3-trifluoromethylphenyl | 2-ethoxy-5-oxo-tetrahydrofuran-3-yl |
| 158 | 4-trifluoromethylphenyl | 2-ethoxy-5-oxo-tetrahydrofuran-3-yl |
| 159 | 3,4,5-trimethoxyphenyl | 2-ethoxy-5-oxo-tetrahydrofuran-3-yl |
| 160 | benzoyl | 2-ethoxy-5-oxo-tetrahydrofuran-3-yl |
| 161 | phenylamino | 2-ethoxy-5-oxo-tetrahydrofuran-3-yl |
| 162 | 2-phenylethyl | 2-ethoxy-5-oxo-tetrahydrofuran-3-yl |
| 163 | naphth-1-yl | 2-ethoxy-5-oxo-tetrahydrofuran-3-yl |
| 164 | naphth-2-yl | 2-ethoxy-5-oxo-tetrahydrofuran-3-yl |

| No. | R | R$^1$ |
|---|---|---|
| 121 | phenyl | 2-hydroxy-5-oxo-tetrahydrofuran-3-yl |
| 122 | 2-methylphenyl | 2-hydroxy-5-oxo-tetrahydrofuran-3-yl |
| 123 | 3-methylphenyl | 2-hydroxy-5-oxo-tetrahydrofuran-3-yl |
| 124 | 4-methylphenyl | 2-hydroxy-5-oxo-tetrahydrofuran-3-yl |
| 125 | 2-fluorophenyl | 2-hydroxy-5-oxo-tetrahydrofuran-3-yl |
| 126 | 3-fluorophenyl | 2-hydroxy-5-oxo-tetrahydrofuran-3-yl |
| 127 | 4-fluorophenyl | 2-hydroxy-5-oxo-tetrahydrofuran-3-yl |
| 128 | 2-chlorophenyl | 2-hydroxy-5-oxo-tetrahydrofuran-3-yl |
| 129 | 3-chlorophenyl | 2-hydroxy-5-oxo-tetrahydrofuran-3-yl |
| 130 | 4-chlorophenyl | 2-hydroxy-5-oxo-tetrahydrofuran-3-yl |
| 131 | 2-methoxyphenyl | 2-hydroxy-5-oxo-tetrahydrofuran-3-yl |
| 132 | 3-methoxyphenyl | 2-hydroxy-5-oxo-tetrahydrofuran-3-yl |
| 133 | 4-methoxyphenyl | 2-hydroxy-5-oxo-tetrahydrofuran-3-yl |
| 134 | 2-trifluoromethylphenyl | 2-hydroxy-5-oxo-tetrahydrofuran-3-yl |
| 135 | 3-trifluoromethylphenyl | 2-hydroxy-5-oxo-tetrahydrofuran-3-yl |
| 136 | 4-trifluoromethylphenyl | 2-hydroxy-5-oxo-tetrahydrofuran-3-yl |
| 137 | 3,4,5-trimethoxyphenyl | 2-hydroxy-5-oxo-tetrahydrofuran-3-yl |
| 138 | benzoyl | 2-hydroxy-5-oxo-tetrahydrofuran-3-yl |
| 139 | phenylamino | 2-hydroxy-5-oxo-tetrahydrofuran-3-yl |
| 140 | 2-phenylethyl | 2-hydroxy-5-oxo-tetrahydrofuran-3-yl |
| 141 | naphth-1-yl | 2-hydroxy-5-oxo-tetrahydrofuran-3-yl |
| 142 | naphth-2-yl | 2-hydroxy-5-oxo-tetrahydrofuran-3-yl |
| 143 | phenyl | 2-ethoxy-5-oxo-tetrahydrofuran-3-yl |
| 144 | 2-methylphenyl | 2-ethoxy-5-oxo-tetrahydrofuran-3-yl |
| 145 | 3-methylphenyl | 2-ethoxy-5-oxo-tetrahydrofuran-3-yl |
| 146 | 4-methylphenyl | 2-ethoxy-5-oxo-tetrahydrofuran-3-yl |
| 147 | 2-fluorophenyl | 2-ethoxy-5-oxo-tetrahydrofuran-3-yl |
| 148 | 3-fluorophenyl | 2-ethoxy-5-oxo-tetrahydrofuran-3-yl |
| 149 | 4-fluorophenyl | 2-ethoxy-5-oxo-tetrahydrofuran-3-yl |
| 150 | 2-chlorophenyl | 2-ethoxy-5-oxo-tetrahydrofuran-3-yl |
| 151 | 3-chlorophenyl | 2-ethoxy-5-oxo-tetrahydrofuran-3-yl |
| 152 | 4-chlorophenyl | 2-ethoxy-5-oxo-tetrahydrofuran-3-yl |
| 153 | 2-methoxyphenyl | 2-ethoxy-5-oxo-tetrahydrofuran-3-yl |
| 154 | 3-methoxyphenyl | 2-ethoxy-5-oxo-tetrahydrofuran-3-yl |
| 155 | 4-methoxyphenyl | 2-ethoxy-5-oxo-tetrahydrofuran-3-yl |
| 156 | 2-trifluoromethylphenyl | 2-ethoxy-5-oxo-tetrahydrofuran-3-yl |
| 157 | 3-trifluoromethylphenyl | 2-ethoxy-5-oxo-tetrahydrofuran-3-yl |
| 158 | 4-trifluoromethylphenyl | 2-ethoxy-5-oxo-tetrahydrofuran-3-yl |
| 159 | 3,4,5-trimethoxyphenyl | 2-ethoxy-5-oxo-tetrahydrofuran-3-yl |
| 160 | benzoyl | 2-ethoxy-5-oxo-tetrahydrofuran-3-yl |
| 161 | phenylamino | 2-ethoxy-5-oxo-tetrahydrofuran-3-yl |
| 162 | 2-phenylethyl | 2-ethoxy-5-oxo-tetrahydrofuran-3-yl |
| 163 | naphth-1-yl | 2-ethoxy-5-oxo-tetrahydrofuran-3-yl |
| 164 | naphth-2-yl | 2-ethoxy-5-oxo-tetrahydrofuran-3-yl |

The compounds of this category can be suitably prepared by the procedure outlined herein below, utilizing intermediate 3 (Type I Intermediates) which can be synthesized by the procedure outlined in Scheme VIII herein below.

Scheme VIII

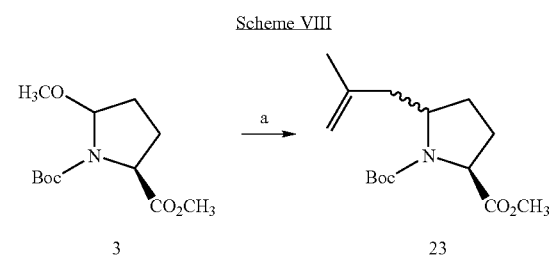

Reagents and Conditions (a) 2-Methyl-allyl-TMS, BF₃Et₂O, CH₂CL₂; -78° C. 2 hr.

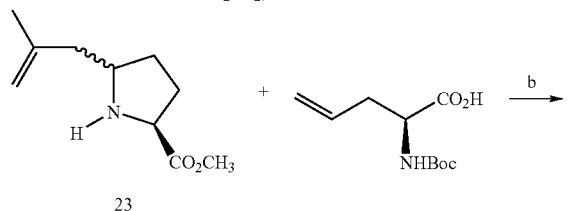

Reagents and Conditions (b) DCC, TEA, DMAP, CH₂Cl₂; rt 18 hr.

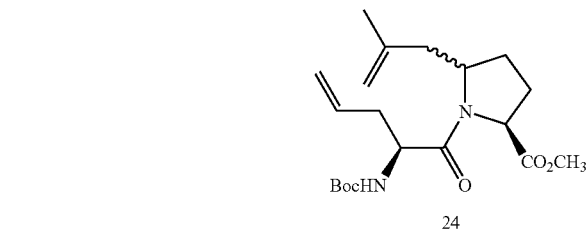

Reagents and Conditions (c) Grubbs' cat., CH₂Cl₂; reflux 4 hr.

Other examples of this category include the following compounds with the indicated stereochemistry.

9-Methyl-6-[(naphthalene-2-carbonyl)-amino]-5-oxo-1,2,3,5,6,7,10,10a-octahydropyrrolo[1,2-a]azocine-3-carboxylic acid(2-hydroxy-5-oxo-tetrahydro-furan-3-yl)-amide: $^1$H NMR (CD$_3$OD): δ 8.43 (m, 1H), 8.04–7.93 (m, 4H), 7.63 (m, 2H), 5.72 (ddd, J=15.6, 9.0, 6.6 Hz, 1H), 4.62 (dd, J=5.4, 3.3 Hz, 1H), 4.51 (dd, J=8.4, 4.8 Hz, 1H), 4.40–4.30 (m, 2H), 3.25 (m, 1H), 3.04 (m 2H), 2.84–2.71 (m, 1H), 2.57–2.42 (m, 3H), 2.21–1.94 (m, 7H), 1.92 (s, 3H); ESI MS 492.15 (M+H).

9-Methyl-5-oxo-6-(3-trifluoromethyl-benzoylamino)-1,2,3,5,6,7,10,10a-octahydro-pyrrolo[1,2-a]azocine-3-carboxylic acid (2-hydroxy-5-oxo-tetrahydro-furan-3-yl)-amide: $^1$H NMR (CD$_3$OD): δ 8.24 (s, 1H), 8.16 (d, J=8.1 Hz, 2H), 7.90 (d, J=7.5 Hz, 1H), 7.23 (t, J=8.0 Hz, 1H), 5.72 (m, 1H), 5.44 (m, 1H), 4.60 (dd, J=5.7, 3.3 Hz, 1H), 4.49 (dd, J=8.3, 4.7 Hz, 1H), 3.00 (m 2H), 2.83–2.68 (m, 1H), 2.57–2.38 (m, 3H), 2.21–1.85 (m, 8H), ESI MS 510.10 (M+H).

8-Methyl-5-oxo-6-(3-trifluoromethyl-benzoylamino)-1,2,3,5,6,7,10,10a-octahydro-pyrrolo[1,2-a]azocine-3-carboxylic acid (2-hydroxy-5-oxo-tetrahydro-furan-3-yl)-amide. $^1$H NMR (CD$_3$OD): δ 8.24 (s, 1H), 8.17 (d, J=8.1 Hz, 2H), 7.90 (d, J=7.5 Hz, 1H), 7.23 (t, J=8.0 Hz, 1H), 5.72 (m, 1H), 5.44 (m, 1H), 4.60 (dd, J=5.7, 3.3 Hz, 1H), 4.49 (dd, J=8.3, 4.7 Hz, 1H), 3.00 (m 2H), 2.83–2.68 (m, 1H), 2.57–2.38 (m, 3H), 2.21–2.05 (m, 3H), 1.97 (s, 3H), 1.94–1.85 (m, 2H) ESI MS 510.10 (M+H).

8-Methyl-6-[(naphthalene-2-carbonyl)-amino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide. $^1$H NMR (CD$_3$OD): δ 8.48 (s, 1H), 8.04–7.93 (m, 4H), 7.6–7.58 (m, 2H), 5.72 (m, 1H) 5.48 (ddd, J=15.6, 9.0, 6.6 Hz, 1H), 4.62 (dd, J=5.4, 3.3 Hz, 1H), 4.52 (dd, J=8.4, 4.8 Hz, 1H), 4.40–4.27 (m, 2H), 3.25 (m, 1H), 3.04 (m 2H), 2.81 (ddd, J=20.0, 15.6, 3.0 Hz, 1H), 2.57–2.42 (m, 3H), 2.21–1.94 (m, 7H), 1.92 (s, 3H); ESI MS 492.15 (M+H).

Other suitable linking units can be used to connect the R and R$^1$ units to the core 8,5-fused ring scaffold, for example, a urea linkage can be used to attached the R units of the present invention as depicted in Scheme IX herein below beginning with compound 8.

Scheme IX

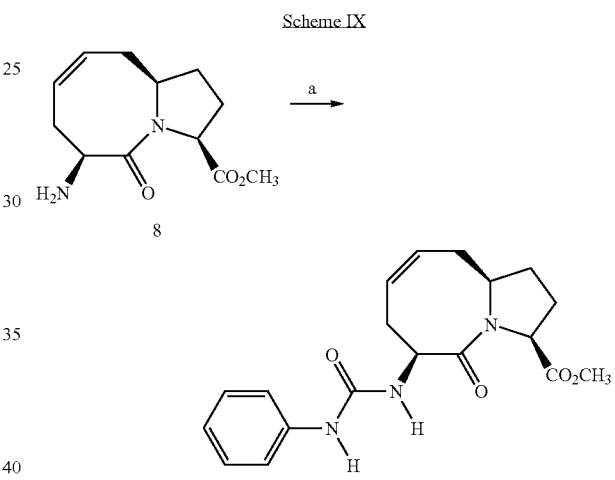

Reagents and Conditions (a) phenyl isocyanate, TEA., CH₂Cl₂; rt..

EXAMPLE 6

Preparation of 5-Oxo-6-(3-phenyl-ureido)-1,2,3,5,6,7,10,10a-octahydro-pyrrolo[1,2-a]azocine-3-carboxylic acid methyl ester (26): 6-Amino-5-oxo-1,2,3,5,6,7,10,10a-octahydro-pyrrolo[1,2-a]azocine-3-carboxylic acid methyl ester, 8, (120 mg, 0.5 mmol), phenyl isocyanate (110 μL, 1 mmol) and triethyl amine (200 μL) are stirred in CH₂Cl₂ (10 mL) at room temperature. After complete consumption of starting material, the reaction is poured into 1 N HCl; washed with brine; and dried of sodium sulfate. The organics are evaporated and the residue is purified over silica (40% ethyl acetate: hexane). The desired product is obtained as a clear oil. $^1$H NMR (CDCl$_3$): δ 7.81 (s, 1H), 7.35 (m, 2H), 7.23 (t, J=7.3 Hz, 2H), 6.98 (t, J=7.4 Hz, 1H), 6.85 (bs, 1H), 5.81 (m, 2H), 5.28 (m, 1H), 4.52 (dd, J=8.9, 2.5 Hz, 1H),4.27 (m, 1H), 3.58 (m, 3H), 2.95–2.82 (m, 2H), 2.45 (m, 1H), 2.29 (m, 1H), 2.16–1.96 (m, 4H). $^{13}$C NMR (CDCl$_3$): δ 173.0, 172.4, 155.8, 139.4, 129.1, 129.0, 126.2, 122.8, 119.9, 60.6, 58.9, 52.1, 51.3, 34.9, 33.1, 33.0, 27.5. ESI MS: 358.15 (M+H).

(3S,6S,10aS)-5-Oxo-6-(3-phenyl-ureido)-1,2,3,5,6,7,10, 10a-octahydro-pyrrolo[1,2-a]azocine-3-carboxylic acid (2-ethoxy-5-oxo-tetrahydro-furan-3-yl)-amide: ESI MS: 471.14 (M+H).

(3S,6S,10aS)-5-Oxo-6-(3-phenyl-ureido)-1,2,3,5,6,7,10, 10a-octahydro-pyrrolo[1,2-a]azocine-3-carboxylic acid (2-hydroxy-5-oxo-tetrahydro-furan-3-yl)-amide: $^1$H NMR (CDCl$_3$): δ 8.28 (bs, 1H), 7.52 (d, J=8.1 Hz, 2H), 7.43 (s, 1H), 7.27 (t, J=8.1 Hz, 2H), 6.96 (t, J=7.3 Hz, 1H), 6.27 (d, J=7.0 Hz, 1H), 5.85 (m, 3H), 5.19 (m, 1H), 4.71–4.32 (m, 3H), 3.09–2.78 (m, 5H), 2.42 (m, 2H), 2.21–1.89 (m, 5H). ESI MS: 443.1 (M+H).

The following are non-limiting representative examples of other analogs Categories according to the present invention.

9-Oxo-8-(3-phenyl-acryloylamino)-2,3,3a,4,7,8,9,9a-octahydro-1H-cyclopentacyclooctene-1-carboxylic acid (2-hydroxy-5-oxo-tetrahydro-furan-3-yl)-amide: $^1$H NMR (CDCl$_3$): δ 7.76–7.31 (m, 7H), 7.07 (m, 1H), 6.69–6.44 (m, 1H), 5.89–5.67 (m, 2H), 5.49 (m, 1H), 4.68 (m, 2H), 4.49–4.24 (m, 1H), 3.12–2.91 (m, 4H), 2.54–1.85 (m, 6H). ESI MS: 454.12 (M+H)

9-Oxo-8-(3-phenyl-propionylamino)-decahydro-cyclopentacyclooctene-1-carboxylic acid (2-hydroxy-5-oxo-tetrahydro-furan-3-yl)-amide: $^1$H NMR (CDCl3): δ 7.31–7.19 (m, 5H), 6.80–6.48 (m, 1H), 4.95 (m, 1H), 4.61 (m, 1H), 4.29 (m, 3H), 2.94 (m, 3H), 2.52 (m, 3H), 2.20 (m, 2H), 1.81–1.62 (m, 10H), 1.38–1.08 (m, 2H), 0.96–0.83 (m, 1H). ESI MS 458.17 (M+H).

5-Oxo-1,2,3,5,6,7,10,10a-octahydro-pyrrolo[1,2-a]azocine-3,6-dicarboxylic acid 6-benzylamide 3-[(2-ethoxy-5-oxo-tetrahydro-furan-3-yl)-amide]: $^1$H NMR (CDCl$_3$): δ 7.37–7.25 (m, 5H), 5.74 (m, 2H), 5.45–5.39 (m, 1H), 5.27 (m, 1H), 4.42 (m, 2H), 4.30 (m, 2H), 3.88–3.79 (m, 1H), 3.74–3.62 (m, 2H), 3.11–2.98 (m, 2H), 2.57–1.97 (m, 9H), 1.84–1.77 (m, 1H), 1.25 (m, 3H). $^{13}$C NMR (CDCl$_3$): δ 175.8, 173.4, 170.8, 169.8, 138.5, 130.4, 128.4, 127.5, 127.2, 127.1, 125.8, 125.7, 107.8, 107.6, 65.3, 62.6, 56.4, 56.2, 52.2, 52.1, 43.1, 34.2, 32.8, 32.5, 31.6, 29.0, 26.0, 14.1. ESI MS 470.18 (M+H).

5-Oxo-6-(3-phenyl-acryloylamino)-21,2,3,5,6,7,10,10a-octahydro-pyrrolo[1,2-a]azocine-3-carboxylic acid (2-hydroxy-5-oxo-tetrahydro-furan-3-yl)-amide: $^1$H NMR (CDCl$_3$): δ 7.76–7.31 (m, 7H), 7.07 (m, 1H), 6.69–6.44 (m, 1H), 5.89–5.67 (m, 2H), 5.49 (m, 1H), 4.68 (m, 2H), 4.49–4.24 (m, 1H), 3.12–2.91 (m, 4H), 2.54–1.85 (m, 6H). ESI MS: 454.12 (M+H).

5-Oxo-6-(2-oxo-2-phenyl-acetylamino)-1,2,3,5,6,7,10, 10a-octahydro-pyrrolo[1,2-a]azocine-3-carboxylic acid (2-hydroxy-5-oxo-tetrahydro-furan-3-yl)-amide: $^1$H NMR (CD$_3$CN): δ 8.21 (m, 2H), 7.98 (s, 1H), 7.86 (m, 1H), 7.80 (m, 1H), 7.20 (m, 1H), 6.02 (m, 2H), 5.43 (m, 1H), 4.61–4.48 (m, 3H), 4.32 (bs, 1H), 3.35 (m, 2H), 3.06 (m, 1H), 2.88 (m, 1H), 2.69–2.34 (m, 4H), 2.12 (m, 4H), $^{13}$C NMR (CD$_3$CN): δ 173.86, 171.01, 170.90, 163.04, 134.61, 133.65, 130.65, 130.07, 128.99, 127.23, 127.04, 101.91, 65.71, 59.10, 52.21, 50.69, 48.11, 33.52, 32.71, 32.64, 32.23, 27.11, 15.10; ESI MS 456.08 (M+H).

[3-(2-ethoxy-5-oxo-tetrahydro-furan-3-ylcarbamoyl)-5-oxo-1,2,3,5,6,7,10,10a-octahydro-pyrrolo[1,2-a]azocin-6-yl]-carbamic acid benzyl ester: $^1$H NMR (CD$_3$CN): δ 7.46–7.37 (m, 5H), 7.04 (m, 1H), 6.09 (m, 1H), 5.82–5.68 (m, 2H), 5.51 (m, 1H), 5.12 (m, 2H), 4.94 (m, 1H), 4.75–4.58 (m, 3H), 4.33 (m, 2H), 3.92–3.78 (m, 1H), 3.72–3.59 (m, 1H), 2.92 (m, 1H), 2.84–2.69 (m, 2H), 2.64–2.58 (m, 1H), 2.26 (m, 4H), 1.86 (m, 2H), 1.24 (m, 3H); $^{13}$C NMR (CD$_3$CN): δ 174.09, 172.06, 171.73, 156.17, 137.32, 129.57, 128.40, 127.90, 126.42, 117.61, 107.54, 102.20, 65.91, 62.45, 58.12, 52.14, 48.23, 33.58, 33.07, 32.51, 32.01, 27.52, 27.03, 22.07, 14.51; ESI MS 486.15 (M+H).

[3-(2-hydroxy-5-oxo-tetrahydro-furan-3-ylcarbamoyl)-5-oxo-1,2,3,5,6,7,10,10a-octahydro-pyrrolo[1,2-a]azocin-6-yl]-carbamic acid benzyl ester: $^1$H NMR (CD$_3$OD): δ 7.38 (m, 5H), 5.75 (m, 2H), 5.15 (m, 2H), 4.61 (m, 1H), 4.28 (m, 3H), 3.18 (m, 1H), 3.01 (m, 1H), 2.82–2.41 (m, 3H), 2.39–2.08 (m, 4H), 1.84 (m, 2H), 1.24 (m, 3H); ESI MS 458.09 (M+H).

6-(Isoquinolin-1-ylcarbamoyl)-5-oxo-1,2,3,5,6,7,10,10a-octahydro-pyrrolo[1,2-a]azocine-3-carboxylic acid 3-[(2-ethoxy-5-oxo-tetrahydro-furan-3-yl)-amide]: $^1$H NMR (CDCl$_3$): δ 8.71 (m, 1H), 8.09–7.70 (m, 4H), 6.00–5.87 (m, 2H), 5.48–5.25 (m, 3H), 4.6 (m, 2H), 4.23, (t, J=7.4 Hz, 1H), 3.94–3.83 (m, 1H), 3.73–3.62 (m, 2H), 3.08–2.93 (m, 3H), 2.47–2.41 (m, 6H), 1.31–1.23 (m, 3H). ESI MS 507.18 (M+H).

6-(Naphalen-2-ylcarbamoyl)-5-Oxo-1,2,3,5,6,7,10,10a-octahydro-pyrrolo[1,2-a]azocine-3-carboxylic acid 3-[(2-ethoxy-5-oxo-tetrahydro-furan-3-yl)-amide]: $^1$H NMR (CDCl$_3$): δ 11.24 (s, 1H), 8.20 (d, J=7.7 Hz), 8.06 (d, J=8.1 Hz, 1H), 7.88 (d, J=8.1 Hz, 1H), 7.68 (d, J=8.1 Hz, 1H), 7.61–7.47 (m, 3H), 7.31 (m, 1H), 5.89 (m, 2H), 5.51 (m, 1H), 4.86–4.76 (m, 2H), 4.31–4.15 (m, 2H), 3.96 (m, 1H), 3.70 (m, 1H), 3.39 (dd, J=16.1, 6.3, 1H), 3.15 (m, 1H), 2.92 (dd, J=18.0, 9.2, 1H), 2.75 (m, 1H), 2.55–2.23 (m, 4H), 2.13–1.93 (m, 2H), 1.30 (m, 3H). ESI Mass 506.17 (M+H).

9-Methyl-6-[(naphthalene-2-carbonyl)-amino]-5-oxo-1, 2,3,5,6,7,10,10a-octahydropyrrolo[1,2-a]azocine-3-carboxylic acid(2-hydroxy-5-oxo-tetrahydro-furan-3-yl)-amide: $^1$H NMR (CD$_3$OD): δ 8.43 (m, 1H), 8.04–7.93 (m, 4H), 7.63 (m, 2H), 5.72 (ddd, J=15.6, 9.0, 6.6 Hz, 1H), 4.62 (dd, J=5.4, 3.3 Hz, 1H), 4.51 (dd, J=8.4, 4.8 Hz, 1H), 4.40–4.30 (m, 2H), 3.25 (m, 1H), 3.04 (m 2H), 2.84–2.71 (m, 1H), 2.57–2.42 (m, 3H), 2.21–1.94 (m, 7H), 1.92 (s, 3H); ESI MS 492.15 (M+H).

9-Methyl-5-oxo-6-(3-trifluoromethyl-benzoylamino)-1,2, 3,5,6,7,10,10a-octahydro-pyrrolo[1,2-a]azocine-3-carboxylic acid (2-hydroxy-5-oxo-tetrahydro-furan-3-yl)-amide: $^1$H NMR (CD$_3$OD): δ 8.24 (s, 1H), 8.16 (d, J=8.1 Hz, 2H), 7.90 (d, J=7.5 Hz, 1H), 7.23 (t, J=8.1 Hz, 1H), 5.72 (m, 1H), 5.44 (m, 1H), 4.60 (dd, J=5.7, 3.3 Hz, 1H), 4.49 (dd, J=8.3, 4.7 Hz, 1H), 3.00 (m 2H), 2.83–2.68 (m, 1H), 2.57–2.38 (m, 3H), 2.21–1.85 (m, 8H), ESI MS 510.10 (M+H).

The cysteine traps of the present invention can be prepared by any convenient method selected by the formulator. The following is a description of the preparation of (2-ethoxy-5-oxo-tetrahydrofuran-3-yl)-carbamic acid allyl ester which is used to introduce one category of cysteine trap into the scaffolds of the present invention.

Scheme X

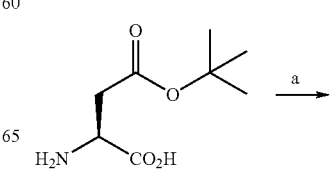

-continued

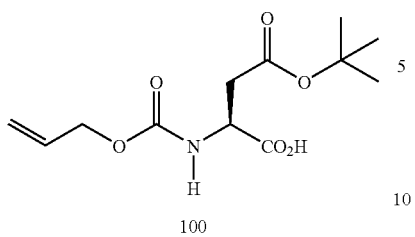
100

Reagents and conditions: (a) allyl chloroformate, NaHCO₃, THF/H₂O (3:1).

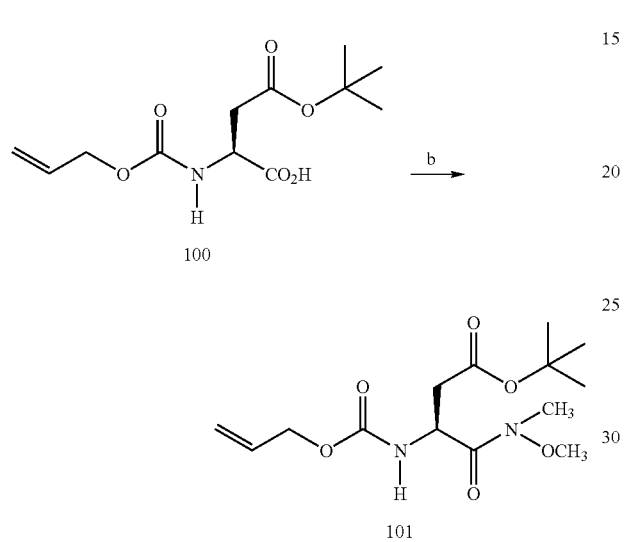
101

Reagents and conditions: (b) H₃CONHCH₃, NMM, EDCl, CH₂Cl₂.

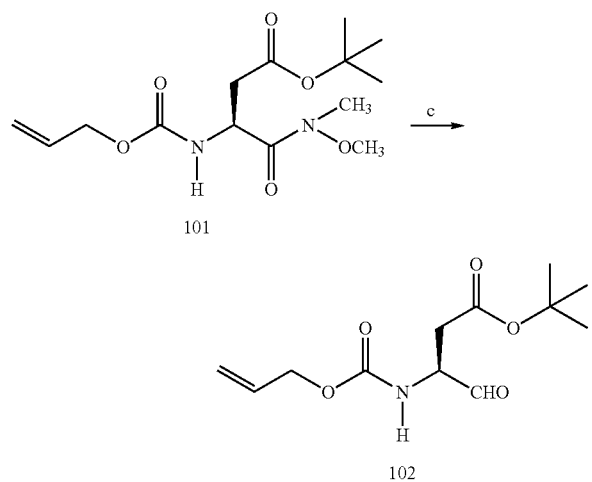
102

Reagents and conditions: (c) LAH, THF/H₂O (3:1).

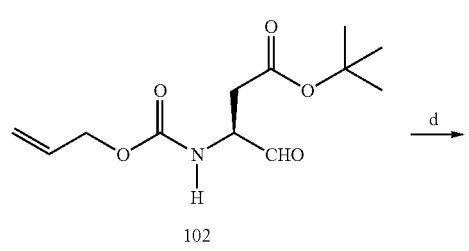

-continued

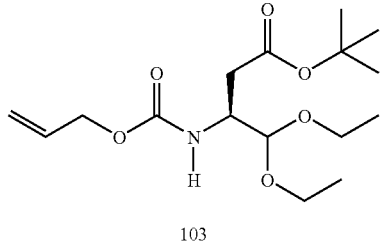
103

Reagents and conditions: (d) CH(OC₂H₅)₃, PTSA, EtOH.

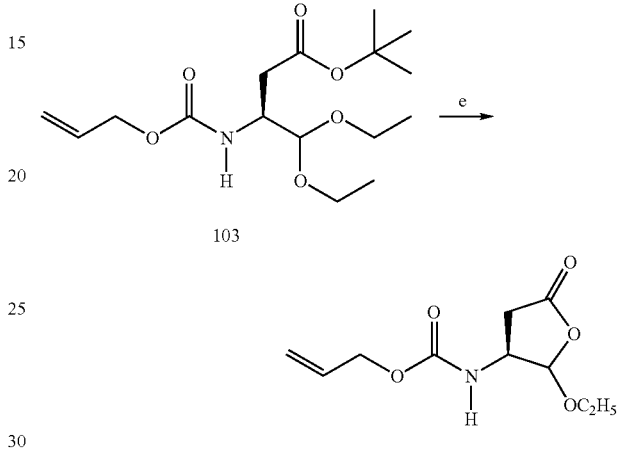
104

Reagents and conditions: (e) TFA, CH₂Cl₂.

EXAMPLE 7

(2-Ethoxy-5-oxo-tetrahydro-furan-3-yl)-carbamic acid allyl ester (104)

Preparation of 2-allyloxycarbonylamino-succinic acid 4-tert-butyl ester (100): L-aspartic acid □-t-butyl ester (30.3 g, 0.160 mol) is dissolved in 100 mL THF and 300 mL H₂O. Under cooling (ice bath) and with stirring, allyl chloroformate (38.8 mL, 44.1 g, 0.365 mol) and sodium bicarbonate (60.1 g, 0.715 mol) are added in one portion. After the consumption of the starting material, the mixture is acidified to a pH of 2 using 6 N HCl and then extracted with ether (3×400 mL). The ether layer is dried with MgSO₄ and concentrated under reduced pressure. The residue is purified over silica (CH₂Cl₂/MeOH/acetic acid 3:97:0.1) to furnish 40.7 g (90% yield) of the desired product as a clear oil. ¹H-NMR (300 MHz, CDCl₃): δ 1.46 (s, 9H), 2.76–3.03 (ABX, J=59.3, 17.2, 4.4, 2H), 4.60–4.66 (br m, 3H), 5.30 (m, 2H), 5.82–5.84 (d, J=8.4), 5.87–6.00 (m, 1H), 10.94 (br s, 1H); MS (ESI): m/e=274.08 (M+H).

Preparation of 3-allyloxycarbonylamino-N-methoxy-N-methyl-succinamic acid tert-butyl ester (101): 2-Allyloxy-carbonylamino-succinic acid 4-tert-butyl ester, 100, (43.4 g, 0.159 mol) is dissolved in CH₂Cl₂(900 mL). To this solution O,N-dimethyl-hydroxylamine hydrochloride (18.6 g, 0.191 mol), 4-Methyl-morpholine (21.0 mL, 19.3 g, 0.191 mol), and 1-(3-Dimethylaminopropyl)-3-ethylcarbodiimide hydrochloride (36.6 g, 0.191 mol) are added. After the consumption of the starting material, the solution is washed with 1.0 N HCl (2×400 mL) and brine (1×250 mL). The organic layer is concentrated in vacuo and the residue purified over silica (hexanes/ethyl acetate 65:35) to afford 40.8 g (81% yield) of the desired product as a clear oil. ¹H-NMR, (300 MHz, CDCl₃): δ 1.43 (s, 9H), 2.50–2.74 (m, 2H), 3.22 (s, 3H), 3.79 (s, 3H), 4.55–4.57 (d, J=4.8, 2H), 4.97–5.04 (m, 1H), 5.17–5.32 (m, 2H), 5.67–5.70 (d, J=9.0, 1H), 5.83–5.94 (m, 1H); $^{13}$C-NMR (75.5 MHz, CDCl$_3$): δ 28.20, 32.58, 38.48, 61.83, 65.93, 81.53, 117.85, 132.88, 155.84, 169.46, 171.83; MS (ESI): m/e=317.11 (M+H).

Preparation of 3-allyloxycarbonylamino-4-oxo-butyric acid tert-butyl ester (102): A solution of 3-allyloxycarbonylamino-N-methoxy-N-methyl-succinamic acid tert-butyl ester, 101, (24.3 g, 76.8 mmol) in THF (60 mL) is treated at −78° C. with lithium aluminum hydride (1 M in THF, 39 mL, 39 mmol) dissolved in ether (200 mL) over 5 minutes. After the consumption of starting material, the solution is cautiously quenched with 1.0 N HCl, washed with 1.0 N HCl (2×100 mL) and brine (1×150 mL). The organic layer is concentrated in vacuo to afford 18.2 g (91% yield) of the desired product as a clear oil. $^1$H-NMR, (300 MHz, CDCl$_3$): δ 1.45 (s, 9H), 2.75–3.01 (m, 2H), 4.37–4.42 (m, 1H), 4.62–4.64 (d, J=5.4, 2H), 5.25–5.38 (m, 2H), 5.89–6.02 (m, 2H), 9.68 (s, 1H); MS (ESI): m/e=258.11 (M+H).

Preparation of 3-allyloxycarbonylamino-4,4-diethoxy-butyric acid tert-butyl ester (103): To a solution of 3-allyloxycarbonylamino-4-oxo-butyric acid tert-butyl ester, 102, (13.3 g, 51.7 mmol) in anhydrous ethanol (75 mL) is added ethyl orthoformate (45 mL, 0.270 mol), p-toluenesulfonic acid (0.15 g, cat.) and 4 Å molecular sieves (10 g, kiln dried) under N$_2$. After the consumption of starting material, the sieves are removed by filtration and the solvent removed in vacuo to provide the desired compound as a clear oil which is used directly without further purification. MS (ESI): m/e=332.21 (M+H).

Preparation of (2-ethoxy-5-oxo-tetrahydro-furan-3-yl)-carbamic acid allyl ester (104). A solution of the crude 3-Allyloxycarbonylamino-4,4-diethoxy-butyric acid tert-butyl ester, 103, obtained in the procedure above, in CH$_2$Cl$_2$ (50 mL) is treated with triflouroacetic acid (50 mL). After the consumption of starting material, the organics are reduced under vacuum. The residual triflouroacetic acid is removed with ethyl acetate by azeotroping conditions. The final residue is purified over silica (hexanes/ethyl acetate 80:20) to afford 10.1 g (85% yield) of the desired product as a slightly yellow oil. $^1$H-NMR, (300 MHz, CDCl$_3$): δ 1.23 (m, 3H), 2.41–2.54 (m, 1H), 2.82–3.06 (m, 2H), 3.61–3.73 (m, 1H), 3.82–3.98 (m, 1H), 4.06–4.25 (m, 1H), 4.61 (br s, 2H), 5.24–5.53 (m, 3H), 5.86–6.01 (m, 1H); MS (ESI): m/e=230.03 (M+H).

In the above Scheme X, intermediate 102 can be converted to the bio-equivalent form of the trap wherein R$^5$ is benzyl by the process outlined in Scheme XI.

Scheme XI

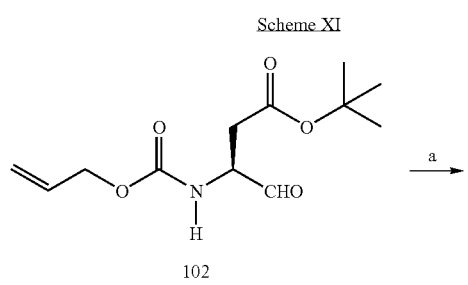

102

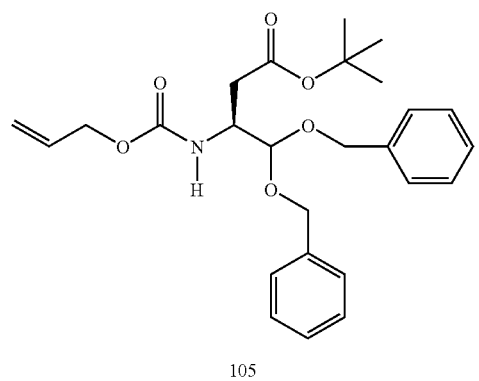

105

Reagents and conditions: (d) benzyl alcohol, TsOH, 3 Å sieves.

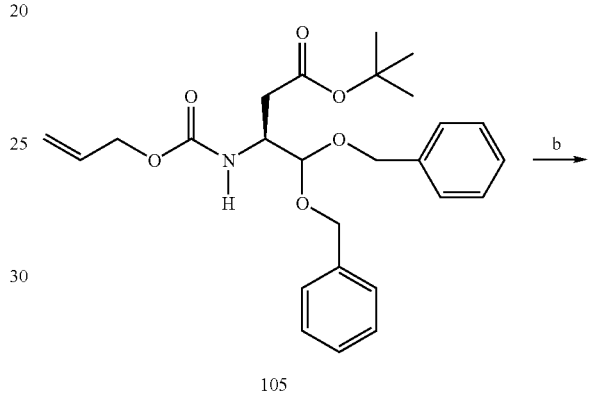

105

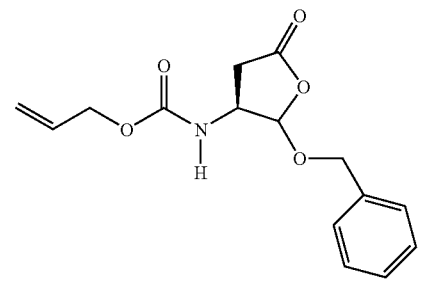

106

Reagents and conditions: (b) TFA, CH$_2$Cl$_2$.

Details for converting intermediate 102 to the bio-equivalent cysteine trap 106 can be found in K. T. Chapman *Bioorg. Med Chem. Lett.*, 2, 613–618 (1992) incorporated herein by reference.

Another category of reversible cysteine traps according to the present invention relates to units wherein J is an alkylenearyl unit having the formula —(CH)$_x$R$^{21}$. Scheme XII summarizes the preparation of a cysteine trap wherein R$^{21}$ is benzyl. For a more complete description of the preparation of bio-equivalent forms of cysteine traps comprising the second iteration of the second aspect of reversible traps according to the present invention see Adrian M. M. Mjalli et al., *Bioorg. Med Chem. Lett.*, 3, 2689–2692 (1993) incorporated herein by reference.

Scheme XII

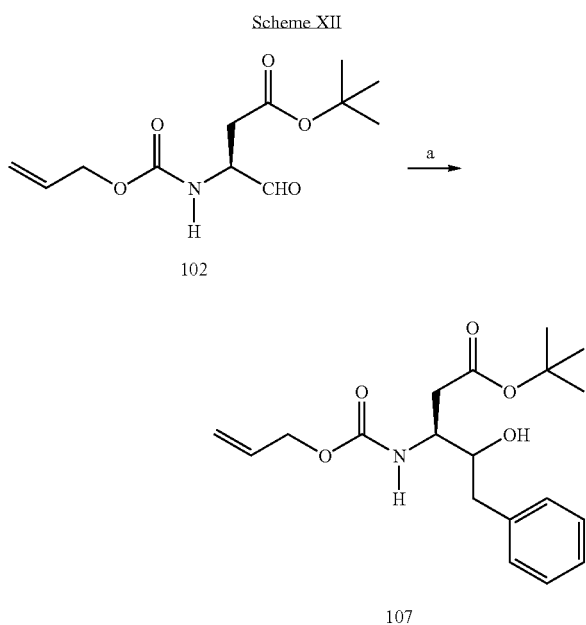

107

Reagents and conditions: (a) Benzylmagnesium chloride, THF; -78° C.

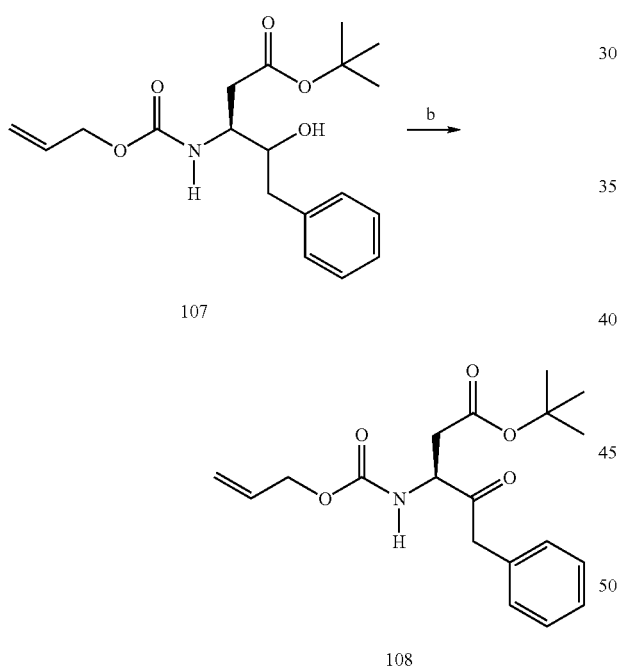

108

Reagents and conditions: (b) Dess-Martin reagent, CH₂Cl₂; rt, 1 hr..

Preparation of 3-allyloxycarbonylamino-4-hydroxy-5-phenyl-pentanoic acid tert-butyl ester (107): To a solution of benzylmagnesium chloride (20 mL, 20 mmol) in THF at −78° C. is added dropwise a 0° C. solution of 3-allyloxycarbonylamino-4-oxo-butyric acid tert-butyl ester, 102, (5.14 g, 20 mmol) in THF (100 mL). Once the addition is complete, the solution is allowed to warm to 0° C. over 30 minutes then the reaction mixture is poured into a beaker of crushed ice. The solution is extracted ×3 with CH₂Cl₂ (100 mL), the organic layers combined, dried over Na₂SO₄ and concentrated in vacuo to afford the desired product which is used without further purification.

Preparation of 3-allyloxycarbonylamino-4-oxo-5-phenyl-pentanoic acid tert-butyl ester (108): A solution of 3-allyloxycarbonylamino-4-hydroxy-5-phenyl-pentanoic acid tert-butyl ester, 107, (0.8 g, 2.23 mmol) in CH₂Cl₂ (10 mL) is added to a solution of Dess-Martin reagent (1.05 g, 2.47 mmol) in CH₂Cl₂ (10 mL). After 1 hour the reaction solution is diluted with ether (50 mL) and the solution poured into a 1.3 M solution of NaOH (20 mL). Stir for 1 hour and decant the organic layer. Dry the organic layer over Na₂SO₄, concentrate in vacuo to afford a crude residue that is purified over silica to afford the desired product.

Intermediate 108 can be directly coupled to the desired scaffold. Once coupled the formulator may choose to hydrolyze the tert-butyl ester moiety (bio-equivalent form) to the free acid (bio-active form) or convert the ester to another bio-equivalent form.

The traps of the present invention further include irreversible traps such as aryloxymethyl ketones. Scheme XIII outlines a procedure for preparing an aryloxy-methyl ketone trap intermediate which can be coupled to a scaffold according to the present invention by standard procedures known to those of ordinary skill in the art.

Scheme XIII

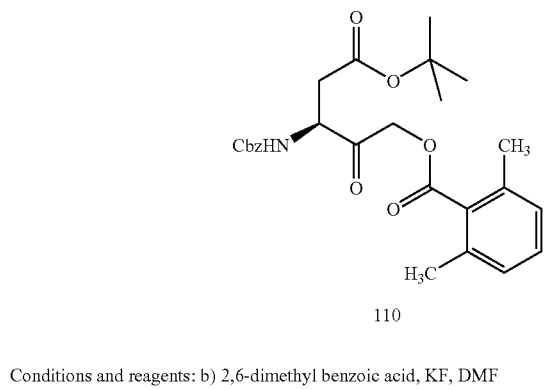

Conditions and reagents: a) EtOC(O)Cl; CH₂N₂; HBr

Conditions and reagents: b) 2,6-dimethyl benzoic acid, KF, DMF

-continued

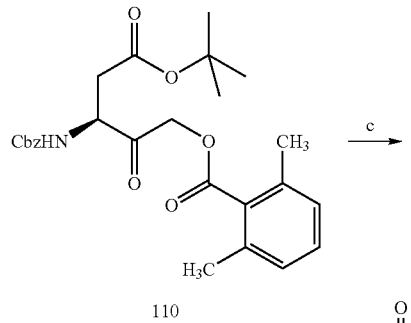

110

Conditions and reagents: c) H₂, Pd/C, EtOH, 1 N HCl

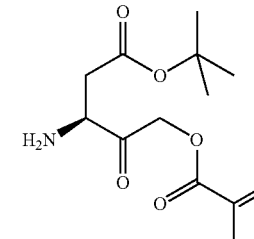

111

111
+

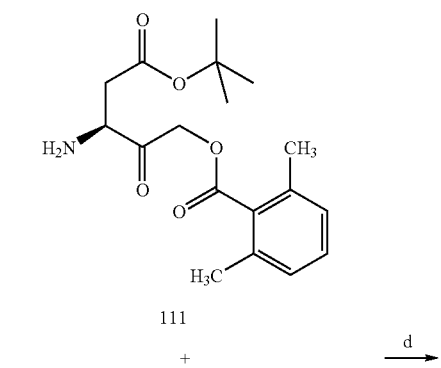

112

Conditions and reagents: d) EDCl, HOBt, Et₃N, CH₂Cl₂

-continued

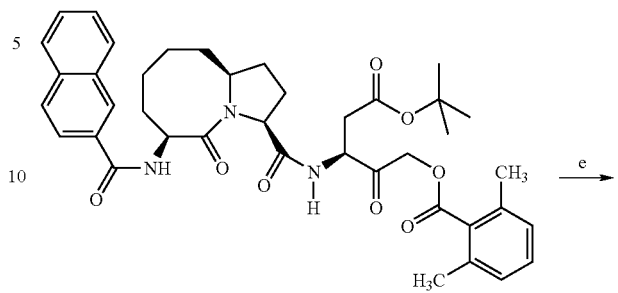

112

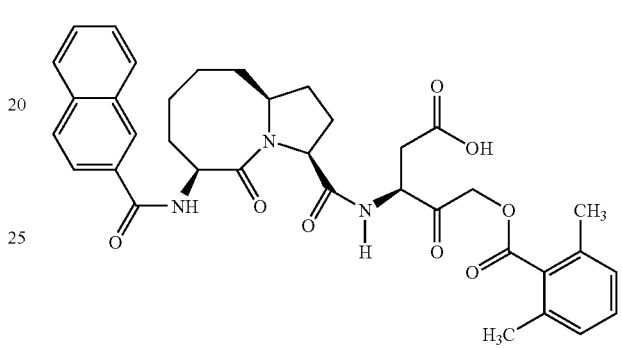

113

Conditions and reagents: e) TFA, CH₂Cl₂

EXAMPLE 8

2,6-Dimethyl-benzoic acid 4-carboxy-3-({6-[(naphthalene-2-carbonyl)-amino]-5-oxo-1,2,3,5,6,7,10,10a-octahydro-pyrrolo[1,2-a]azocine-3-carbonyl}-amino)-2-oxo-butyl ester (113)

Preparation of 3-benzyloxycarbonylamino-5-bromo-4-oxo-pentanoic acid tert-butyl ester (109): To a solution containing Z-Asp(OtBu)-OH (12.92 g, 40 mmol) and 4-methylmorpholine (5.6 g, 56 mmol) in 250 mL of THF at −20 C. is added ethyl chloroformate (5.0 mL, 52 mmol). The solution is stirred at −20 C. for 20 min and then excess CH₂N₂ (an ethereal solution, freshly prepared from N-nitrosomethyl urea and dried over KOH) is added and the solution is warmed to rt. After stirring at rt for 2 h, the solution is cooled to −20 C. and treated with HBr (80 mL of a 33% solution in HOAc). The reaction is stirred for an additional 20 min, treated with 200 mL of H₂O, and diluted with EtOAc. The organic layer is separated, washed with water, saturated NaHCO₃, and brine, and dried over MgSO₄. The solution is filtered, concentrated, and purified by flash chromatography on silica gel (hexane/EtOAc) to yield 11.6 g of the desired product. ¹H NMR (CDCl₃) □ 7.40 (br s, 5H), 5.91 (d, J=8.8 Hz, 1H), 5.18 (s, 2H), 4.78 (m, 1H), 4.22 (s, 2H), 3.01 (dd, J=17.2, 4.8 Hz, 1H), 2.78 (dd, J=17.2, 4.8 Hz, 1H), 1.45 (s, 9H).

Preparation of 2,6-dimethyl-benzoic acid 3-benzyloxycarbonylamino-4-tert-butoxycarbonyl-2-oxo-butyl ester (110): A heterogeneous solution containing 3-benzyloxycarbonylamino-5-bromo-4-oxo-pentanoic acid tert-butyl ester, 109, (9.89 g, 24.7 mmol), 2,6-dimethyl benzoic acid (4.45 g, 29.6 mmol), and KF (3.58 g, 61.8 mmol) in 250 mL of DMF is stirred at rt for 12 h. The solution is diluted with EtOAc, washed with water, saturated NaHCO₃, and brine, dried (MgSO₄), and concentrated in vacuo. Purification of the crude material by flash chromatography on silica gel (hexane/EtOAc) yields 11.3 g of the desired product as a white solid.

Preparation of 2,6-dimethyl-benzoic acid 3-amino-4-tert-butoxycarbonyl-2-oxo-butyl ester (111): 2,6-Dimethyl-benzoic acid 3-benzyloxycarbonylamino-4-tert-butoxycarbonyl-2-oxo-butyl ester, 110, (11.3 g, 24.1 mmol) is dissolved in a solution of EtOH (400 mL) and 1 N HCl (29 mL), treated with 10% Pd/C (500 mg) and stirred under a hydrogen atmosphere for 4 h. The solution is filtered and concentrated to yield 7.6 g of the desired product as an HCl salt that was used without further purification.

Preparation of 2,6-dimethyl-benzoic acid 4-tert-butoxycarbonyl-3-({6-[(naphthalene-2-carbonyl)-amino]-5-oxo-1,2,3,5,6,7,10,10a-octahydro-pyrrolo[1,2-a]azocine-3-carbonyl}-amino)-2-oxo-butyl ester (112): To a solution of 6-[(naphthalene-2-carbonyl)-amino]-5-oxo-1,2,3,5,6,7,10,10a-octahydro-pyrrolo[1,2-a]azocine-3-carboxylic acid, (124 mg, 0.33 mmol) in dichloromethane is added EDCI (191 mg, 1 mmol), 2,6-dimethyl-benzoic acid 3-amino-4-tert-butoxycarbonyl-2-oxo-butyl ester, 111, (200 mg, 0.62 mmol), and triethylamine (150 ul). After consumption of the starting material, the reaction is washed with 1N HCl (1×50 ml), water (1×50 ml), and brine (1×50 ml). The CHCl₂ is reduced in vacuo. The residue is used directly in the next step without purification. ESI MS 696.1 (M+H).

Preparation of 2,6-dimethyl-benzoic acid 4-carboxy-3-({6-[(naphthalene-2-carbonyl)-amino]-5-oxo-1,2,3,5,6,7,10,10a-octahydro-pyrrolo[1,2-a]azocine-3-carbonyl}-amino)-2-oxo-butyl ester (113): To a solution of 2,6-dimethyl-benzoic acid 4-tert-butoxycarbonyl-3-({6-[(naphthalene-2-carbonyl)-amino]-5-oxo-1,2,3,5,6,7,10,10a-octahydro-pyrrolo[1,2-a]azocine-3-carbonyl}-amino)-2-oxo-butyl ester, 112, (188 mg 0.27 mmol) is treated with solution of trifluoroacetic acid (10 ml) and dichloromethane (10 ml). The mixture is stirred for 2 hours and solvent is removed in vacuo. The residue is purified over silica (dichloromethane/methanol 95:5) to afford 120 mg of the desired product as a white solid. ¹H NMR (CDCl₃): δ 8.32 (d, J=5.9 Hz, 1H), 7.84 (m, 4H), 7.71 (m, 1H), 7.51 (m, 2H), 7.23 (dd, J-16.1, 8.1 Hz, 1H), 7.04 (t, J=7.4 Hz, 1H), 5.87 (m, 2H), 5.65 (m, 2H), 5.13–4.80 (m, 3H), 4.51 (m, 1H), 4.24 (m, 1H), 3.02–2.86 (m, 4H), 2.37 (s, 6H), 2.43–1.83 (m, 5H). ¹³C NMR (CDCl₃): δ 200.4, 200.1, 174.2, 172.9, 171.6, 171.4, 169.3, 167.6, 135.9, 135.1, 132.7, 131.2, 130.8, 129.9, 129.3, 128.7, 128.4, 128.3, 127.9, 127.0, 126.1, 125.7, 123.9, 66.9, 62.3, 61.7, 59.4, 59.1, 53.2, 52.9, 50.8, 35.3, 34.4, 34.2, 33.3, 32.2, 27.4, 26.9, 20.1. (excess carbons due to rotamers). ESI MS 639.69 (M+H).

The following is a further example of the preparation of a cysteine trap according to the present invention, wherein said trap is assembled while attached to the main scaffold as outlined in Scheme XIV below.

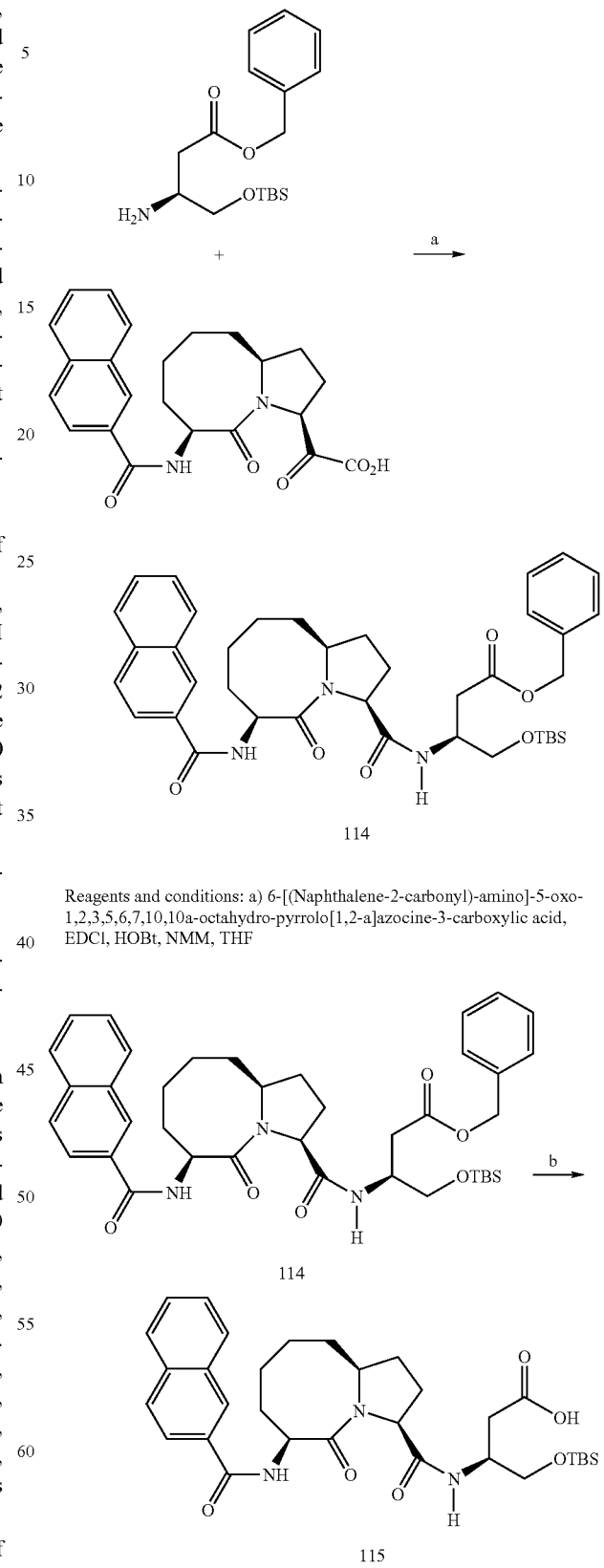

Scheme XIV

Reagents and conditions: a) 6-[(Naphthalene-2-carbonyl)-amino]-5-oxo-1,2,3,5,6,7,10,10a-octahydro-pyrrolo[1,2-a]azocine-3-carboxylic acid, EDCl, HOBt, NMM, THF Reagents and conditions: b) NaOH, MeOH

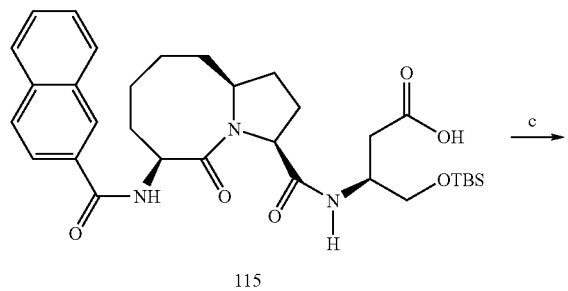

115

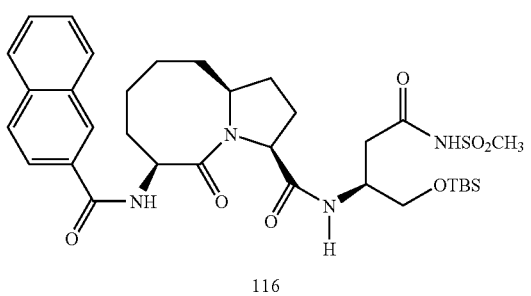

116

Reagents and conditions: c) CDI, methane sulfonamide, DBU, THF

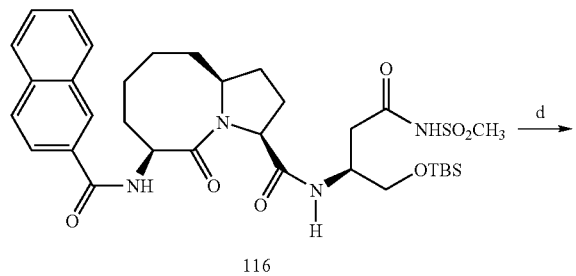

116

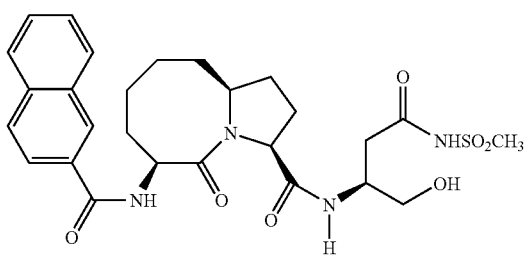

117

Reagents and conditions: d) HF/pyridine, THF

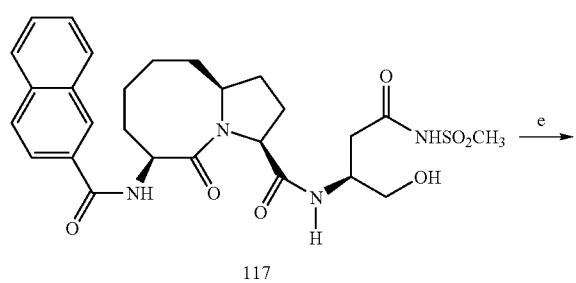

117

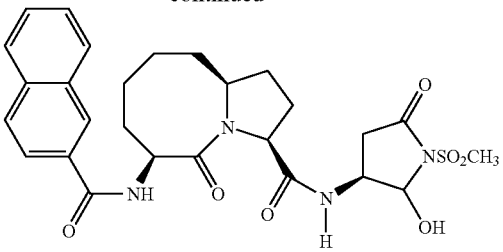

118

Reagents and conditions: e) Dess-Martin reagent, CH$_2$Cl$_2$

EXAMPLE 9

Preparation of 6-[(Naphthalene-2-carbonyl)-amino]-5-oxo-1,2,3,5,6,7,10,10a-octahydro-pyrrolo[1,2-a]azocine-3-carboxylic acid (2-hydroxy-1-methanesulfonyl-5-oxo-pyrrolidin-3-yl)-amide (118)

Preparation of 4-(tert-Butyl-dimethyl-silanyloxy)-3-({6-[(naphthalene-2-carbonyl)-amino]-5-oxo-1,2,3,5,6,7,10,10a-octahydro-pyrrolo[1,2-a]azocine-3-carbonyl}-amino)-butyric acid benzyl ester: A solution containing 6-[(Naphthalene-2-carbonyl)-amino]-5-oxo-1,2,3,5,6,7,10,10a-octahydro-pyrrolo[1,2-a]azocine-3-carboxylic acid (425 mg, 1.12 mmol), EDCI (240 mg, 1.25 mmol), HOBt (170 mg, 1.25 mmol), and NMM (0.15 mL, 1.25 mmol) in THF (15 mL) is stirred at rt for 20 min. A solution of 3-Amino-4-(tert-butyl-dimethyl-silanyloxy)-butyric acid benzyl ester (400 mg, 1.25 mmol, prepared by methods outlined in *Chem. Pharm. Bull.* 1999, 47, 11–21) in 5 mL of THF is added and the solution is stirred at rt for 12 h. The solution is poured into water and the aqueous solution is extracted with EtOAc. The combined organic extracts are washed with saturated NaHCO$_3$ and brine, dried (Na$_2$SO$_4$), filtered, concentrated, and purified by flash chromatography on silica gel (hexane/EtOAc) to yield 520 mg of desired product. $^1$H NMR (CDCl$_3$) δ 8.33 (s, 1H), 7.88 (m, 4H), 7.56 (m, 3H), 7.36 (m, 4H), 7.14 (d, J=8.4 Hz, 1H), 5.86 (m, 1H), 5.75 (m, 1H), 5.46 (m, 1H), 5.13 (s, 2H), 4.63 (d, J=7.5 Hz, 1H), 4.40 (m, 1H), 5.75 (m, 1H), 5.46 (m, 1H), 5.13 (s, 2H), 4.63 (d, J=13.5 Hz, 1H), 2.94 (m, 1H), 2.75–2.56 (m, 2H), 2.37–2.21 (m, 2H), 2.10–1.70 (m, 3H), 0.93 (s, 9H), 0.08 (s, 3H), 0.07 (s, 3H).

Preparation of 4-(tert-Butyl-dimethyl-silanyloxy)-3-({6-[(naphthalene-2-carbonyl)-amino]-5-oxo-1,2,3,5,6,7,10,10a-octahydro-pyrrolo[1,2-a]azocine-3-carbonyl}-amino)-butyric acid: A solution containing 4-(tert-Butyl-dimethyl-silanyloxy)-3-({6-[(naphthalene-2-carbonyl)-amino]-5-oxo-1,2,3,5,6,7,10,10a-octahydro-pyrrolo[1,2-a]azocine-3-carbonyl}-amino)-butyric acid benzyl ester (590 mg, 0.86 mmol) in MeOH (10 mL) is treated with 1N NaOH (2.5 mL) and stirred at rt for 12 hrs. The solution was poured into water, acidified to pH=3 with 10% citric acid, and extracted with EtOAc. The combined organic extracts are washed with brine and dried over Na$_2$SO$_4$. The solution is filtered and concentrated to yield 492 mg of desired product that was used without further purification. MS (ESI) 594 (M+1).

Preparation of 6-[(Naphthalene-2-carbonyl)-amino]-5-oxo-1,2,3,5,6,7,10,10a-octahydro-pyrrolo[1,2-a]azocine-3-carboxylic acid [1-(tert-butyl-dimethyl-silanyloxymethyl)-3-methanesulfonylamino-3-oxo-propyl]-amide: To a solution of 4-(tert-Butyl-dimethyl-silanyloxy)-3-({6-[(naphthalene-2-carbonyl)-amino]-5-oxo-1,2,3,5,6,7,10,10a-octahydro-pyrrolo[1,2-a]azocine-3-carbonyl}-amino)-butyric acid (220 mg, 0.37 mmol) in THF (6 mL) was added CDI (120 mg, 0.74 mmol) and the resulting solution was stirred at rt for 3 h. The solution is cooled to 0 C. and then methane sulfonamide (35 mg, 0.37 mmol) and DBU (0.11 mL) are added. The solution is warmed to rt, stirred at that temperature for an additional 3 h, and concentrated in vacuo. The crude residue is purified by flash chromatography on silica gel ($CH_2Cl_2$/MeOH) to obtain 160 mg of desired product. $^1$H NMR ($CDCl_3$) δ 8.42 (s, 1H), 8.0–7.87 (m, 3H), 7.73 (d, J=7.2 Hz, 1H), 7.57 (m, 2H), 7.10 (m, 1H), 5.94 (m, 1H), 5.85 (m, 1H), 5.50 (m, 1H), 4.47 (m, 1H), 4.36–4.20 (m, 2H), 3.76–3.62 (m, 2H), 3.30–1.67 (series of m, 10 H), 3.10 (br s, 3H), 0.91 (s, 9H), 0.08 (s, 3H), 0.07 (s, 3H).

Preparation of 6-[(Naphthalene-2-carbonyl)-amino]-5-oxo-1,2,3,5,6,7,10,10a-octahydro-pyrrolo[1,2-a]azocine-3-carboxylic acid (1-hydroxymethyl-3-methanesulfonylamino-3-oxo-propyl)-amide: To a solution of 6-[(Naphthalene-2-carbonyl)-amino]-5-oxo-1,2,3,5,6,7,10,10a-octahydro-pyrrolo[1,2-a]azocine-3-carboxylic acid [1-(tert-butyl-dimethyl-silanyloxymethyl)-3-methanesulfonylamino-3-oxo-propyl]-amide (160 mg, 0.24 mmol) in THF (6 mL) at 0 C. is added HF in pyridine (0.3 mL). The solution is stirred at 0 C. for 1 h, poured into pH=7 phosphate buffer, and extracted with $CH_2Cl_2$. The combined organic extracts are washed with brine, dried ($Na_2SO_4$), filtered, and concentrated. The crude residue obtained is purified by flash chromatography on silica gel ($CH_2Cl_2$/MeOH) to yield 86 mg of desired product. $^1$H NMR ($CDCl_3$) δ 8.34 (s, 1H), 7.91–7.79 (m, 4H), 7.49 (m, 2H), 7.09 (d, J=8.4 Hz, 1H), 5.88 (m, 2H, 5.45 (m, 1H), 4.43 (m, 1H), 4.20 (m, 2H), 3.04 (s, 3H), 3.80–1.80 (series of m, 12H).

Preparation of 6-[(Naphthalene-2-carbonyl)-amino]-5-oxo-1,2,3,5,6,7,10,10a-octahydro-pyrrolo[1,2-a]azocine-3-carboxylic acid (2-hydroxy-1-methanesulfonyl-5-oxo-pyrrolidin-3-yl)-amide: Dess-Martin reagent (90 mg, 0.21 mmol) is added to an ice cold solution of 6-[(Naphthalene-2-carbonyl)-amino]-5-oxo-1,2,3,5,6,7,10,10a-octahydro-pyrrolo[1,2-a]azocine-3-carboxylic acid (1-hydroxymethyl-3-methanesulfonylamino-3-oxo-propyl)-amide (48 mg, 0.09 mmol) in $CH_2Cl_2$ (5 mL). The solution is stirred at 0 C. for 2 h and treated with saturated $NaHCO_3$. The resulting solution is extracted with EtOAc and the combined organic extracts are washed with brine, dried ($Na_2SO_4$), filtered, and concentrated. The crude residue obtained is purified by flash chromatography on silica gel ($CH_2Cl_2$/MeOH) to yield 27 mg of product as a mixture of diastereomers. MS (ESI) 555 (M+1).

FORMULATIONS

The present invention also relates to compositions or formulations which comprise the interleukin-1β converting enzyme inhibitors according to the present invention. In general, the compositions of the present invention comprise:
 a) an effective amount of one or more interleukin-1β converting enzyme inhibitors according to the present invention; and
 b) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

METHOD OF USE

The present invention also relates to methods for controlling the activity of Caspase enzymes. Caspase enzymes are responsible for mediating the extracellular release of cytokines. Because the control of Caspase enzyme activity directly affects a number of disease states and disease processes in humans and higher mammals, the present invention also comprises a method for controlling a number of diseases found to afflict humans and higher mammals.

The first aspect of the methods of the present invention relate to methods for mediating and controlling the extracellular release of the cytokine interleukin-1β. This cytokine activity is modulated by reversibly or irreversibly inhibiting interleukin-1β converting enzyme (Caspase-1, ICE). The method comprises the step of administering to a human or higher mammal an effective amount of a composition comprising one or more of the interleukin-1β converting enzyme inhibitors according to the present invention.

In a second aspect, as stated herein, Caspase-1 (ICE) is responsible for the cleavage of the inactive precursor of interleukin-1β (IL-1β) to release the active cytokine interleukin-1β. It has been discovered that Caspase-1 is localized to monocyte membranes and therefore inflammatory disorders caused by or otherwise exacerbated by the extracellular presence of the cytokine IL-1β can be treated by the inhibition of Caspase-1.[1,2] These inflammatory disorders include rheumatoid arthritis.

Regulation of the enzyme Caspase-1, (ICE) by way of administering a composition capable of reversibly or irreversibly inhibiting said enzymes, provides a method for controlling, modulating, mediating, or otherwise abating the inflammation of joints and other forms of synovial tissue associated with osteoarthritis and rheumatoid arthritis.

It is now recognized that in addition to degeneration of neurons associated with Huntington's disease, Caspase-3 expression is up-regulated in apoptotic hippocampal neurons from Alzheimer's disease patients.[3]

Regulation of the enzyme Caspase-3 by way of administering a composition capable of reversibly or irreversibly inhibiting said enzymes, provides a method for controlling, modulating, mediating, or otherwise abating the hippocampal neuron damage associated with Alzheimer's disease because of the over expression of one or more Caspase enzymes and the extracellular release of cytokines.

There is a growing preponderance of evidence to indicate that one or more Caspase enzymes are inappropriately activated in neurogenerative disorders and contribute to the death of neurons, in fact, activated Caspase-8 has been identified in degenerating neurons from Huntington's disease patients.[4] Caspase-1 has been implicated as a mediating factor in cell apoptosis. Apoptosis itself is the most common mechanism by which an organism removes unwanted or damaged cells and this ability is critically important during normal tissue development, inter alia, homeostasis, remodeling, immune response, and defense processes. Apoptosis is, therefore, implicated as contributing to several neurological disorders including Huntington's disease.[5]

Regulation of the enzyme Caspase-1, (ICE) and/or the enzyme Caspase-8, individually or collectively, by way of administering a composition capable of reversibly or irreversibly inhibiting said enzymes, provides a method for controlling, modulating, mediating, or otherwise abating the neurogenerative disorders associated with Huntington's disease.

As can be seen from the above, cell apoptosis, as well as up regulation of Caspase enzymes is a cause for not only inflammatory disease (arthritis and the like) but the degeneration of neurons and the cause of associated neurological disorders, inter alia, Parkinson's disease, Huntington's Disease and Alzheimer's disease.

The present invention therefore encompasses a method for treating separately or collectively one or more diseases, said method comprising the step of contacting a human or higher mammal with a composition comprising one or more of the Caspase inhibitors of the present invention.

As it relates to the specifically controlling the extracellular release of IL-1 □ this cytokine has been implicated as a major catabolic cytokine in the degenerative cascade leading to the loss of cartilage in osteoarthritic patients[6] and to joint inflammation and the associated pain.[7] Indeed, interleukin-1β converting enzyme (ICE) is presently the only enzyme known to be responsible for the release of interleukin-1β. This release occurs when the precursor form of interleukin-1β is converted to an active form, which is then released extracellularly. It has been discovered that the presence of joint synovitis and synovial effusion in osteoarthritic patients is the direct response to the local formation of pro-inflammatory cytokines, particularly, interleukin-1β.[8]

Osteoarthritis is a degenerative articular disorder associated with progressive structural changes in cartilage, bone and synovial tissue leading to the total loss of cartilage and joint function. It has been found that interleukin-1β is elevated in chondrocytes derived from osteoarthric joints as compared to normal non-arthritic cartilage and synovium. It has been reported that inhibition of interleukin-1β using an ICE inhibitor significantly reduces cartilage protoglycan loss in the collagen-induced arthritis model.[9]

It has now been surprisingly found that administering one or more of said compounds comprises a method for controlling or modulating the loss of cartilage in osteoarthritic patients. In addition, administering said compounds comprises a method for controlling or modulating the joint inflammation and pain associated with the swelling of tissue associated with extracellular release of cytokines.

The compounds of the present invention can be administered prophylacticly. For example, in cases wherein inflammation and cartilage damage is anticipated because of ageing or other high risk, inter alia, obesity, sports activity or which inflammation and damage is anticipated as a side effect resulting from the treatment of a more severe disease state (e.g. via chemotherapy).

Because the interleukin-1β converting enzyme inhibitors of the present invention can be delivered in a manner wherein more than one site of control can be achieved, more than one disease state can be modulated at the same time. Non-limiting examples of diseases which are affected by control or inhibition of interleukin-1β converting enzyme, thereby modulating the presence of IL-1β (excessive cytokine activity), include osteoarthritis, rheumatoid arthritis, diabetes, human Immunodeficiency virus (HIV) infection.

A method for controlling osteoporosis in humans or higher mammals, said method comprising the step of administering to a human or higher mammal and effective amount of a composition comprising one or more of the interleukin-1β converting enzyme inhibitors.

The following citations footnoted herein above are included herein by reference.

1. Schreiber, R. D. et al., In *Samter's Immunologic Diseases:* Frank, M. M. et al. Eds.:Little, Brown and Co,: Boston, Mass. (1994); 279–310.
2. Ghayur T.; et al., *High Throughput Screening for Novel Anti-Inflammatories.* Khan M. (Ed.) Birkhauser Verlag Publishers, Basel, Switzerland (2000) 35–48.
3. Gervais, F. et al., *Cell* (1999), 97, 395–406.
4. Sánchez, I.; et al., *Neuron* (1999), 22, 623–633.
5. Perutz, M. F.; et al., *Trends Biochem. Sci.* (1999), 24(2) 58–63
6. J-P Pelletier et al., "Cytokines and Inflammation in Cartilage Degradation": in *Osteoarthritis, Rheumatic Disease Clinics of North America,* ed. R. W. Moskowith, (Philadelphia: W. B. Sanders, 1993), 545–568.
7. F. Fernandez-Madrid et al., "Magnetic Resonace Features of Osteoarthritis of the Knee," *J. Magn. Reson. Imaging,* 12 (1994): 703–709.
8. S. A. Stimpson et al., "Exacerbation of Arthritis by IL-1 in Rat Joints Previously Injured by Peptidoglycan-Polysaccharide," *J. Immunol.* 140 (1988): 2964–2969.
9. W. B. van den Berg et al., "Amelioration of Established Murine Collagen-induced Arthritis with anti-IL-1 Treatment," *Clin. Exp. Immunol.* 95, (1994): 237–243.

PROCEDURES

The compounds of the present invention can be evaluated for efficacy, for example, measurements of ICE inhibition constants, $K_i$, and $IC_{50}$ values can be obtained by any method chosen by the formulator. Conveniently the formulator can measure the release of, inter alia, IL-1β or cleavage of substrates by Caspace-1, Caspace-3, and Caspace-8.

THP-1 cells are human monocyte cells (mononuclear cells) which are utilized to determine in vitro cytokine inhibition. THP-1 cells, like other cell types, respond to extracellular stimulation. These stimuli include cytokines, as well as lipopolysaccharides (LPS), endotoxins, and even ultra violet light. The specific cellular response elicited by these various forms of stimuli are mediated or otherwise regulated by one or more cellular enzymes.

In the case of Caspase-1 enzyme, a signaling cascade, which includes the release of pro-inflammatory cytokines, inter alia, interleukin-1α, interleukin-1β, and TNF-α can be taken advantage of to determine the ability of chemical species to inhibit the enzyme and consequent release of said cytokines. The enzymes are themselves implicated in various disease states and processes, including cartilage degradation associated with arthritis.

One in vitro assay used to establish activity (preliminary screening) of relevant compounds of the present invention includes the following general concepts and procedures. A control sample of THP-1 cells is first stimulated to release a cytokine, in this case IL-1β, exposing the cell to LPS. The THP-1 cells which are utilized to measure suppression of cytokine release, are first incubated with the inhibitors of the present invention prior to stimulation with LPS. The supernatant from each screening sample is analyzed by standard hIL-1β ELISA protocol. The cells which remain after removal of the supernatant are treated with MTS tetrazolium to establish cell viability.

The in vitro results are reported as the $IC_{50}$, defined herein as:

$$IC_{50} = \frac{[I]}{\left[\frac{V_o}{V_i}\right] - 1}$$

wherein $V_i$ is the initial rate of substrate cleaved in the presence of the test compound at concentration [I], and $V_o$ is the rate of substrate cleavage in the control sample.

Non-limiting examples of suitable assays include:
i) UV-visible substrate enzyme assay as described by L. Al Reiter, *Int. J. Peptide Protein Res.,* 43, 87–96 (1994).
ii) Fluorescent substrate enzyme assay as described by Thornberry et al., *Nature,* 356, 768–774 (1992) and Thornberry et al., *Biochemistry,* 33, 393–3940 (1994).
iii) PBMC Cell assay as described in U.S. Pat. No. 6,204,261 B1 Batchelor et al., issued Mar. 20, 2001.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound or its enantiomeric or diasteriomeric form or a pharmaceutically acceptable salt thereof, said compound having the formula:

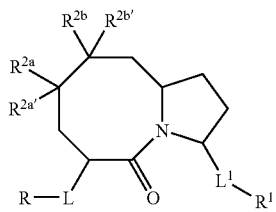

wherein R is a ring chosen from:
i) substituted or unsubstituted $C_3$–$C_{10}$ non-aromatic carbocyclic;
ii) substituted or unsubstituted $C_6$–$C_{10}$ aryl;
iii) substituted or unsubstituted $C_1$–$C_{10}$ heterocyclic; and
iv) substituted or unsubstituted $C_1$–$C_{10}$ heteroaryl;
$R^1$ is a cysteine trap;
$R^{2a}$, $R^{2a'}$, $R^{2b}$, and $R^{2b'}$ are each independently hydrogen, hydroxyl, —N($R^6$)$_2$, halogen, $C_1$–$C_4$ alkyl, and $C_1$–$C_4$ alkoxy; or $R^{2a'}$ and $R^{2b'}$ can be taken together to form a double bond;
L and $L^1$ are linking units each independently having the formula:

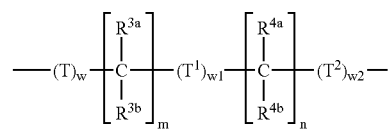

T, $T^1$, and $T^2$ are each independently selected from the group consisting of:
i) —$NR^6$—;
ii) —O—;
iii) —$S(O)_2$—;
iv) —$NR^6S(O)_2$—; and
v) —$S(O)_2NR^6$—;
$R^6$ is hydrogen, substituted or unsubstituted $C_1$–$C_{10}$ linear, branched, or cyclic alkyl, $C_6$–$C_{10}$ aryl, and $C_7$–$C_{12}$ alkylenearyl; the indices w, $w^1$, and $w^2$ are each independently 0 or 1;
$R^{3a}$, $R^{3b}$, $R^{4a}$, and $R^{4b}$ are each independently:
i) hydrogen;
ii) $C_1$–$C_4$ linear, branched, and cyclic alkyl;
iii) $R^{3a}$ and $R^{3b}$ or $R^{4a}$ and $R^{4b}$ can be taken together to form a carbonyl unit; and
iv) two $R^{3a}$ or two $R^{3b}$ units from adjacent carbon atoms or two $R^{4a}$ or two $R^{4b}$ units from adjacent carbon atoms can be taken together to form a double bond;

the index m is from 0 to 5; the index n is from 0 to 5.

2. A compound according to claim 1 comprising a scaffold having the formula:

i)

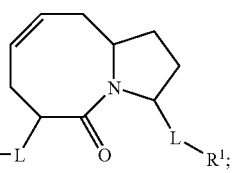

ii)

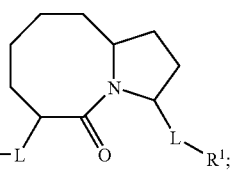

iii)

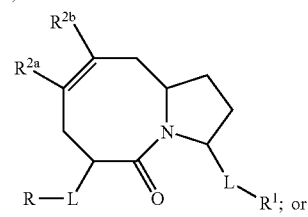

iv)

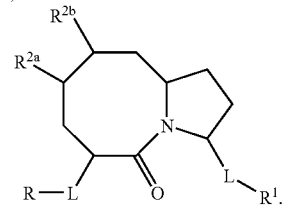

3. A compound according to claim 1 wherein $R^1$ is a reversible cysteine trap having the formula:

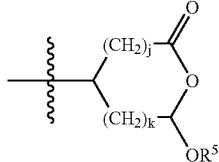

wherein $R^5$ is hydrogen; $C_1$–$C_4$ alkyl; substituted or unsubstituted $C_6$–$C_{10}$ aryl; and substituted or unsubstituted $C_7$–$C_{20}$ alkylenearyl; the indices j and k are each independently 0, 1 or 2.

4. A compound according to claim 3 wherein $R^1$ is a reversible cysteine trap having the formula:

a)
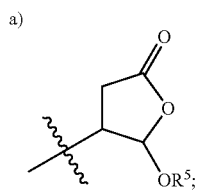

b)
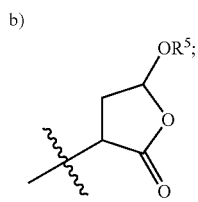

c)
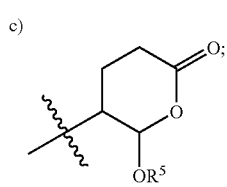

d)
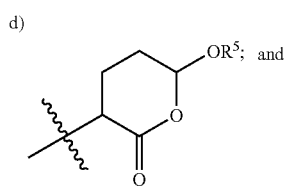

e)
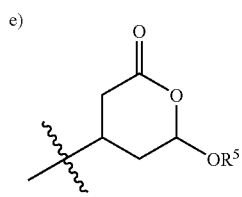

wherein $R^5$ is hydrogen, $C_1$–$C_4$ alkyl, or benzyl.

5. A compound according to claim 1 wherein $R^1$ is a reversible cysteine trap having the formula:

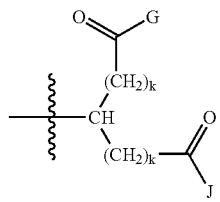

wherein G is —OH or a labile unit and J is a unit selected from the group:
  i) hydrogen;
  ii) substituted or unsubstituted $C_6$–$C_{10}$ aryl;
  iii) substituted or unsubstituted $C_7$–$C_{20}$ alkylenearyl;
  iv) substituted or unsubstituted $C_1$–$C_{10}$ heteroaryl;
  v) —$CH_2N(R^{21})_2$;
  vi) —$C(O)R^{21}$;
  vii) —$C(O)N(R^{21})_2$; and
  viii) —$C(O)OR^{21}$;
$R^{21}$ is hydrogen, substituted or unsubstituted $C_6$–$C_{10}$ aryl, substituted or unsubstituted $C_7$–$C_{20}$ alkylenearyl, and substituted or unsubstituted $C_1$–$C_{10}$ heteroaryl; each index k is independently 0, 1, or 2.

6. A compound according to claim 5 wherein $R^1$ has the formula:

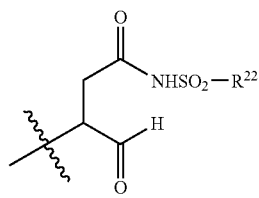

wherein $R^{22}$ is $C_1$–$C_4$ alkyl.

7. A compound according to claim 5 wherein $R^1$ has the formula:

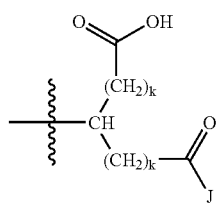

wherein J is —$(CH)_uR^{23}$; $R^{23}$ is a substituted or unsubstituted $C_6$–$C_{10}$ aryl; the index u is from 0 to 10.

8. A compound according to claim 7 wherein J is selected from the group consisting of benzyl, 2-phenylethyl, 3-phenylpropyl, 4-phenylbutyl, and 5-phenylpentyl.

9. A compound according to claim 5 wherein J is —$CH_2N(R^{21})_2$ and one $R^{21}$ is hydrogen and the other is an $C_7$–$C_{20}$ alkylenearyl unit selected from the group consisting of benzyl, 2-phenylethyl, 3-phenylpropyl, 4-phenylbutyl, and 5-phenylpentyl.

10. A compound according to claim 5 wherein J is an $C_7$–$C_{20}$ alkylenearyl unit selected from the group consisting of benzyl, 2-phenylethyl, 3-phenylpropyl, 4-phenylbutyl, and 5-phenylpentyl.

11. A compound according to claim 1 wherein $R^1$ is an α,α-difluoro ketone reversible cysteine trap having the formula:

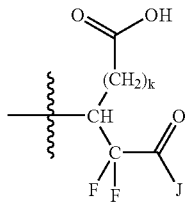

wherein J is a unit selected from the group:
  i), hydrogen;
  ii) substituted or unsubstituted $C_6$–$C_{10}$ aryl;
  iii) substituted or unsubstituted $C_7$–$C_{20}$ alkylenearyl;
  iv) substituted or unsubstituted $C_1$–$C_{10}$ heteroaryl;
  v) —$CH_2N(R^{21})_2$;
  vi) —$C(O)R^{21}$;
  vii) —$C(O)N(R^{21})_3$; and
  viii) $C(O)OR^{21}$;
$R^{21}$ is hydrogen, substituted or unsubstituted $C_6$–$C_{10}$ aryl, substituted or unsubstituted $C_7$–$C_{20}$ alkylenearyl, and substituted or unsubstituted $C_1$–$C_{10}$ heteroaryl; each index k is independently 0, 1, or 2.

12. A compound according to claim 1 wherein $R^1$ is an irreversible cysteine trap having the formula:

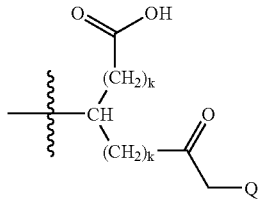

wherein Q is a leaving group selected from:
  i) substituted or unsubstituted $C_2$–$C_{10}$ heterocyclic or $C_1$–$C_{10}$ heteroaryl;
  ii) —$OC(O)R^{11}$;
  iii) —$NHSO_2R^{12}$;
  iv) —$ONR^{13}C(O)R^3$;
  v) halogen;
  vi) —$NHC(O)OR^{14}$;
  vii) —$NHC(O)NHR^{15}$;
  ix) —$OR^{16}$;
  x) —$SR^{17}$;
  xi) —$SSR^{18}$;
  xii) —$SSO_3R^{19}$; and
  xiii) —$OP(O)(R^{20})_2$;
wherein $R^{11}$ is $C_6$–$C_{10}$ aryl, $C_7$–$C_{20}$ alkylenearyl, —$NHR^{24}$; $R^{24}$ is $C_1$–$C_4$ alkyl; $R^{12}$ is $C_1$–$C_{12}$ linear, branched, or cyclic alkyl; $R^{13}$ is hydrogen, $C_1$–$C_4$ alkyl, substituted or unsubstituted $C_6$–$C_{10}$ aryl, substituted or unsubstituted $C_7$–$C_{20}$ alkylenearyl, or two $R^{13}$ units can be taken together to form a fused or no-fused ring having from 3 to 12 atoms: $R^{14}$ is substituted or unsubstituted $C_6$–$C_{10}$ aryl or substituted or unsubstituted $C_7$–$C_{20}$ alkylenearyl; $R^{15}$ is $C_1$–$C_4$ alkyl, substituted or unsubstituted $C_6$–$C_{10}$ aryl, and substituted or unsubstituted $C_7$–$C_{20}$ alkylenearyl; $R^{16}$ is $C_1$–$C_4$ alkyl; $R^{17}$ and $R^{18}$ are substituted or unsubstituted $C_6$–$C_{10}$ aryl, and substituted or unsubstituted $C_7$–$C_{20}$ alkylenearyl; $R^{19}$ is hydrogen, $C_1$–$C_4$ alkyl, substituted or unsubstituted $C_6$–$C_{10}$ aryl, and substituted or unsubstituted $C_7$–$C_{20}$ alkylenearyl; $R^{20}$ is substituted or unsubstituted $C_6$–$C_{10}$ aryl, and substituted or unsubstituted $C_7$–$C_{20}$ alkylenearyl; each index k is independently 0, 1, or 2.

13. A compound according to claim 12 wherein $R^1$ is a cysteine trap having the formula:

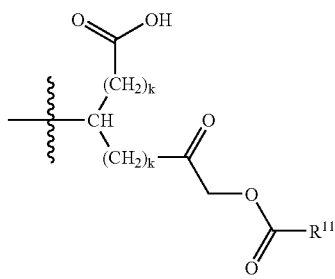

wherein $R^{11}$ is a substituted $C_6$–$C_{10}$ aryl unit.

14. A compound according to claim 13 wherein $R^{11}$ is 2,6-dimethylphenyl or 2,6-dichlorophenyl.

15. A compound according to claim 1 wherein L, and $L^1$ are each independently selected from the group consisting of:
  i) —C(O)NH—;
  ii) —NHC(O)—;
  iii) —NHC(O)NH—;
  iv) —C(O)C(O)—;
  v) —C(O)—;
  vi) —C(O)O—;
  vii) —OC(O)—;
  viii) —NH—;
  ix) —NHS(O)_2—;
  x) —S(O)_2NH—;
  xi) —S(O)_2—;
  xii) and mixtures thereof.

16. A compound according to claim 1 wherein R is a substituted or unsubstituted $C_6$–$C_{10}$ aryl ring selected from the group consisting of phenyl, 2-fluorophenyl, 3-fluorophenyl, 4-fluorophenyl, 3-fluoro-4-methylphenyl, 3-fluoro-4-methoxyphenyl, 3-chloro-2-methylphenyl, 3-chloro-6-methylphenyl, 3-chloro-4-methoxyphenyl, 3-chloro-4-hydroxyphenyl, 3,5-difluorophenyl, 2,6-dichlorophenyl, 2-chlorophenyl, 3-chlorophenyl, 4-chlorophenyl, 3,4-dichlorophenyl, 3,5-dichlorophenyl, 3-chloro-4-fluorophenyl, 2-bromophenyl, 3-bromophenyl, and 4-bromophenyl.

17. A compound according to claim 1 wherein R is a substituted or unsubstituted $C_6$–$C_{10}$ aryl ring selected from the group consisting of 2-methylphenyl, 3-methylphenyl, 4-methylphenyl, 3,5-dimethylphenyl, 2-ethylphenyl, 3-ethylphenyl, 4-ethylphenyl, 3-ethyl-4-methylphenyl 3-propylphenyl, and 3-butylphenyl.

18. A compound according to claim 1 wherein R is a substituted or unsubstituted $C_6$–$C_{10}$ aryl ring selected from the group consisting of 2-methoxyphenyl, 3-methoxyphenyl, 4-methoxyphenyl, 2-ethoxyphenyl, 3-ethoxyphenyl, 4-ethoxyphenyl, 4-propoxyphenyl, 4-butoxyphenyl, and 3,4,5-trimethoxy-phenyl.

19. A compound according to claim 1 wherein R is a substituted or unsubstituted $C_6$–$C_{10}$ aryl ring selected from the group consisting of 3-aminonaphth-2-yl, 4-dimethylaminonaphth-1-yl, 2-aminophenyl, 3-aminophenyl, 4-aminophenyl, 3,4-dimethylaminophenyl, 4-amino-3-chlorophenyl, 4-amino-3,5-dichlorophenyl, 4-dimethylaminophenyl, 2-acetylaminophenyl, 3-acetylaminophenyl, 4-acetylaminophenyl, 4-isobutyrylaminophenyl, 4-propionylaminophenyl, 4-butrylaminophenyl, 4-phenylacetylaminophenyl, 3,4-diacetylaminophenyl, 4-(N-acetyl-N-methylamino)-phenyl, and 4-benzoylaminophenyl.

20. A compound according to claim 1 wherein R is a substituted or unsubstituted $C_6$–$C_{10}$ aryl ring selected from the group consisting of 2-trifluoromethylphenyl, 3-trifluoromethylphenyl, 4-trifluoromethylphenyl, 4-hydroxymethyl-phenyl, naphth-1-yl, naphth-2-yl, 4-biphenyl, 4-phenoxyphenyl, 4-(3-methyl-ureido)-phenyl, 4-sulfamoylphenyl, 3-acetylphenyl, 4-acetylphenyl, 3-hydroxyphenyl, 4-hydroxyphenyl, 4-benzyloxyphenyl, and 4-methanesulfonylphenyl.

21. A compound according to claim 1 wherein R is a substituted or unsubstituted $C_3$–$C_{10}$ non-aromatic carbocyclic ring selected from the group consisting of cyclopropyl, cyclobutyl, cyclohexyl, cyclopentyl, cyclohexenyl, and cyclopentanyl.

22. A compound according to claim 1 wherein R is a substituted or unsubstituted $C_1$–$C_{10}$ heteroaryl unit selected from the group consisting of pyridin-2-yl, pyridin-3-yl, pyridin-4-yl, 3-chloropyridin-2-yl, 4-chloropyridin-2-yl, 5-chloropyridin-2-yl, 6-chloropyridin-2-yl, 3-methylpyridin-3-yl, 4-methylpyridin-3-yl, 5-methylpyridin-3-yl, vinyl pyridin-4-yl, and vinyl pyridin-3-yl.

23. A compound according to claim 1 wherein R is a substituted or unsubstituted $C_1$–$C_{10}$ heteroaryl unit selected from the group consisting of thiophen-3-yl, thiophen-2-yl, pyrimidin-2-yl, pyrimidin-4-yl, pyrimidin-5-yl, 2-isobutoxy-pyrimidin-4-yl, 2-isobutylaminopyrimidin-4-yl, 2-phenoxypyrimidin-4-yl, 2-ethyl-5-methyl-2H-pyrazol-3-yl, 2,4-dimethyl-thiazol-5-yl, 5-methyl-isoxazol-3-yl, 1H-imidazol-2-yl, [1,2,3]thiadiazol-5-yl, furan-2-yl, furan-3-yl, 4,5-dimethyl-2-furanyl, 5-bromo-2-furanyl, and 2-(phenylamino)pyrimidin-4-yl.

24. A compound according to claim 1 wherein R is a substituted or unsubstituted $C_1$–$C_{10}$ heteroaryl ring selected from the group consisting of quinolin-2-yl, quinolin-3-yl, quinolin-4-yl, quinolin-5-yl, quinolin-8-yl, isoquinolin-1-yl, isoquinolin-3-yl, 1,2,3,4-tetrahydro-quinolin-2-yl, 1,2,3,4-tetrahydro-quinolin-3-yl, benzofuran-2-yl, benzofuran-3-yl, benzofuran-5-yl, 1H-indol-5-yl, benzo[b]thiophen-5-yl, benzo[b]thiophen-3-yl, benzo[b]thiophen-2-yl, 3H-benzotriazol-5-yl, 1-methyl-1H-indol-2-yl, 3H-benzimidazol-5-yl, 4-methoxy-quinolin-2-yl, and thieno[2,3-b]thiophen-2-yl.

25. A compound according to claim 1 wherein R is a substituted or unsubstituted $C_1$–$C_{10}$ heterocyclic ring selected from the group consisting of pyrrolidin-1-yl, piperidin-1-yl, piperidin-4-yl, and piperazin-1-yl.

26. A compound according to claim 2 having the formula:

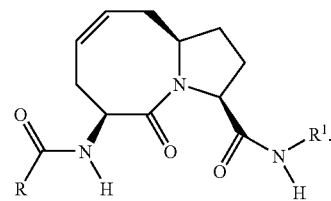

27. A compound selected from the group consisting of:
(3S,6S,10aS)-6-Benzoylamino-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-(2-Methylbenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-(3-Methylbenzoylamino)-5-oxo-1,2,3,5,6,7,10,10a-octahydro-pyrrolo[1,2-a]azocine-3-carboxylic acid (2-hydroxy-5-oxo-tetrahydro-furan-3yl)-amide;

(3S,6S,10aS)-6-(4-Methylbenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-(2-Fluorobenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-(3-Fluorobenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-(4-Fluorobenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-(2-Chlorobenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-(3-Chlorobenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-(4-Chlorobenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-(2-Methoxybenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-(3-Methoxybenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6R,10aS)-6-(3-Methoxybenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-(4-Methoxybenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-[(2-Trifluoromethyl)benzoylamino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-[(3-Trifluoromethyl)benzoylamino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-[(4-Trifluoromethyl)benzoylamino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-[(3,4,5,-Trimethoxy)benzoylamino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide; and (3S,6S,10aS)-6-[(Naphthalene-2-carbonyl)amino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide.

28. A compound selected from the group consisting of:

(3S,6S,10aS)-6-Benzoylamino-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-(2-Methylbenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-(3-Methylbenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-(4-Methylbenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-(2-Fluorobenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-(3-Fluorobenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-(4-Fluorobenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-(2-Chlorobenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-(3-Chlorobenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-(4-Chlorobenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-(2-Methoxybenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-(3-Methoxybenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-(4-Methoxybenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-[(2-Trifluoromethyl)benzoylamino]-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-[(3-Trifluoromethyl)benzoylamino]-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-[(4-Trifluoromethyl)benzoylamino]-5-oxo-1,2,3,5,6,7,10,10a-octahydro-pyrrolo[1,2-a]azocine-3-carboxylic acid (2-ethoxy-5-oxo-tetrahydro-furan-3-yl)-amide;

(3S,6S,10aS)-6-[(3,4,5-Trimethoxy)benzoylamino]-5-oxo-1,2,3,5,6,7,10,10a-octahydro-pyrrolo[1,2-a]azocine-3-carboxylic acid (2-ethoxy-5-oxo-tetrahydro-furan-3-yl)-amide; and (3S,6S,10aS)-6-[(Naphthalene-2-carbonyl)amino]-5-oxo-1,2,3,5,6,7,10,10a-octahydro-pyrrolo[1,2-a]azocine-3-carboxylic acid (2-ethoxy-5-oxo-tetrahydro-furan-3-yl)-amide.

29. A compound selected from the group consisting of:

(3S,6S,10aS)-6-[4-(Acetylamino)benzoylamino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-Benzenesulfonylamino-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

5-Oxo-(3S,6S,10aS)-6-(4-phenoxy-benzoylamino-1,2,3,5,6,7,10,10a-octahydro-pyrrolo[1,2-a]azocine-3-carboxylic acid (2-hydroxy-5-oxo-tetrahydro-furan 3-yl)-amide;

(3S,6S,10aS)-6-(5-Chloro-2-methylbenzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-Benzoic acid-4-[3-(2-hydroxy-5-oxo-tetrahydro-furan-3-ylcarbamoyl)-5oxo-1,2,3,5,6,7,10,10a-octahydro-pyrrolo[1,2-a]azocine-6-ylcarbamoyl]-phenyl ester;

(3S,6S,10aS)-6-(4-Benzoylamino-benzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide;

(3S,6S,10aS)-6-Hydroxy-3-methyl-benzoylamino)-9-methyl-5-oxo-1,2,3,5,6,7,10,10a-octahydro-pyrrolo[1,2-a]azocine-3-carboxylic acid (2-hydroxy-5-oxo-tetrahydro-furan-3-yl)-amide; and (3S,6S,10aS)-6-(3-Fluoro-4-methoxy-benzoylamino)-5-oxo-1,2,3,5,6,7,10,10a-octahydro-pyrrolo[1,2-a]azocine-3-carboxylic acid (2-hydroxy-5-oxo-tetrahydro-furan-3-yl)-amide.

30. A compound selected from the group consisting of:
(3S,6S,10aS)-6-[4(Acetylamino)benzoylamino]-5-oxo-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-6-Benzenesulfonylamino-5-oxo-1,2,3,5,6,7,10,10a-octahydro-pyrrolo[1,2-a]azocine-3-carboxylic acid (2-ethoxy-5-oxo-tetrahydro-furan-3-yl)-amide;
5-Oxo-(3S,6S,10aS)-6-(4-phenoxy-benzoylamino)-1,2,3,5,6,7,10,10a-octahydro-pyrrolo[1,2-a]azocine-3-carboxylic acid (2-ethoxy-5-oxo-tetrahydro-furan 3-yl)-amide;
(3S,6S,10aS)-6-(5-Chloro-2-methylbenzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-Benzoic acid-4-[3-(2-ethoxy-5-oxo-tetrahydro-furan-3-ylcarbamoyl)-5-oxo-1,2,3,5,6,7,10,10a-octahydro-pyrrolo[1,2-a]azocin-6-ylcarbamoyl]-phenyl ester;
(3S,6S,10aS)-6-(4-Benzoylamino-benzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-6-(4-Hydroxy-3-methyl-benzoylamino)-9-methyl-5oxo-1,2,3,5,6,7,10,10a-octahydro-pyrrolo[1,2-a]azocine-3-carboxylic acid (2-ethoxy-5-oxo-tetrahydro-furan-3-yl)-amide; and
(3S,6S,10aS)-6-(3-Fluoro-4-methoxy-benzoylamino)-5-oxo-1,2,3,5,6,7,10,10a-octahydro-pyrrolo[1,2-a]azocine-3-carboxylic acid (2-ethoxy-5-oxo-tetrahydro-furan-3-yl)-amide.

31. A compound selected from the group consisting of:
5-Oxo-(3S,6S,10aS)-6-[(thiophene-3-carbonyl)-amino]-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-6-[(Isoquinoline-1-carbonyl)-amino]-9-methyl-5-oxo-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-6-[(Isoquinoline-1-carbonyl)-amino]-9-methyl-5-oxo-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-6-[(Benzo[b]thiophene-2-carbonyl)-amino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide; and
(3S,6S,10aS)-6-[(Benzo[b]thiophene-7-carbonyl)-amino]-5-oxo-1,2,3,5,6,7,10,10a-octahydro-pyrrolo[1,2-a]azocine-3-carboxylic acid (2-hydroxy-5-oxo-tetrahydro-furan-3-yl)-amide; and
(3S,6S,10aS)-6-(1,3-Dioxo-1,3-dihydro-iSoindol-2-yl)-5-oxo-1,2,3,5,6,7,10,10a-octahydro-pyrrolo[1,2-a]azocine-3-carboxylic acid (2-hydroxy-5-oxo-tetrahydro-furan-3-yl)-amide.

32. A compound selected from the group consisting of:
3S,6S,10aS)-5-Oxo-(6-[(thiophene-3-carbonyl)-amino]-1,2,3,5,6,7,10,10a-octahydro-pyrrolo[1,2-a]azocine-3-carboxylic acid (2-ethoxy-5-oxo-tetrahydro-furan-3-yl)-amide; and
(3S,6S,10aS)-6-[(Benzo(b)thiophene-2-carbonyl)-amino]-5-oxo-1,2,3,5,6,7,10,10a-octahydro-pyrrolo[1,2-a]azocine-3-carboxylic acid (2-ethoxy-5-oxo-tetrahydro-furan-3-yl)-amide,
(3S,6S,10aS)-6-[(Benzo[b]thiophene-7-carbonyl)-amino]-5-oxo-1,2,3,5,6,7,10,10a-octahydro-pyrrolo1,2-a]azocine-3-carboxylic acid (2-ethoxy-5-oxo-tetrahydro-furan-3-yl)-amide; and
(3S,6S,10aS)-6-(1,3-Dioxo-1,3-dihydro-iSoindol-2-yl)-5-oxo-1,2,3,5,6,7,10,10a-octahydro-pyrrolo[1,2-a]azocine-3-carboxylic acid (2-ethoxy-5-oxo-tetrahydro-furan-3-yl)-amide.

33. A compound according to claim 2 having the formula:

34. A compound selected from the group consisting of:
(3S,6S,10aS)-5-Oxo-6-(3-phenyl-ureido)-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-(3-phenyl-ureido)-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-[3-(4-fluorophenyl)ureido]-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-[3-(4-fluorophenyl)ureido]-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-[3-(4-chlorophenyl)ureido]-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-[3-(4-chlorophenyl)ureido]-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-[3-(4-methylphenyl)ureido]-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-[3-(4-methylphenyl)ureido]-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-[3-(4-methoxyphenyl)ureido]-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-[3-(4-methoxyphenyl)ureido]-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-[3-(4-trifluoromethylphenyl)ureido]-1,2,3,5,6,7,10,10a-octahydro-pyrrolo[1,2-a]azocine-3-carboxylic acid (2-hydroxy-5-oxo-tetrahydro-furan-3-yl)-amide; and
(3S,6S,10aS)-5-Oxo-6-[3-(4-trifluoromethylphenyl)ureido]-1,2,3,5,6,7,10,10a-octahydro-pyrrolo[1,2-a]azocine-3-carboxylic acid (2-ethoxy-5-oxo-tetrahydro-furan-3-yl)-amide.

35. A compound according to claim 2 having the formula:

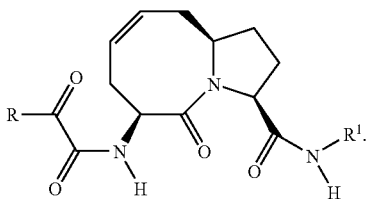

36. A compound selected from the group consisting of:
(3S,6S,10aS)-5-Oxo-6-(2-oxo-2-phenyl-acetylamino)-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-(2-oxo-2-phenyl-acetylamino)-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-[2-oxo-(2-fluorophenyl)-acetylamino]-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-[2-oxo-(2-fluorophenyl)-acetylamino]-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-[2-oxo-(3-fluorophenyl)-acetylamino]-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-[2-oxo-(3-fluorophenyl)-acetylamino]-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-[2-oxo-(4-fluorophenyl)-acetylamino]-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-[2-oxo-(4-fluorophenyl)-acetylamino]-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-[2-oxo-(2-methoxyphenyl)-acetylamino]-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-[2-oxo-(2-methoxyphenyl)-acetylamino]-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-[2-oxo-(3-methoxyphenyl)-acetylamino]-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-[2-oxo-(3-methoxyphenyl)-acetylamino]-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-[2-oxo-(4-methoxyphenyl)-acetylamino]-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-[2-oxo-(4-methoxyphenyl)-acetylamino]-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-(2-oxo-thien-2-yl-acetylamino)-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-(2-oxo-thien-2-yl-acetylamino)-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-(2-oxo-furan-2-yl-acetylamino)-1,2,3,5,6,7,10,10a-octahydro-pyrrolo[1,2-a]azocine-3-carboxylic acid (2-hydroxy-5-oxo-tetrahydro-furan-3-yl)-amide;
(3S,6S,10aS)-5-Oxo-6-(2-oxo-furan-2-yl-acetylamino)-1,2,3,5,6,7,10,10a-octahydro-pyrrolo[1,2-a]azocine-3-carboxylic acid (2-ethoxy-5-oxo-tetrahydro-furan-3-yl)-amide;
(3S,6S,10aS)-5-Oxo-6-(2-oxo-benzo[b]thiophen-2-yl-acetylamino)-1,2,3,5,6,7,10,10a-octahydro-pyrrolo[1,2-a]azocine-3-carboxylic acid (2-hydroxy-5-oxo-tetrahydro-furan-3-yl)-amide; and
(3S,6S,10aS)-5-Oxo-6-(2-oxo-benzo[b]thiophen-2-yl-acetylamino)-1,2,3,5,6,7,10,10a-octahydro-pyrrolo[1,2-a]azocine-3-carboxylic acid (2-ethoxy-5-oxo-tetrahydro-furan-3-yl)-amide.

37. A compound according to claim 2 having the formula:

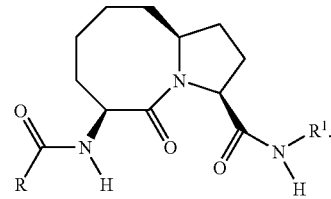

38. A compound selected from the group consisting of:
(3S,6S,10aS)-6-Benzoylamino-5-oxo-decahydro-pyrrolo[1,2-a]azocine-3-carboxylic acid (2-hydroxy-5-oxo-tetrahydro-furan-3-yl)-amide;
(3S,6R,10aS)-6-Benzoylamino-5-oxo-decahydro-pyrrolo[1,2-a]azocine-3-carboxylic acid (2-hydroxy-5-oxo-tetrahydro-furan-3-yl)-amide;
(3S,6S,10aS)-6-(2-Methylbenzoylamino)-5-oxo-decahydro-pyrrolo[1,2-a]azocine-3-carboxylic acid (2-hydroxy-5-oxo-tetrahydro-furan-3-yl)-amide;
(3S,6S,10aS)-6-(3-Methylbenzoylamino)-5-oxo-decahydro-pyrrolo[1,2-a]azocine-3-carboxylic acid (2-hydroxy-5-oxo-tetrahydro-furan-3-yl)-amide;
(3S,6S,10aS)-6-(4-Methylbenzoylamino)-5-oxo-decahydro-pyrrolo[1,2-a]azocine-3-carboxylic acid (2-hydroxy-5-oxo-tetrahydro-furan-3-yl)-amide;
(3S,6S,10aS)-6-(2-Fluorobenzoylamino)-5-oxo-decahydro-pyrrolo[1,2-a]azocine-3-carboxylic acid (2-hydroxy-5-oxo-tetrahydro-furan-3-yl)-amide;
(3S,6S,10aS)-6-(3-Fluorobenzoylamino)-5-oxo-decahydro-pyrrolo[1,2-a]azocine-3-carboxylic acid (2-hydroxy-5-oxo-tetrahydro-furan-3-yl)-amide;
(3S,6S,10aS)-6-(4-Fluorobenzoylamino)-5-oxo-decahydro-pyrrolo[1,2-a]azocine-3-carboxylic acid (2-hydroxy-5-oxo-tetrahydro-furan-3-yl)-amide;

(3S,6S,10aS)-6-(2-Chlorobenzoylamino)-5-oxo-decahydro-pyrrolo[1,2-a]azocine-3-carboxylic acid (2-hydroxy-5-oxo-tetrahydro-furan-3-yl)-amide;
(3S,6S,10aS)-6-(3-Chlorobenzoylamino)-5-oxo-decahydro-pyrrolo[1,2-a]azocine-3-carboxylic acid (2-hydroxy-5-oxo-tetrahydro-furan-3-yl)-amide;
(3S,6S,10aS)-6-(4-Chlorobenzoylamino)-5-oxo-decahydro-pyrrolo[1,2-a]azocine-3-carboxylic acid (2-hydroxy-5-oxo-tetrahydro-furan-3-yl)-amide;
(3S,6S,10aS)-6-(2-Methoxybenzoylamino)-5-oxo-decahydro-pyrrolo[1,2-a]azocine-3-carboxylic acid (2-hydroxy-5-oxo-tetrahydro-furan-3-yl)-amide;
(3S,6S,10aS)-6-(3-Methoxybenzoylamino)-5-oxo-decahydro-pyrrolo[1,2-a]azocine-3-carboxylic acid (2-hydroxy-5-oxo-tetrahydro-furan-3-yl)-amide;
(3S,6S,10aS)-6-(4-Methoxybenzoylamino)-5-oxo-decahydro-pyrrolo[1,2-a]azocine-3-carboxylic acid (2-hydroxy-5-oxo-tetrahydro-furan-3-yl)-amide;
(3S,6S,10aS)-6-[(2-Trifluoromethyl)benzoylamino]-5-oxo-decahydro-pyrrolo[1,2-a]azocine-3-carboxylic acid (2-hydroxy-5-oxo-tetrahydro-furan-3-yl)-amide;
(3S,6S,10aS)-6-[(3-Trifluoromethyl)benzoylamino]-5-oxo-decahydro-pyrrolo[1,2-a]azocine-3-carboxylic acid (2-hydroxy-5-oxo-tetrahydro-furan-3-yl)-amide;
(3S,6S,10aS)-6-[(4-Trifluoromethyl)benzoylamino]-5-oxo-decahydro-pyrrolo[1,2-a]azocine-3-carboxylic acid (2-hydroxy-5-oxo-tetrahydro-furan-3-yl)-amide;
(3S,6S,10aS)-6-[(3,4,5-Trimethoxy)benzoylamino]-5-oxo-decahydro-pyrrolo[1,2-a]azocine-3-carboxylic acid (2-hydroxy-5-oxo-tetrahydro-furan-3-yl)-amide;
(3S,6S,10aS)-6-[(Naphthalene-2-carbonyl)amino]-5-oxo-decahydro-pyrrolo[1,2-a]azocine-3-carboxylic acid (2-hydroxy-5-oxo-tetrahydro-furan-3-yl)-amide, and
(3S,6S,10aS)-6-[(Isoquinoline-2-carbonyl)amino]-5-oxo-decahydro-pyrrolo[1,2-a]azocine-3-carboxylic acid (2-hydroxy-5-oxo-tetrahydro-furan-3-yl)-amide.

39. A compound selected from the group consisting of:
(3S,6S,10aS)-6-Benzoylamino-5-oxo-decahydro-pyrrolo[1,2-a]azocine-3-carboxylic acid (2-ethoxy-5-oxo-tetrahydro-furan-3-yl)-amide;
(3S,6S,10aS)-6-(2-Methylbenzoylamino)-5-oxo-decahydro-pyrrolo[1,2-a]azocine-3-carboxylic acid (2-ethoxy-5-oxo-tetrahydro-furan-3-yl)-amide;
(3S,6S,10aS)-6-(3-Methylbenzoylamino)-5-oxo-decahydro-pyrrolo[1,2-a]azocine-3-carboxylic acid (2-ethoxy-5-oxo-tetrahydro-furan-3-yl)-amide;
(3S,6S,10aS)-6-(4-Methylbenzoylamino)-5-oxo-decahydro-pyrrolo[1,2-a]azocine-3-carboxylic acid (2-ethoxy-5-oxo-tetrahydro-furan-3-yl)-amide;
(3S,6S,10aS)-6-(2-Fluorobenzoylamino)-5-oxo-decahydro-pyrrolo[1,2-a]azocine-3-carboxylic acid (2-ethoxy-5-oxo-tetrahydro-furan-3-yl)-amide;
(3S,6S,10aS)-6-(3-Fluorobenzoylamino)-5-oxo-decahydro-pyrrolo[1,2-a]azocine-3-carboxylic acid (2-ethoxy-5-oxo-tetrahydro-furan-3-yl)-amide;
(3S,6S,10aS)-6-(4-Fluorobenzoylamino)-5-oxo-decahydro-pyrrolo[1,2-a]azocine-3-carboxylic acid (2-ethoxy-5-oxo-tetrahydro-furan-3-yl)-amide;
(3S,6S,10aS)-6-(2-Chlorobenzoylamino)-5-oxo-decahydro-pyrrolo[1,2-a]azocine-3-carboxylic acid (2-ethoxy-5-oxo-tetrahydro-furan-3-yl)-amide;
(3S,6S,10aS)-6-(3-Chlorobenzoylamino)-5-oxo-decahydro-pyrrolo[1,2-a]azocine-3-carboxylic acid (2-ethoxy-5-oxo-tetrahydro-furan-3-yl)-amide;
(3S,6S,10aS)-6-(4-Chlorobenzoylamino)-5-oxo-decahydro-pyrrolo[1,2-a]azocine-3-carboxylic acid (2-ethoxy-5-oxo-tetrahydro-furan-3-yl)-amide;
(3S,6S,10aS)-6-(2-Methoxybenzoylamino)-5-oxo-decahydro-pyrrolo[1,2-a]azocine-3-carboxylic acid (2-ethoxy-5-oxo-tetrahydro-furan-3-yl)-amide;
(3S,6S,10aS)-6-(3-Methoxybenzoylamino)-5-oxo-decahydro-pyrrolo[1,2-a]azocine-3-carboxylic acid (2-ethoxy-5-oxo-tetrahydro-furan-3-yl)-amide;
(3S,6S,10aS)-6-(4-Methoxybenzoylamino)-5-oxo-decahydro-pyrrolo[1,2-a]azocine-3-carboxylic acid (2-ethoxy-5-oxo-tetrahydro-furan-3-yl)-amide;
(3S,6S,10aS)-6-[(2-Trifluoromethyl)benzoylamino]-5-oxo-decahydro-pyrrolo[1,2-a]azocine-3-carboxylic acid (2-ethoxy-5-oxo-tetrahydro-furan-3-yl)-amide;
(3S,6S,10aS)-6-[(3-Trifluoromethyl)benzoylamino]-5-oxo-decahydro-pyrrolo[1,2-a]azocine-3-carboxylic acid (2-ethoxy-5-oxo-tetrahydro-furan-3-yl)-amide;
(3S,6S,10aS)-6-[(4-Trifluoromethyl)benzoylamino]-5-oxo-decahydro-pyrrolo[1,2-a]azocine-3-carboxylic acid (2-ethoxy-5-oxo-tetrahydro-furan-3-yl)-amide;
(3S,6S,10aS)-6-[(3,4,5-Trimethoxy)benzoylamino]-5-oxo-decahydro-pyrrolo[1,2-a]azocine-3-carboxylic acid (2-ethoxy-5-oxo-tetrahydro-furan-3-yl)-amide; and
(3S,6S,10aS)-6-[(Naphthalene-2-carbonyl)amino]-5-oxo-decahydro-pyrrolo[1,2-a]azocine-3-carboxylic acid (2-ethoxy-5-oxo-tetrahydro-furan-3-yl)-amide.

40. A compound according to claim 1 having the formula:

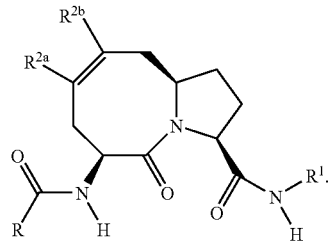

41. A compound selected from the group consisting of:
(3S,6S,10aR)-9-Methyl-6-[(naphthalene-2-carbonyl)-amino]-5-oxo-1,2,3,5,6,7,10,10a-octahydropyrrolo[1,2-a]azocine-3-carboxylic acid(2-hydroxy-5-oxo-tetrahydro-furan-3-yl)-amide;
(3S,6S,10aR)-9-Methyl-5-oxo-6-(3-trifluoromethyl-benzoylamino)-1,2,3,5,6,7,10,10a-octahydropyrrolo[1,2-a]azocine-3-carboxylic acid(2-hydroxy-5-oxo-tetrahydro-furan-3-yl)-amide;
(3S,6S,10aR)-8-Methyl-6-[(naphthalene-2-carbonyl)-amino]-5-oxo-1,2,3,5,6,7,10,10a-octahydropyrrolo[1,2-a]azocine-3-carboxylic acid(2-hydroxy-5-oxo-tetrahydro-furan-3-yl)-amide; and
(3S,6S,10aR)-8-Methyl-5-oxo-6-(3-trifluoromethyl-benzoylamino)-1,2,3,5,6,7,10,10a-octahydropyrrolo[1,2-a]azocine-3-carboxylic acid(2-hydroxy-5-oxo-tetrahydro-furan-3-yl)-amide.

42. A pharmaceutical composition comprising:
A) an effective amount of one or more compounds, including all enantiomeric or diasteriomeric forms or pharmaceutically acceptable salts thereof, said compound having the formula:

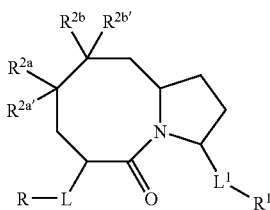

wherein R is a ring chosen from:
i) substituted or unsubstituted $C_3$–$C_{10}$ non-aromatic carbocyclic;
ii) substituted or unsubstituted $C_6$–$C_{10}$ aryl;
iii) substituted or unsubstituted $C_1$–$C_{10}$ heterocyclic; and
iv) substituted or unsubstituted $C_1$–$C_{10}$ heteroaryl;
$R^1$ is a cysteine trap;
$R^{2a}$, $R^{2a'}$, $R^{2b}$ and $R^{2b'}$ are each independently hydrogen, hydroxyl, —$N(R^6)_2$, halogen, $C_1$–$C_4$ alkyl, and $C_1$–$C_4$ alkoxy; or $R^{2a'}$ and $R^{2b'}$ can be taken together to form a double bond;
L and $L^1$ are linking units each independently having the formula:

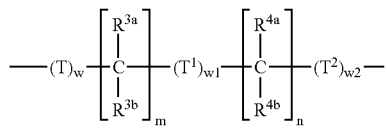

T, $T^1$, and $T^2$ are each independently selected from the group consisting of:
i) —$NR^6$—;
ii) —O—;
iii) —$S(O)_2$—;
iv) —$NR^6S(O)_2$—; and
v) —$S(O)_2NR^6$—;
$R^6$ is hydrogen, substituted or unsubstituted $C_1$–$C_{10}$ linear, branched, or cyclic alkyl, $C_6$–$C_{10}$ aryl, and $C_7$–$C_{20}$ alkylenearyl; the indices w, $w^1$, and $w^2$ are each independently 0 or 1;
$R^{3a}$, $R^{3b}$, $R^{4a}$ and $R^{4b}$ are each independently:
i) hydrogen;
ii) $C_1$–$C_4$ linear, branched, and cyclic alkyl;
iii) $R^{3a}$ and $R^{3b}$ or $R^{4a}$ and $R^{4b}$ can be taken together to form a carbonyl unit; and
iv) two $R^{3a}$ or two $R^{3b}$ units from adjacent carbon atoms or two $R^{4a}$ or two $R^{4b}$ units from adjacent carbon atoms can be taken together to form a double bond;
the index m is from 0 to 5; the index n is from 0 to 5; and B) one or more pharmaceutically acceptable excipients.

43. A method for controlling one or more interleukin-1β converting enzyme inhibitor mediated or interleukin-1β converting enzyme inhibitor modulated mammalian diseases or conditions, selected from the group consisting of osteoarthritis, rheumatoid arthritis, Huntington's disease, Parkinson's disease, Alzheimer's, diabetes, and human Immunodeficiency virus (HIV), said method comprising the step of administering to a human or higher mammal and effective amount of a composition comprising one or more compounds according to claim 1.

44. A method for treating osteoarthritis in humans or higher mammals, said method comprising the step of administering to a human or higher mammal and effective amount of a composition comprising one or more compounds according to claim 1.

* * * * *